US011591660B2

(12) United States Patent
Pinsky et al.

(10) Patent No.: US 11,591,660 B2
(45) Date of Patent: Feb. 28, 2023

(54) METHODS AND REAGENTS FOR DETECTION OF CHIKUNGUNYA VIRUS OR CHIKUNGUNYA VIRUS AND DENGUE VIRUS

(71) Applicant: The Board of Trustees of the Leland Stanford Junior University, Stanford, CA (US)

(72) Inventors: Benjamin A. Pinsky, San Jose, CA (US); Jesse Waggoner, Atlanta, GA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 251 days.

(21) Appl. No.: 16/070,274

(22) PCT Filed: Jan. 14, 2017

(86) PCT No.: PCT/US2017/013604
§ 371 (c)(1),
(2) Date: Jul. 14, 2018

(87) PCT Pub. No.: WO2017/124054
PCT Pub. Date: Jul. 20, 2017

(65) Prior Publication Data
US 2019/0024195 A1 Jan. 24, 2019

Related U.S. Application Data

(60) Provisional application No. 62/278,967, filed on Jan. 14, 2016.

(51) Int. Cl.
*C12Q 1/70* (2006.01)
(52) U.S. Cl.
CPC ......... *C12Q 1/701* (2013.01); *C12Q 2600/16* (2013.01)
(58) Field of Classification Search
None
See application file for complete search history.

(56) References Cited

U.S. PATENT DOCUMENTS

| | | | | |
|---|---|---|---|---|
| 2003/0050470 | A1* | 3/2003 | An | C07H 21/00 435/6.14 |
| 2009/0263806 | A1* | 10/2009 | Carrick | C12Q 1/701 435/6.16 |
| 2009/0281042 | A1 | 11/2009 | Ezra et al. | |
| 2015/0225801 | A1 | 8/2015 | Cai et al. | |

FOREIGN PATENT DOCUMENTS

| | | | | |
|---|---|---|---|---|
| WO | 2014/039010 A1 | 3/2014 | | |
| WO | WO-2014055746 A1 | * | 4/2014 | ............ C12Q 1/701 |

OTHER PUBLICATIONS

Lanciotti, Genetic and Serologic Properties of Zika Virus Associated with an Epidemic, Yap State, Micronesia, 2007, Emerging Infectious Diseases, vol. 14, No. 8, pp. 1232-1239, 2007. (Year: 2007).*
Gen Bank Accession No. HQ234501 (Year: 2012).*
Pongsiri, Multiplex real-time RT-PCR for detecting chikungunya virus and dengue virus, Asian Pacific Journal of Tropical Medicine, 5(5): 342-346, 2012. (Year: 2012).*
Ho, Establishment of one-step SYBR green-based real time-PCR assay for rapid detection and quantification of chikungunya virus infection, Virol. J., 7:13, 1-7, 2010. (Year: 2010).*
Lowe, A computer program for selection of oligonucleotide primers for polymerase chain reactions, Nucleic Acids Research, 18(7): 1757-1761, 1990. (Year: 1990).*
Waggoner (2014) "Once Bitten: Multiplex Detection of Dengue, Chikungunya and Emerging Arboviruses," Northern California Branch American Society for Microbiology, Fall 2014 Meeting, Oct. 4, 2014 (Oct. 4, 2014), pp. 1-45.
Cecilia et al. (2014) "Development of a multiplex real-time RT-PCR assay for simultaneous detection of dengue and chikungunya viruses," Archives of Virology, Sep. 19, 2014 (Sep. 19, 2014), vol. 160, Iss 1, pp. 323-327.
PCT/US2017/013604 International Search Report.
Batty et al., "A Modified RNA-Seq Approach for Whole Genome Sequencing of RNA Viruses from Faecal and Blood Samples", PLoS One, Jun. 10, 2013, 8(6): e66129.
Das et al., "Removal of real-time reverse transcription polymerase chain reaction (RT-PCR) inhibitors associated with cloacal swab samples and tissues for improved diagnosis of Avian influenza virus by RT-PCR", J Vet Diagn Invest, 2009, 21: 771-778.
Li et al., "Development of a direct reverse-transcription quantitative PCR (dirRT-qPCR) assay for clinical Zika diagnosis", International Journal of Infectious Diseases, Aug. 2019, 85:167-174.
Buck et al., "Design Strategies and Performance of Custom DNA Sequencing Primers", BioTechniques, Sep. 1999, 27(3): 528-536.
Chen et al., "Primer Design Assistant (PDA): a web-based primer design tool", Nucleic Acids Research, 2003, 31(13): 3751-3754.

* cited by examiner

Primary Examiner — Samuel C Woolwine
Assistant Examiner — Carolyn L Greene
(74) Attorney, Agent, or Firm — James S. Keddie; Bozicevic, Field & Francis LLP

(57) ABSTRACT

Methods and oligonucleotide reagents for diagnosing chikungunya virus and Zika virus infections are described. In particular, the invention relates to quantitative assays that can detect all lineages of chikungunya virus and Zika virus and distinguish chikungunya virus and Zika virus from each other as well as dengue virus and other arbovirus pathogens.

11 Claims, No Drawings
Specification includes a Sequence Listing.

METHODS AND REAGENTS FOR DETECTION OF CHIKUNGUNYA VIRUS OR CHIKUNGUNYA VIRUS AND DENGUE VIRUS

TECHNICAL FIELD

The present invention pertains generally to chikungunya virus and Zika virus and viral diagnostics for detecting these viruses individually or in combination. In particular, the invention relates to quantitative assays that can detect all lineages of chikungunya virus and Zika virus and distinguish chikungunya virus and Zika virus from each other as well as dengue virus and other arbovirus pathogens.

BACKGROUND

Over the past decade, chikungunya virus (CHIKV) has emerged from being a relatively rare arbovirus that caused sporadic outbreaks of human disease in Africa and Asia to the cause of a pandemic that has affected millions of people across five continents (Powers (2010) Clin. Lab. Med. 30:209-219). As a result, CHIKV has spread to new regions where dengue virus (DENV) is endemic, including, since December 2013, tropical and subtropical regions of the Western Hemisphere (Leparc-Goffart et al. (2014) Lancet 383:514). This has created a new challenge for health care systems that care for patients living in or returning from affected areas, as the clinical presentation of dengue and chikungunya overlap significantly (Cleton et al. (2015) PLoS Negl Trop Dis 9:e0004073; Hochedez et al. (2008) Am. J. Trop. Med. Hyg. 78:710-713; Lee et al. (2012) PLoS Negl. Trop. Dis. 6:e1786; Mohd et al. (2013) J. Clin. Virol. 56:141-145). The differentiation of infections with DENV and CHIKV is important not only for epidemiologic surveillance but also for clinical care, such as initiating appropriate management and providing prognostic information. While certain clinical and laboratory findings have been associated with dengue (thrombocytopenia, leukopenia) or chikungunya (arthralgia/arthritis), these are not sufficiently accurate to determine the cause of illness in all cases without specific testing (Cleton et al., supra; Hochedez et al., supra; Mohd et al., supra).

Zika virus (ZIKV) is a mosquito-borne flavivirus that was first identified in a rhesus monkey from the Zika Forest of Uganda in 1947. Prior to 2007, very few cases of human infection with ZIKV had been identified and all had occurred in Africa or Asia. In 2007, a large ZIKV outbreak occurred on Yap Island, Federated States of Micronesia. Patients presented with a rash, fever, arthrlagias and conjunctivitis, and it was estimated that 73% of the Yap population older than 3 years of age was infected during this outbreak. The virus has since spread to islands of the South Pacific, and in May 2015, a large ZIKV outbreak began in northeastern Brazil. The virus has spread to at least six states in Brazil, with an estimate of 500,000-1,000,000 infections to date. Importantly, the virus has also been temporally linked to cases of microcephaly in Brazil and neurologic malformations in babies born during outbreaks in the South Pacific.

ZIKV emergence in Brazil has coincided with an increase in cases of DENV infection and ongoing CHIKV transmission. Human infection with ZIKV often presents with symptoms that overlap with both of these viruses, which has created a new challenge for health care systems that care for patients living in or returning from affected areas. The differentiation of infections with these viruses is important not only for epidemiologic surveillance but also for clinical care, such as initiating appropriate management and providing prognostic information. While certain clinical and laboratory findings have been associated with dengue (thrombocytopenia, leukopenia) or chikungunya (arthralgia/arthritis), these are not sufficiently accurate to determine the cause of illness in all cases without specific testing. Clinical and laboratory findings in acute ZIKV infections have not been thoroughly studied owing to its recent emergence over the last few years.

Molecular tests are the most sensitive diagnostics for DENV, CHIKV, or ZIKV in the acute setting. Serologic testing is also frequently performed on paired acute and convalescent serum, but this can only confirm a diagnosis in retrospect. Also, high rates of false-positive DENV serologic results have been reported in patients with ZIKV. A number of molecular tests have been published for the detection of DENV and CHIKV, but only two real-time reverse transcriptase PCRs (rRT-PCRs) have been reported for ZIKV. Both of these assays are run as individual reactions. Molecular testing for all three viruses, using recommended assays, can entail performing up to six amplification reactions for a single patient sample followed by detection using gel electrophoresis. This results in increased costs, prolonged turnaround times, and decreased rates of detection as all samples often cannot be tested for each virus.

Thus, there remains a need for the development of effective strategies for the diagnosis, treatment, and prevention of chikungunya, Zika, and dengue viral infections. The availability of nucleic acid diagnostic tests capable of efficiently detecting chikungunya, Zika, and dengue viruses in human specimens such as plasma, serum and respiratory secretions will assist the medical community in better diagnosing and treating these arbovirus infections.

SUMMARY

The present invention is based on the development of sensitive, reliable nucleic acid-based diagnostic assays for the detection of chikungunya and Zika viruses in biological samples from potentially infected subjects. The assays allow rapid detection of all lineages of chikungunya virus and Zika virus and can distinguish chikungunya virus and Zika virus from each other as well as from other arbovirus pathogens. The methods can also be used to quantitate the amount of virus that is present in a biological sample. If infection is detected, an individual can be given appropriate therapy, and steps can be taken to prevent or reduce further transmission and spread of the viruses. If infection is ruled-out, other potential causes of undifferentiated febrile illness can be further investigated.

In addition, the assays described herein can be readily combined with other assays for detection of other arbovirus pathogens. Multiplex assays can be used to detect infection by a single virus or coinfection by more than one virus. In particular, multiplex assays can be used to detect chikungunya virus, Zika virus, and dengue virus, or any combination thereof in a single assay to determine if an individual is infected with any of these viruses or coinfected with more than one virus.

The methods utilize primers and probes for amplifying and/or detecting target sequences of one or more chikungunya virus, Zika virus, or dengue virus genotypes, to allow detection of a single viral genotype or multiple genotypes simultaneously in a single assay. In certain embodiments, the virus sequences are detected using reverse transcriptase-polymerase chain reaction (RT-PCR), for example, using real-time RT-PCR and/or multiplex RT-PCR. Other nucleic-acid based detection techniques such as, but not limited to, nucleic acid sequence based amplification (NASBA), a 5' nuclease assay (e.g., TaqMan), or transcription-mediated amplification (TMA), can also be used.

Exemplary primers (SEQ ID NO:6 and SEQ ID NO:7) and probes (SEQ ID NO:8) for detection of chikungunya virus are shown in Example 1 (see Table 1). Changes to the nucleotide sequences of these primers and probes may be introduced corresponding to genetic variations in particular chikungunya strains. For example up to three nucleotide changes, including 1 nucleotide change, 2 nucleotide changes, or three nucleotide changes, may be made in a sequence selected from the group consisting of SEQ ID NOS:6-8, wherein the oligonucleotide primer or probe is capable of hybridizing to and amplifying or detecting a particular chikungunya virus target nucleic acid (e.g., a portion of an NSP2 gene).

Exemplary primers (SEQ ID NOS:9-16) and probes (SEQ ID NOS:17-25) for detection of dengue virus in combination with chikungunya virus and/or Zika virus in multiplex assays are also shown in Example 1 (see Tables 4 and 5). Changes to the nucleotide sequences of these primers and probes may be introduced corresponding to genetic variations in particular dengue strains. For example up to three nucleotide changes, including 1 nucleotide change, 2 nucleotide changes, or three nucleotide changes, may be made in a sequence selected from the group consisting of SEQ ID NOS:9-25, wherein the oligonucleotide primer or probe is capable of hybridizing to and amplifying or detecting a particular dengue virus target nucleic acid.

In one aspect, the invention includes a composition for detecting chikungunya virus in a biological sample using a nucleic acid amplification assay, the composition comprising at least one set of oligonucleotide primers comprising a forward primer and a reverse primer capable of amplifying at least a portion of a chikungunya virus genome, wherein the primers are not more than 40 nucleotides in length, wherein the set of primers is selected from the group consisting of: a) a forward primer comprising the nucleotide sequence of SEQ ID NO:6 and a reverse primer comprising the sequence of SEQ ID NO:7; b) a forward primer comprising at least 10 contiguous nucleotides of the nucleotide sequence of SEQ ID NO:6 and a reverse primer comprising at least 10 contiguous nucleotides of the nucleotide sequence of SEQ ID NO:7; c) a forward primer comprising a nucleotide sequence having at least 95% identity to the sequence of SEQ ID NO:6 and a reverse primer comprising a nucleotide sequence having at least 95% identity to the sequence of SEQ ID NO:7, wherein the primer is capable of hybridizing to and amplifying chikungunya virus nucleic acids in the nucleic acid amplification assay; d) a forward primer and a reverse primer comprising at least one nucleotide sequence that differs from the corresponding nucleotide sequence of the forward primer or reverse primer of the primer set of (a) in that the primer has up to three nucleotide changes compared to the corresponding sequence, wherein the primer is capable of hybridizing to and amplifying chikungunya virus nucleic acids in the nucleic acid amplification assay; and e) a forward primer and a reverse primer comprising nucleotide sequences that are complements of the corresponding nucleotide sequences of the forward primer and reverse primer of a primer set selected from the group consisting of (a)-(d).

In certain embodiments, the composition may further comprise at least one detectably labeled oligonucleotide probe sufficiently complementary to and capable of hybridizing with a chikungunya virus RNA or an amplicon thereof.

An exemplary probe comprises the nucleotide sequence of SEQ ID NO:8. The composition may include a set of probes capable of detecting multiple genotypes of chikungunya virus, including any viral strain of any of the chikungunya virus genotypes (e.g., West African, East/Central/South African (ECSA), and Asian (Indian and south east clades)). In one embodiment, the probe is selected from the group consisting of: a) a probe comprising the sequence of SEQ ID NO:8; b) a probe comprising a nucleotide sequence having at least 95% identity to the sequence of SEQ ID NO:8, wherein the probe is capable of hybridizing to and detecting the chikungunya virus RNA or an amplicon thereof; and c) a probe that differs from the corresponding nucleotide sequence of SEQ ID NO:8 by up to three nucleotide changes, wherein the probe is capable of hybridizing to and detecting the chikungunya virus RNA or an amplicon thereof.

The probe may be detectably labeled with a fluorophore (e.g., a fluorescein or rhodamine derivative). The fluorophore may include, but is not limited to, a CAL Fluor dye, a Quasar dye, an Alexa Fluor, 2', 4', 5', 7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), carboxy-X-rhodamine (ROX), tetramethyl rhodamine (TAMRA), Cy3, Cy5, and Texas Red. In one embodiment, the fluorophore is a CAL Fluor dye selected from the group consisting of CAL Fluor Gold 540, CAL Fluor Orange 560, CAL Fluor Red 590, CAL Fluor Red 610, and CAL Fluor Red 635.

In certain embodiments, the probe comprises a 5'-fluorophore and a 3'-quencher. The 3'-quencher may include, but is not limited to, a black hole quencher (e.g., BHQ-0, BHQ-1, BHQ-2, and BHQ-3), tetramethyl rhodamine (TAMRA), dabcyl, a Qxl quencher, an Iowa black quencher, an Eclipse quencher, an ATTO quencher, and dihydrocyclopyrroloindole tripeptide minor groove binder (MGB). In one embodiment, the probe is a molecular beacon.

In one embodiment, the composition comprises a primer comprising the sequence of SEQ ID NO:6, a primer comprising the sequence of SEQ ID NO:7, and a probe comprising the sequence of SEQ ID NO:8.

In another aspect, the invention includes a method for detecting chikungunya virus, the method comprising: a) contacting nucleic acids of a biological sample suspected of containing chikungunya virus with a composition, as described herein, for detecting chikungunya virus by nucleic acid amplification of viral RNA, b) amplifying at least a portion of a chikungunya virus RNA, if present, wherein the chikungunya virus RNA comprises an NSP2 target sequence; and c) detecting the presence of the amplified nucleic acids using at least one detectably labeled oligonucleotide probe sufficiently complementary to and capable of hybridizing with the chikungunya virus RNA or amplicon thereof, if present, as an indication of the presence or absence of chikungunya virus in the sample. In one embodiment, the method further comprises isolating the chikungunya virus nucleic acids from the biological sample prior to amplification. In another embodiment, the method further comprises isolating the chikungunya virus nucleic acids from the biological sample after amplification.

In another embodiment, the method is performed with at least one probe selected from the group consisting of a) a probe comprising the sequence of SEQ ID NO:8; a probe comprising a nucleotide sequence having at least 95% identity to the sequence of SEQ ID NO:8, wherein the probe is capable of hybridizing to and detecting the chikungunya virus RNA or an amplicon thereof; and a probe that differs from the corresponding nucleotide sequence of SEQ ID NO:8 by up to three nucleotide changes, wherein the probe is capable of hybridizing to and detecting the chikungunya virus RNA or an amplicon thereof.

In certain embodiments, the probe used in the method of detecting chikungunya virus comprises a fluorophore (e.g., fluorescein or rhodamine derivative). The fluorophore may include, but is not limited to, a CAL Fluor dye, a Quasar dye, an Alexa Fluor, 2', 4', 5', 7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), carboxy-X-rhodamine (ROX), tetramethyl rhodamine (TAMRA), Cy3, Cy5, and Texas Red. In one embodiment, the fluorophore is a CAL Fluor dye selected from the group consisting of CAL Fluor Gold 540, CAL Fluor Orange 560, CAL Fluor Red 590, CAL Fluor Red 610, and CAL Fluor Red 635.

In certain embodiments, the detectably labeled probe comprises a 5'-fluorophore and a 3'-quencher. The 3'-quencher may include, but is not limited to, a black hole quencher (e.g., BHQ-0, BHQ-1, BHQ-2, and BHQ-3), tetramethyl rhodamine (TAMRA), dabcyl, a Qxl quencher, an Iowa black quencher, an Eclipse quencher, an ATTO quencher, and dihydrocyclopyrroloindole tripeptide minor groove binder (MGB). In one embodiment, the probe used for detection of chikungunya virus is a molecular beacon.

In another embodiment, the set of primers and probes that are used for detecting chikungunya virus in the biological sample comprise a primer comprising the sequence of SEQ ID NO:6, a primer comprising the sequence of SEQ ID NO:7, and a probe comprising the sequence of SEQ ID NO:8.

In certain embodiments, the method further comprises detecting dengue virus in the biological sample. In one embodiment, the primers used for detecting dengue virus in the biological sample comprise a primer comprising the sequence of SEQ ID NO:9, a primer comprising the sequence of SEQ ID NO:10, a primer comprising the sequence of SEQ ID NO:11, a primer comprising the sequence of SEQ ID NO:12, a primer comprising the sequence of SEQ ID NO:13, a primer comprising the sequence of SEQ ID NO:14, a primer comprising the sequence of SEQ ID NO:15, and a primer comprising the sequence of SEQ ID NO:16.

In another embodiment, the method further comprises using at least one probe for detecting dengue virus, wherein at least one probe is selected from the group consisting of: a) a probe comprising the sequence of SEQ ID NO:17, b) a probe comprising the sequence of SEQ ID NO:18, c) a probe comprising the sequence of SEQ ID NO:19, d) a probe comprising the sequence of SEQ ID NO:20, e) a probe comprising the sequence of SEQ ID NO:21, f) a probe comprising the sequence of SEQ ID NO:22, g) a probe comprising the sequence of SEQ ID NO:23, h) a probe comprising the sequence of SEQ ID NO:24, i) a probe comprising the sequence of SEQ ID NO:25, and j) a probe that differs from the corresponding nucleotide sequence of a probe selected from the group consisting of (a)-(i) in that the probe has up to three nucleotide changes compared to the corresponding sequence, wherein the probe is capable of hybridizing to and detecting the dengue virus RNA or amplicon thereof.

In another embodiment, a set of probes is used for detecting dengue virus in a biological sample, wherein the set of probes comprises a probe comprising the sequence of SEQ ID NO:17, a probe comprising the sequence of SEQ ID NO:18, a probe comprising the sequence of SEQ ID NO:19, and a probe comprising the sequence of SEQ ID NO:20.

In another embodiment, a set of probes is used for detecting dengue virus in a biological sample, wherein the set of probes comprises a probe comprising the sequence of SEQ ID NO:22, a probe comprising the sequence of SEQ ID NO:23, a probe comprising the sequence of SEQ ID NO:24, and a probe comprising the sequence of SEQ ID NO:25.

In another embodiment a set of primers and probes are used for detecting dengue virus in a biological sample comprising: a primer comprising the sequence of SEQ ID NO:9, a primer comprising the sequence of SEQ ID NO:10, a primer comprising the sequence of SEQ ID NO:11, a primer comprising the sequence of SEQ ID NO:12, a primer comprising the sequence of SEQ ID NO:13, a primer comprising the sequence of SEQ ID NO:14, a primer comprising the sequence of SEQ ID NO:15, a primer comprising the sequence of SEQ ID NO:16, a probe comprising the sequence of SEQ ID NO:17, a probe comprising the sequence of SEQ ID NO:18, a probe comprising the sequence of SEQ ID NO:19, and a probe comprising the sequence of SEQ ID NO:20. In one embodiment, the probe comprising the sequence of SEQ ID NO:17 further comprises a 5' FAM fluorophore and a 3' BHQ-1 quencher, the probe comprising the sequence of SEQ ID NO:18 further comprises a 5' CAL Fluor Orange 560 fluorophore and a 3' BHQ-1 quencher, the probe comprising the sequence of SEQ ID NO:19 further comprises a 5' CAL Fluor Red 610 fluorophore and a 3' BHQ-2 quencher, and the probe comprising the sequence of SEQ ID NO:20 further comprises a 5' Quasar Blue 670 fluorophore and a 3' BHQ-2 quencher.

In another embodiment, a set of primers and probes are used for detecting dengue virus in a biological sample comprising: a primer comprising the sequence of SEQ ID NO:9, a primer comprising the sequence of SEQ ID NO:10, a primer comprising the sequence of SEQ ID NO:11, a primer comprising the sequence of SEQ ID NO:12, a primer comprising the sequence of SEQ ID NO:13, a primer comprising the sequence of SEQ ID NO:14, a primer comprising the sequence of SEQ ID NO:15, a primer comprising the sequence of SEQ ID NO:16, a probe comprising the sequence of SEQ ID NO:22, a probe comprising the sequence of SEQ ID NO:23, a probe comprising the sequence of SEQ ID NO:24, and a probe comprising the sequence of SEQ ID NO:25. In one embodiment, the probe comprising the sequence of SEQ ID NO:22 further comprises a 5' FAM fluorophore and a 3' BHQplus quencher, the probe comprising the sequence of SEQ ID NO:23 further comprises a 5' FAM fluorophore and a 3' BHQplus quencher, the probe comprising the sequence of SEQ ID NO:24 further comprises a 5' FAM fluorophore and a 3' BHQplus quencher, and the probe comprising the sequence of SEQ ID NO:25 further comprises a FAM fluorophore and a 3' BHQplus quencher.

In certain embodiments, the method further comprises distinguishing chikungunya virus nucleic acids from dengue virus, West Nile virus, Japanese encephalitis virus, tick-borne encephalitis virus, yellow fever virus, Saint Louis encephalitis virus, Zika virus, o'nyong-nyong virus, Semliki Forest virus, mayaro virus, Ross River virus, Getah virus, Barmah Forest virus, Una virus, hepatitis C virus (HCV), human immunodeficiency virus (HIV), Leptospira, Plasmodium species, or Rift Valley fever virus nucleic acids.

In another aspect, the invention includes an isolated oligonucleotide not more than 40 nucleotides in length comprising: a) a nucleotide sequence comprising at least 10 contiguous nucleotides from a nucleotide sequence selected from the group consisting of SEQ ID NOS:6-8; b) a nucleotide sequence having at least 95% identity to a nucleotide sequence selected from the group consisting of SEQ ID NO:6-8, wherein the oligonucleotide is capable of hybridizing to and amplifying or detecting a chikungunya virus nucleic acid; c) a nucleotide sequence that differs from a nucleotide sequence selected from the group consisting of SEQ ID NOS:6-8 by up to three nucleotide changes, wherein the oligonucleotide is capable of hybridizing to and amplifying or detecting a chikungunya virus nucleic acid; or d) complements of (a)-(c). Oligonucleotides may further comprise a detectable label. For example, the detectable label may be a fluorophore (e.g., fluorescein or rhodamine derivative). The fluorophore may include, but is not limited to, a CAL Fluor dye, a Quasar dye, an Alexa Fluor, 2', 4', 5', 7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), carboxy-X-rhodamine (ROX), tetramethyl rhodamine (TAMRA), Cy3, Cy5, and Texas Red. In one embodiment, the fluorophore is a CAL Fluor dye selected from the group consisting of CAL Fluor Gold 540, CAL Fluor Orange 560, CAL Fluor Red 590, CAL Fluor Red 610, and CAL Fluor Red 635. The oligonucleotide may further comprise a quencher such as, but not limited to black hole quencher (e.g., BHQ-0, BHQ-1, BHQ-2, and BHQ-3), tetramethyl rhodamine (TAMRA), dabcyl, a Qxl quencher, an Iowa black quencher, an Eclipse quencher, an ATTO quencher, and dihydrocyclopyrroloindole tripeptide minor groove binder (MGB). In certain embodiments, the oligonucleotide comprises a nucleotide sequence selected from the group consisting of SEQ ID NOS:6-8 or a complement thereof.

In another aspect, the invention includes a kit for detecting chikungunya virus in a biological sample by nucleic acid amplification of viral RNA. The kit may comprise a composition, as described herein, comprising at least one set of primers including a forward primer and a reverse primer capable of amplifying at least a portion of a chikungunya virus genome, including an NSP2 target sequence. The kit may further comprise written instructions for identifying the presence of the chikungunya virus, quantitating the chikungunya virus, and/or serotyping the chikungunya virus. The kit may also comprise reagents for performing reverse transcriptase polymerase chain reaction (RT-PCR), nucleic acid sequence based amplification (NASBA), transcription-mediated amplification (TMA), a fluorogenic 5' nuclease assay, or other nucleic acid amplification technique. In one embodiment, the kit further comprises oligonucleotide primers and probes for detecting Zika virus and/or dengue virus as described herein.

The methods of the invention can be used to detect chikungunya virus in biological samples such as, but not limited to, blood, plasma, serum, saliva, cerebrospinal fluid (CSF), fibroblasts, epithelial cells, endothelial cells, macrophages, skin, liver, muscle, spleen, lymph nodes, thymus, lung, kidneys, or bone marrow. Chikungunya virus can be specifically detected even in samples containing other viruses or pathogens, such as West Nile virus, Japanese encephalitis virus, tick-borne encephalitis virus, yellow fever virus, Saint Louis encephalitis virus, Zika virus, o'nyong-nyong virus, Semliki Forest virus, mayaro virus, Ross River virus, Getah virus, Barmah Forest virus, Una virus, hepatitis C virus (HCV), Leptospira, Plasmodium species, or Rift Valley fever virus. Moreover, the assays can be used to screen mosquitoes, monkeys, birds, cattle, rodents, and other hosts for chikungunya virus in order to determine if a particular insect or animal population is infected with the virus, thereby preventing further transmission and spread of chikungunya virus infection. Individuals coinfected with chikungunya virus and other arbovirus pathogens (e.g., dengue virus) can also be identified using multiplex assays. Additionally, infected blood samples can be detected and excluded from transfusion, as well as from the preparation of blood derivatives.

Exemplary primers (SEQ ID NOS:27-29) and probes (SEQ ID NO:30) for detection of Zika virus are shown in Example 2 (see Table 6). Changes to the nucleotide sequences of these primers and probes may be introduced corresponding to genetic variations in particular Zika virus strains. For example up to three nucleotide changes, including 1 nucleotide change, 2 nucleotide changes, or three nucleotide changes, may be made in a sequence selected from the group consisting of SEQ ID NOS:27-30, wherein the oligonucleotide primer or probe is capable of hybridizing to and amplifying or detecting a particular Zika virus target nucleic acid (e.g., a conserved viral sequence).

In another aspect, the invention includes a composition for detecting Zika virus in a biological sample using a nucleic acid amplification assay, the composition comprising at least one set of oligonucleotide primers comprising a forward primer and at least one reverse primer capable of amplifying at least a portion of a Zika virus genome, wherein the primers are not more than 40 nucleotides in length, wherein the set of primers is selected from the group consisting of: a) a forward primer comprising the nucleotide sequence of SEQ ID NO:27 and a reverse primer comprising the sequence of SEQ ID NO:28; b) a forward primer comprising the nucleotide sequence of SEQ ID NO:27 and a reverse primer comprising the sequence of SEQ ID NO:29; c) a forward primer comprising the nucleotide sequence of SEQ ID NO:27, a first reverse primer comprising the sequence of SEQ ID NO:28, and a second reverse primer comprising the sequence of SEQ ID NO:29; d) a forward primer comprising at least 10 contiguous nucleotides of the nucleotide sequence of SEQ ID NO:27 and at least one reverse primer comprising at least 10 contiguous nucleotides of a nucleotide sequence selected from the group consisting of SEQ ID NO:28 and SEQ ID NO:29; e) a forward primer comprising a nucleotide sequence having at least 95% identity to the sequence of SEQ ID NO:27 and at least one reverse primer comprising a nucleotide sequence having at least 95% identity to a sequence selected from the group consisting of SEQ ID NO:28 and SEQ ID NO:29, wherein the primer is capable of hybridizing to and amplifying Zika virus nucleic acids in the nucleic acid amplification assay; f) a forward primer and a reverse primer comprising at least one nucleotide sequence that differs from the corresponding nucleotide sequence of the forward primer or reverse primer of the primer set of (a) or (b) in that the primer has up to three nucleotide changes compared to the corresponding sequence, wherein the primer is capable of hybridizing to and amplifying Zika virus nucleic acids in the nucleic acid amplification assay; and g) a forward primer and a reverse primer comprising nucleotide sequences that are complements of the corresponding nucleotide sequences of the forward primer and reverse primer of a primer set selected from the group consisting of (a)-(f).

In certain embodiments, the composition may further comprise at least one detectably labeled oligonucleotide probe sufficiently complementary to and capable of hybridizing with a Zika virus RNA or an amplicon thereof. An exemplary probe comprises the nucleotide sequence of SEQ ID NO:30. The composition may include a set of probes capable of detecting multiple genotypes of Zika virus, including any viral strain of any of the Zika virus genotypes. In certain embodiments, the probe is selected from the group consisting of: a) a probe comprising the sequence of SEQ ID NO:30; b) a probe comprising a nucleotide sequence having at least 95% identity to the sequence of SEQ ID NO:30, wherein the probe is capable of hybridizing to and detecting the Zika virus RNA or an amplicon thereof; and c) a probe that differs from the corresponding nucleotide sequence of SEQ ID NO:30 by up to three nucleotide changes, wherein the probe is capable of hybridizing to and detecting the Zika virus RNA or an amplicon thereof.

In another embodiment, the composition comprises a primer comprising the sequence of SEQ ID NO:27, a primer comprising the sequence of SEQ ID NO:28, a primer comprising the sequence of SEQ ID NO:29, and a probe comprising the sequence of SEQ ID NO:30.

The probe may be detectably labeled with a fluorophore (e.g., a fluorescein or rhodamine derivative). The fluorophore may include, but is not limited to, a CAL Fluor dye, a Quasar dye, an Alexa Fluor, 2', 4', 5', 7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), carboxy-X-rhodamine (ROX), tetramethyl rhodamine (TAMRA), Cy3, Cy5, and Texas Red. In one embodiment, the fluorophore is a CAL Fluor dye selected from the group consisting of CAL Fluor Gold 540, CAL Fluor Orange 560, CAL Fluor Red 590, CAL Fluor Red 610, and CAL Fluor Red 635.

In certain embodiments, the probe comprises a 5'-fluorophore and a 3'-quencher. The 3'-quencher may include, but is not limited to, a black hole quencher (e.g., BHQ-0, BHQ-1, BHQ-2, and BHQ-3), tetramethyl rhodamine (TAMRA), dabcyl, a Qxl quencher, an Iowa black quencher, an Eclipse quencher, an ATTO quencher, and dihydrocyclopyrroloindole tripeptide minor groove binder (MGB). In one embodiment, the probe is a molecular beacon.

In another aspect, the invention includes a method for detecting Zika virus, the method comprising: a) contacting nucleic acids of a biological sample suspected of containing Zika virus with a composition, as described herein, for detecting Zika virus by nucleic acid amplification of viral RNA, b) amplifying at least a portion of a Zika virus RNA, if present; and c) detecting the presence of the amplified nucleic acids using at least one detectably labeled oligonucleotide probe sufficiently complementary to and capable of hybridizing with the Zika virus RNA or amplicon thereof, if present, as an indication of the presence or absence of Zika virus in the sample. In one embodiment, the method further comprises isolating the Zika virus nucleic acids from the biological sample prior to amplification. In another embodiment, the method further comprises isolating the Zika virus nucleic acids from the biological sample after amplification.

In another embodiment, the method is performed with at least one probe selected from the group consisting of a) a probe comprising the sequence of SEQ ID NO:30; a probe comprising a nucleotide sequence having at least 95% identity to the sequence of SEQ ID NO:30, wherein the probe is capable of hybridizing to and detecting the Zika virus RNA or an amplicon thereof; and a probe that differs from the corresponding nucleotide sequence of SEQ ID NO:30 by up to three nucleotide changes, wherein the probe is capable of hybridizing to and detecting the Zika virus RNA or an amplicon thereof.

In certain embodiments, the probe used in the method of detecting Zika virus comprises a fluorophore (e.g., fluorescein or rhodamine derivative). The fluorophore may include, but is not limited to, a CAL Fluor dye, a Quasar dye, an Alexa Fluor, 2', 4', 5', 7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), carboxy-X-rhodamine (ROX), tetramethyl rhodamine (TAMRA), Cy3, Cy5, and Texas Red. In one embodiment, the fluorophore is a CAL Fluor dye selected from the group consisting of CAL Fluor Gold 540, CAL Fluor Orange 560, CAL Fluor Red 590, CAL Fluor Red 610, and CAL Fluor Red 635.

In certain embodiments, the detectably labeled probe comprises a 5'-fluorophore and a 3'-quencher. The 3'-quencher may include, but is not limited to, a black hole quencher (e.g., BHQ-0, BHQ-1, BHQ-2, and BHQ-3), tetramethyl rhodamine (TAMRA), dabcyl, a Qxl quencher, an Iowa black quencher, an Eclipse quencher, an ATTO quencher, and dihydrocyclopyrroloindole tripeptide minor groove binder (MGB). In one embodiment, the probe used for detection of Zika virus is a molecular beacon.

In another embodiment, the set of primers and probes that are used for detecting Zika virus in the biological sample comprise a primer comprising the sequence of SEQ ID NO:27, a primer comprising the sequence of SEQ ID NO:28, a primer comprising the sequence of SEQ ID NO:29, and a probe comprising the sequence of SEQ ID NO:30.

In certain embodiments, the method further comprises distinguishing Zika virus nucleic acids from dengue virus, chikungunya virus, West Nile virus, Japanese encephalitis virus, tick-borne encephalitis virus, yellow fever virus, Saint Louis encephalitis virus, o'nyong-nyong virus, Semliki Forest virus, mayaro virus, Ross River virus, Getah virus, Barmah Forest virus, Una virus, hepatitis C virus (HCV), human immunodeficiency virus (HIV), Leptospira, Plasmodium species, or Rift Valley fever virus nucleic acids.

In certain embodiments, the method further comprises detecting dengue virus and/or chikungunya virus in the biological sample. In one embodiment, detecting the chikungunya virus comprises amplifying at least a portion of the chikungunya virus RNA using at least one set of primers comprising a forward primer and a reverse primer capable of amplifying at least a portion of a chikungunya virus genome comprising an NSP2 target sequence, wherein the primers are not more than about 40 nucleotides in length, wherein the set of primers is selected from the group consisting of: a) a forward primer comprising the nucleotide sequence of SEQ ID NO:6 and a reverse primer comprising the sequence of SEQ ID NO:7; b) a forward primer comprising at least 10 contiguous nucleotides of the nucleotide sequence of SEQ ID NO:6 and a reverse primer comprising at least 10 contiguous nucleotides of the nucleotide sequence of SEQ ID NO:7; c) a forward primer comprising a nucleotide sequence having at least 95% identity to the sequence of SEQ ID NO:6 and a reverse primer comprising a nucleotide sequence having at least 95% identity to the sequence of SEQ ID NO:7, wherein the primer is capable of hybridizing to and amplifying chikungunya virus nucleic acids in the nucleic acid amplification assay; d) a forward primer and a reverse primer comprising at least one nucleotide sequence that differs from the corresponding nucleotide sequence of the forward primer or reverse primer of the primer set of (a) in that the primer has up to three nucleotide changes compared to the corresponding sequence, wherein the primer is capable of hybridizing to and amplifying chikungunya virus nucleic acids in the nucleic acid amplification assay; and e) a forward primer and a reverse primer comprising nucleotide sequences that are complements of the corresponding nucleotide sequences of the forward primer and reverse primer of a primer set selected from the group consisting of (a)-(d).

The amplified chikungunya virus nucleic acids can be detected using at least one detectably labeled oligonucleotide probe sufficiently complementary to and capable of hybridizing with the chikungunya virus RNA or amplicon thereof, if present, as an indication of the presence or absence of chikungunya virus in the sample. In certain embodiments, at least one probe is selected from the group consisting of: a) a probe comprising the sequence of SEQ ID NO:8; b) a probe comprising a nucleotide sequence having at least 95% identity to the sequence of SEQ ID NO:8, wherein the probe is capable of hybridizing to and detecting the chikungunya virus RNA or an amplicon thereof; and c) a probe that differs from the corresponding nucleotide sequence of SEQ ID NO:8 by up to three nucleotide changes, wherein the probe is capable of hybridizing to and detecting the chikungunya virus RNA or an amplicon thereof.

In another embodiment, detecting the chikungunya virus comprises amplifying at least a portion of the chikungunya virus RNA using at least one set of primers comprising a forward primer and a reverse primer capable of amplifying at least a portion of a chikungunya virus genome comprising an NSP2 target sequence, wherein the primers are not more than about 40 nucleotides in length, wherein the set of primers is selected from the group consisting of: a) a forward primer comprising the nucleotide sequence of SEQ ID NO:1 and at least one reverse primer comprising a nucleotide sequence selected from the group consisting of SEQ ID NO:2 and SEQ ID NO:3; b) a forward primer comprising at least 10 contiguous nucleotides of the nucleotide sequence of SEQ ID NO:1 and at least one reverse primer comprising at least 10 contiguous nucleotides of a nucleotide sequence selected from the group consisting of SEQ ID NO:2 and SEQ ID NO:3; c) a forward primer comprising a nucleotide sequence having at least 95% identity to the sequence of SEQ ID NO:1 and at least one reverse primer comprising a nucleotide sequence having at least 95% identity to a nucleotide sequence selected from the group consisting of SEQ ID NO:2 and SEQ ID NO:3, wherein the primer is capable of hybridizing to and amplifying chikungunya virus nucleic acids in the nucleic acid amplification assay; d) a forward primer and a reverse primer comprising at least one nucleotide sequence that differs from the corresponding nucleotide sequence of the forward primer or reverse primer of the primer set of (a) in that the primer has up to three nucleotide changes compared to the corresponding sequence, wherein the primer is capable of hybridizing to and amplifying chikungunya virus nucleic acids in the nucleic acid amplification assay; and e) a forward primer and a reverse primer comprising nucleotide sequences that are complements of the corresponding nucleotide sequences of the forward primer and reverse primer of a primer set selected from the group consisting of (a)-(d). The amplified nucleic acids can be detected using at least one detectably labeled oligonucleotide probe sufficiently complementary to and capable of hybridizing with the chikungunya virus RNA or amplicon thereof, if present, as an indication of the presence or absence of chikungunya virus in the sample. In certain embodiments, at least one probe is selected from the group consisting of: a) a probe comprising a sequence selected from the group consisting of SEQ ID NO:4 and SEQ ID NO:5; b) a probe comprising a nucleotide sequence having at least 95% identity to a sequence selected from the group consisting of SEQ ID NO:4 and SEQ ID NO:5, wherein the probe is capable of hybridizing to and detecting the chikungunya virus RNA or an amplicon thereof; and c) a probe that differs from the corresponding nucleotide sequence of SEQ ID NO:4 or SEQ ID NO:5 by up to three nucleotide changes, wherein the probe is capable of hybridizing to and detecting the chikungunya virus RNA or an amplicon thereof.

In certain embodiments, the method further comprises detecting dengue virus in the biological sample. In one embodiment, the primers used for detecting dengue virus in the biological sample comprise a primer comprising the sequence of SEQ ID NO:9, a primer comprising the sequence of SEQ ID NO:10, a primer comprising the sequence of SEQ ID NO:11, a primer comprising the sequence of SEQ ID NO:12, a primer comprising the sequence of SEQ ID NO:13, a primer comprising the sequence of SEQ ID NO:14, a primer comprising the sequence of SEQ ID NO:15, and a primer comprising the sequence of SEQ ID NO:16.

In another embodiment, the method further comprises using at least one probe for detecting dengue virus, wherein at least one probe is selected from the group consisting of: a) a probe comprising the sequence of SEQ ID NO:17, b) a probe comprising the sequence of SEQ ID NO:18, c) a probe comprising the sequence of SEQ ID NO:19, d) a probe comprising the sequence of SEQ ID NO:20, e) a probe comprising the sequence of SEQ ID NO:21, f) a probe comprising the sequence of SEQ ID NO:22, g) a probe comprising the sequence of SEQ ID NO:23, h) a probe comprising the sequence of SEQ ID NO:24, i) a probe comprising the sequence of SEQ ID NO:25, and j) a probe that differs from the corresponding nucleotide sequence of a probe selected from the group consisting of (a)-(i) in that the probe has up to three nucleotide changes compared to the corresponding sequence, wherein the probe is capable of hybridizing to and detecting the dengue virus RNA or amplicon thereof.

In another aspect, the invention includes an isolated oligonucleotide not more than 40 nucleotides in length comprising: a) a nucleotide sequence comprising at least 10 contiguous nucleotides from a nucleotide sequence selected from the group consisting of SEQ ID NOS:27-30; b) a nucleotide sequence having at least 95% identity to a nucleotide sequence selected from the group consisting of SEQ ID NOS:27-30, wherein the oligonucleotide is capable of hybridizing to and/or amplifying Zika virus nucleic acids; c) a nucleotide sequence that differs from a nucleotide sequence selected from the group consisting of SEQ ID NOS:27-30 by up to three nucleotide changes, wherein the oligonucleotide is capable of hybridizing to and/or amplifying Zika virus nucleic acids; or d) complements of (a)-(c). Oligonucleotides may further comprise a detectable label. For example, the detectable label may be a fluorophore (e.g., fluorescein or rhodamine derivative). The fluorophore may include, but is not limited to, a CAL Fluor dye, a Quasar dye, an Alexa Fluor, 2', 4', 5', 7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), carboxy-X-rhodamine (ROX), tetramethyl rhodamine (TAMRA), Cy3, Cy5, and Texas Red. In one embodiment, the fluorophore is a CAL Fluor dye selected from the group consisting of CAL Fluor Gold 540, CAL Fluor Orange 560, CAL Fluor Red 590, CAL Fluor Red 610, and CAL Fluor Red 635. The oligonucleotide may further comprise a quencher such as, but not limited to black hole quencher (e.g., BHQ-0, BHQ-1, BHQ-2, and BHQ-3), tetramethyl rhodamine (TAMRA), dabcyl, a Qxl quencher, an Iowa black quencher, an Eclipse quencher, an ATTO quencher, and dihydrocyclopyrroloindole tripeptide minor groove binder (MGB). In certain embodiments, the oligonucleotide comprises a nucleotide sequence selected from the group consisting of SEQ ID NOS:27-30 or a complement thereof.

In another aspect, the invention includes a kit for detecting Zika virus in a biological sample by nucleic acid amplification of viral RNA. The kit may comprise a composition, as described herein, comprising at least one set of primers including a forward primer and a reverse primer capable of amplifying at least a portion of a Zika virus genome. The kit may further comprise written instructions for identifying the presence of the Zika virus, quantitating the Zika virus, and/or serotyping the Zika virus. The kit may also comprise reagents for performing reverse transcriptase polymerase chain reaction (RT-PCR), nucleic acid sequence based amplification (NASBA), transcription-mediated amplification (TMA), a fluorogenic 5' nuclease assay, or other nucleic acid amplification technique. In one embodiment, the kit further comprises oligonucleotide primers and probes for detecting dengue virus and/or chikungunya virus.

The methods of the invention can be used to detect Zika virus in biological samples such as, but not limited to, blood, plasma, serum, saliva, cerebrospinal fluid (CSF), urine, amniotic fluid, dendritic cells, fibroblasts, keratinocytes, epithelial cells, endothelial cells, macrophages, and tissue samples obtained from the skin, liver, muscles, joints, spleen, lymph nodes, thymus, lung, brain, nerves, kidneys, or bone marrow. Zika virus can be specifically detected even in samples containing other viruses or pathogens, such as dengue virus, chikungunya virus, West Nile virus, Japanese encephalitis virus, tick-borne encephalitis virus, yellow fever virus, Saint Louis encephalitis virus, o'nyong-nyong virus, Semliki Forest virus, mayaro virus, Ross River virus, Getah virus, Barmah Forest virus, Una virus, hepatitis C virus (HCV), Leptospira, Plasmodium species, or Rift Valley fever virus. Moreover, the assays can be used to screen mosquitoes, monkeys, birds, cattle, rodents, and other hosts for Zika virus in order to determine if a particular insect or animal population is infected with the virus, thereby preventing further transmission and spread of Zika virus infection. Individuals coinfected with Zika virus and other arbovirus pathogens (e.g., dengue virus or chikungunya virus) can also be identified using multiplex assays. Additionally, infected blood samples can be detected and excluded from transfusion, as well as from the preparation of blood derivatives.

In certain embodiments, the kit comprises: written instructions for identifying the presence of Zika virus; and at least one set of primers comprising a forward primer and a reverse primer capable of amplifying at least a portion of a Zika virus genome, wherein the primers are not more than about 40 nucleotides in length, wherein the set of primers is selected from the group consisting of: a) a forward primer comprising the nucleotide sequence of SEQ ID NO:27 and at least one reverse primer comprising a nucleotide sequence selected from the group consisting of SEQ ID NO:28 and SEQ ID NO:29; b) a forward primer comprising at least 10 contiguous nucleotides of the nucleotide sequence of SEQ ID NO:27 and at least one reverse primer comprising at least 10 contiguous nucleotides of a nucleotide sequence selected from the group consisting of SEQ ID NO:28 and SEQ ID NO:29; c) a forward primer comprising a nucleotide sequence having at least 95% identity to the sequence of SEQ ID NO:27 and at least one reverse primer comprising a nucleotide sequence having at least 95% identity to a nucleotide sequence selected from the group consisting of SEQ ID NO:28 and SEQ ID NO:29, wherein the primer is capable of hybridizing to and amplifying Zika virus nucleic acids in the nucleic acid amplification assay; d) a forward primer and at least one reverse primer comprising at least one nucleotide sequence that differs from the corresponding nucleotide sequence of the forward primer or at least one reverse primer of the primer set of (a) in that the primer has up to three nucleotide changes compared to the corresponding sequence, wherein the primer is capable of hybridizing to and amplifying Zika virus nucleic acids in the nucleic acid amplification assay; and e) a forward primer and at least one reverse primer comprising nucleotide sequences that are complements of the corresponding nucleotide sequences of the forward primer and reverse primer of a primer set selected from the group consisting of (a)-(d). In one embodiment, the kit comprises a forward primer comprising the nucleotide sequence of SEQ ID NO:27, a first reverse primer comprising the nucleotide sequence of SEQ ID NO:28, and a second reverse primer comprising the nucleotide sequence of SEQ ID NO:29.

Additionally, the kit may further comprises at least one probe for detecting Zika virus in a biological sample, wherein the probe is selected from the group consisting of: a) a probe comprising the sequence of SEQ ID NO:30; b) a probe comprising a nucleotide sequence having at least 95% identity to the sequence of SEQ ID NO:30, wherein the probe is capable of hybridizing to and detecting the Zika virus RNA or an amplicon thereof; and c) a probe that differs from the corresponding nucleotide sequence of SEQ ID NO:30 by up to three nucleotide changes, wherein the probe is capable of hybridizing to and detecting the Zika virus RNA or an amplicon thereof. In one embodiment, the kit comprises a forward primer comprising the nucleotide sequence of SEQ ID NO:27, a first reverse primer comprising the nucleotide sequence of SEQ ID NO:28, a second reverse primer comprising the nucleotide sequence of SEQ ID NO:29, and a probe comprising the sequence of SEQ ID NO:30.

In another embodiment, the kit further comprises reagents for detecting chikungunya virus. In certain embodiments, the kit comprises at least one set of primers comprising a forward primer and a reverse primer capable of amplifying at least a portion of a chikungunya virus genome comprising an NSP2 target sequence, wherein the primers are not more than about 40 nucleotides in length, wherein the set of primers is selected from the group consisting of: a) a forward primer comprising the nucleotide sequence of SEQ ID NO:6 and a reverse primer comprising the sequence of SEQ ID NO:7; b) a forward primer comprising at least 10 contiguous nucleotides of the nucleotide sequence of SEQ ID NO:6 and a reverse primer comprising at least 10 contiguous nucleotides of the nucleotide sequence of SEQ ID NO:7; c) a forward primer comprising a nucleotide sequence having at least 95% identity to the sequence of SEQ ID NO:6 and a reverse primer comprising a nucleotide sequence having at least 95% identity to the sequence of SEQ ID NO:7, wherein the primer is capable of hybridizing to and amplifying chikungunya virus nucleic acids in the nucleic acid amplification assay; d) a forward primer and a reverse primer comprising at least one nucleotide sequence that differs from the corresponding nucleotide sequence of the forward primer or reverse primer of the primer set of (a) in that the primer has up to three nucleotide changes compared to the corresponding sequence, wherein the primer is capable of hybridizing to and amplifying chikungunya virus nucleic acids in the nucleic acid amplification assay; and e) a forward primer and a reverse primer comprising nucleotide sequences that are complements of the corresponding nucleotide sequences of the forward primer and reverse primer of a primer set selected from the group consisting of (a)-(d).

Additionally, the kit may further comprises at least one probe for detecting chikungunya virus in a biological sample, wherein the probe is selected from the group consisting of: a) a probe comprising the sequence of SEQ ID NO:8; b) a probe comprising a nucleotide sequence having at least 95% identity to the sequence of SEQ ID NO:8, wherein the probe is capable of hybridizing to and detecting the chikungunya virus RNA or an amplicon thereof; and c) a probe that differs from the corresponding nucleotide sequence of SEQ ID NO:8 by up to three nucleotide changes, wherein the probe is capable of hybridizing to and detecting the chikungunya virus RNA or an amplicon thereof.

These and other embodiments of the subject invention will readily occur to those of skill in the art in view of the disclosure herein.

DETAILED DESCRIPTION OF THE INVENTION

The practice of the present invention will employ, unless otherwise indicated, conventional methods of virology, chemistry, biochemistry, recombinant DNA techniques and immunology, within the skill of the art. Such techniques are explained fully in the literature. See, e.g., *Fundamental Virology* (D. M. Knipe, P. M. Howley, D. E. Griffin, R. A. Lamb, M. A. Martin, B. Roizman, S. E. Straus, eds.), Lippincott Williams & Wilkins; Fourth edition, 2001; *Dengue Virus* (Current Topics in Microbiology and Immunology, A. L. Rothman, ed.), Springer, $1^{st}$ edition, 2009; *Frontiers in Dengue Virus Research* (K. A. Hanley and S. C. Weaver eds.), Caister Academic Press, $1^{st}$ edition, 2010; *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, Biochemistry (Worth Publishers, Inc., current addition); Sambrook, et al., *Molecular Cloning: A Laboratory Manual* ($3^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

1. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a virus oligonucleotide" includes a mixture of two or more such oligonucleotides, and the like.

As used herein, the term "chikungunya virus" refers to members of the Togaviridae family of enveloped viruses with a single-stranded positive-sense RNA genome (see, e.g., Singh et al. (2011) Rev. Med. Virol. 21(2):78-88; herein incorporated by reference in its entirety). The term chikungunya virus may include any strain of chikungunya virus, such as a West African strain, East/Central/South African (ECSA) strain, or Asian strain (including Indian or south east clades), which is capable of causing disease in an animal or human subject. In particular, the term encompasses any subtype of chikungunya virus that causes disease in humans, including strains R80422a and the S27 Petersfield. A large number of chikungunya isolates have been partially or completely sequenced. See, e.g., the Virus Pathogen Resource (website at viprbrc.org/brc/home.spg?decorator=toga) and the GenBank database, which contain complete sequences for chikungunya viruses.

As used herein, the term "Zika virus" refers to members of the Flaviviridae family of enveloped viruses with a single-stranded positive-sense RNA genome (see, e.g., Marano et al. (2015) Blood Transfus. 5:1-6, Hayes (2009) Emerg. Infect. Dis. 15(9):1347-1350; herein incorporated by reference in their entireties). The term Zika virus may include any strain of Zika virus which is capable of causing disease in an animal or human subject, including, but not limited to, strains from Africa, Asia, Central and South America, and the Caribbean and Pacific Islands. A large number of Zika virus isolates have been partially or completely sequenced. See, e.g., the Virus Pathogen Resource and the GenBank database, which contain complete sequences for Zika viruses.

As used herein, the term "dengue virus" refers to members of the Flaviviridae family of enveloped viruses with a single-stranded positive-sense RNA genome (see, e.g., *Frontiers in Dengue Virus Research*, Hanley and Weaver (editors), Caister Academic Press, 2010). The term dengue virus may include any serotype of dengue virus, such as serotypes 1-5, which is capable of causing disease in an animal or human subject. In particular, the term encompasses any subtype of dengue virus that causes disease in humans, including strains DEN 1 Hawaii 1944, Den 2 New Guinea C strain, DEN 3 strain H87, and DEN 4 strain H241. A large number of dengue isolates have been partially or completely sequenced. See, e.g., the Broad Institute Dengue Virus Portal (website at broadinstitute.org/annotation/viral/Dengue/); the Dengue Virus Database (website at denguedb.org); the Virus Pathogen Resource (website at viprbrc.org/brc/home.do?decorator=flavi_dengue) and the GenBank database, which contain complete sequences for dengue viruses, including serotypes 1-4.

"Substantially purified" generally refers to isolation of a substance (compound, polynucleotide, oligonucleotide, protein, or polypeptide) such that the substance comprises the majority percent of the sample in which it resides. Typically in a sample, a substantially purified component comprises 50%, preferably 80%-85%, more preferably 90-95% of the sample. Techniques for purifying polynucleotides oligonucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide or oligonucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide molecules. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, DC, which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

A chikungunya virus polynucleotide, oligonucleotide, nucleic acid and nucleic acid molecule, as defined above, is a nucleic acid molecule derived from a dengue virus, including, without limitation, any of the various chikungunya virus strains. The molecule need not be physically derived from the particular isolate in question, but may be synthetically or recombinantly produced.

Nucleic acid and protein sequences for a number of chikungunya virus isolates are known. A representative chikungunya virus sequence is presented in SEQ ID NO:26 of the Sequence Listing. Additional representative sequences, including RNA genomic sequences and sequences of the non-structural polyprotein, the non-structural proteins (nsP1, nsP2, nsP3 and nsP4) produced by proteolytic processing of the non-structural polyprotein, the structural polyprotein, and the structural proteins (Capsid, E1, E2, E3, and 6K) produced by proteolytic processing of the structural polyprotein for virus isolates of various genotypes, including West African, East/Central/South African (ECSA), and Asian (Indian and south east clades) strains are listed in the National Center for Biotechnology Information (NCBI) database. See, for example, NCBI entries: Accession No. AF369024, NC_004162, AF490259, EF210157, JX088705, KR559498, KR559497, KT449801, KM923920, KJ689453, KJ689452, KJ451624, KJ451623, KJ796852, KJ796851, KJ796847, KJ796846, KJ796844, KC488650, HM067743, GU189061, HM045823, HM045822, HM045821, HM045820, HM045819, HM045818, HM045817, HM045816, HM045815, HM045814, HM045813, HM045812, HM045811, HM045810, HM045809, HM045808, HM045807, HM045806, HM045805, HM045804, HM045803, HM045802, HM045801, HM045800, HM045799, HM045798, HM045797, HM045796, HM045795, HM045794, HM045793, HM045792, HM045791, HM045790, HM045789, HM045788, HM045787, HM045786, HM045785, HM045784, HQ456255, HQ456254, HQ456253, HQ456252, HQ456251, GQ905863, AY726732, FJ807899, FJ807898, FJ807897, FJ807896, GQ428215, EF452494, EF452493, FJ959103, EU244823, EF012359, DQ443544, KF151175, KF151174, KP003813, KP003812, KP003811, KP003810, KP003809, KP003808, KP003807, KF872195, HE806461, HM067744, HQ848081, HQ848080, JQ067624, GU199353, GU199352, GU199351, GU199350, FJ807895, FJ807894, FJ807893, FJ807892, FJ807891, FJ807890, FJ807887, EU703762, EU703761, EU703760, EU703759, L37661, AB455494, AB455493, EU564335, EU564334, EF027141, EF027140, EF027139, EF027138, EF027137, EF027136, EF027135, EF027134, AY424803, AF339485, EU192143, EU192142, NC_004162, EU037962, KJ941050, KF151178, KF151177, KF151176, and AB678695; all of which sequences (as entered by the date of filing of this application) are herein incorporated by reference. See also Lo Presti et al. (2014) Asian Pac. J. Trop. Med. 7(12):925-932, Weaver et al. (2015) Antiviral Res. 120:32-39 and Caglioti et al. (2013) New Microbiol. 36(3):211-227 for sequence comparisons and a discussion of genetic diversity and phylogenetic analysis of chikungunya viruses.

A Zika virus polynucleotide, oligonucleotide, nucleic acid and nucleic acid molecule, as defined above, is a nucleic acid molecule derived from a Zika virus, including, without limitation, any of the various Zika virus strains. The molecule need not be physically derived from the particular isolate in question, but may be synthetically or recombinantly produced.

Nucleic acid and protein sequences for a number of Zika virus isolates are known. Representative Zika virus sequences are presented in SEQ ID NO:31 and SEQ ID NO:32 of the Sequence Listing. Additional representative sequences, including RNA genomic sequences and sequences of the polyprotein and the non-structural proteins (NS1, NS2A, NS2B, NS3, NS4A, NS4B, and NS5) and the structural proteins (capsid protein (C), precursor membrane protein (prM), and envelope protein (E)) produced by proteolytic processing of the polyprotein for virus isolates of various strains are listed in the National Center for Biotechnology Information (NCBI) database. See, for example, NCBI entries: Accession No. NC_012532, KU647676, KU556802, KU509998, KU646828, KU646827, KU501217, KU501216, KU501215, KU365780, KU365779, KU365778, KU365777, KU312315, KU312314, KU312313, KU312312, KM078979, KM078978, KM078977, KM078976, KM078975, KM078974, KM078973, KM078972, KM078971, KM078970, KM078969, KM078968, KM078967, KM078966, KM078965, KM078964, KM078963, KM078962, KM078961, KM078960, KM078959, KM078958, KM078957, KM078956, KM078955, KM078954, KM078953, KM078952, KM078951, KM078950, KM078949, KM078948, KM078947, KM078946, KM078945, KM078944, KM078943, KM078942, KM078941, KM078940, KM078939, KM078938, KM078937, KM078936, KM078935, KM078934, KM078933, KM078932, KM078931, KM078930, KM078929, KR816336, KR816335, KR816334, KR816333, KM851039, KR815990, KR815989, KM851038, KM014700, KJ873161, KJ873160, KF993678, LC002520, KJ461621, KJ776791, KJ634273, KJ579442, KJ579441, KJ680135, KJ680134, KF383121, KF383120, KF383119, KF383118, KF383117, KF383116, KF383115, KF383114, KF383113, KF383112, KF383111, KF383110, KF383109, KF383108, KF383107, KF383106, KF383105, KF383104, KF383103, KF383102, KF383101, KF383100, KF383099, KF383098, KF383097, KF383096, KF383095, KF383094, KF383093, KF383092, KF383091, KF383090, KF383089, KF383088, KF383087, KF383086, KF383085, KF383084, KF383083, KF383082, KF383081, KF383080, KF383079, KF383078, KF383077, KF383076, KF383075, KF383074, KF383073, KF383072, KF383071, KF383070, KF383069, KF383068, KF383067, KF383066, KF383065, KF383064, KF383063, KF383062, KF383061, KF383060, KF383059, KF383058, KF383057, KF383056, KF383055, KF383054, KF383053, KF383053, KF383051, KF383050, KF383049, KF383048, KF383047, KF383046, KF383045, KF383044, KF383043, KF383042, KF383041, KF383040, KF383039, KF383038, KF383037, KF383036, KF383035, KF383034, KF383033, KF383032, KF383031, KF383030, KF383029, KF383028, KF383027, KF383026, KF383025, KF383024, KF383023, KF383022, KF383021, KF383020, KF383019, KF383018, KF383017, KF383016, KF383015, KF270887, KF270886, KF258813, JN860885, HQ234501, HQ234500, HQ234499, HQ234498, EU545988, KU681082, KU681081, KT200609, KU321639, KF268950, KF268949, KF268948, KP099610, KP099609, KM212967, KM212966, KM212965, KM212964, KM212963, KM212961, AB908162, AF013415, EU303241, AY632535, AF372422, EU074027, DQ859059, AY326412, and YP_002790881; all of which sequences (as entered by the date of filing of this application) are herein incorporated by reference. See also Berthet et al. (2014) Vector Borne Zoonotic Dis. 14(12):862-865, Faye et al. (2014) PLoS Negl. Trop. Dis. 8(1):e2636, Zanluca et al. (2015) Mem. Inst. Oswaldo Cruz. 110(4):569-572, Grard et al. (2014) PLoS Negl. Trop. Dis. 8(2):e2681, and Haddow et al. (2012) PLoS Negl. Trop. Dis. 6(2):e1477 for sequence comparisons and a discussion of genetic diversity and phylogenetic analysis of Zika viruses.

A dengue virus polynucleotide, oligonucleotide, nucleic acid and nucleic acid molecule, as defined above, is a nucleic acid molecule derived from a dengue virus, including, without limitation, any of the various dengue virus serotypes 1-4. The molecule need not be physically derived from the particular isolate in question, but may be synthetically or recombinantly produced.

Nucleic acid sequences for a number of dengue virus isolates are known. Representative dengue virus sequences, including sequences of the 5'-untranslated region (UTR) and coding region for the capsid protein C from dengue virus isolates are listed in the National Center for Biotechnology Information (NCBI) database. See, for example, NCBI entries: Accession No. NC_001477, Accession No. NC_001474, Accession No. NC_001475, Accession No. NC_002640, Accession No. AB609588, Accession No. EU848545, Accession No. AB609589, Accession No. AF038403, Accession No. AF038402, Accession No. M29095, Accession No. M93130, Accession No. AB609590, Accession No. AB609591, Accession No. 566064, Accession No. AY947539, Accession No. JN559741, Accession No. JN559740, Accession No. JF357906, Accession No. HQ634199, Accession No. HQ541794, Accession No. EU076567, Accession No. EU076565, Accession No. EU076563, Accession No. EU076561, Accession No. JQ950328, Accession No. JN796245, Accession No. JN819424, Accession No. JN819422, Accession No. JN819414, Accession No. JN819412, Accession No. JN819406, Accession No. JN819417, Accession No. JN819415, Accession No. JN819409, Accession No. JN093514, Accession No. JF730055, Accession No. JN000937, Accession No. JF937647, Accession No. JN819406, Accession No. GQ868543; all of which sequences (as entered by the date of filing of this application) are herein incorporated by reference. See also Weaver et al. (2009) Infect. Genet. Evol. 9(4):523-540 and Rico-Hesse (2003) Adv. Virus Res. 59:315-341 for sequence comparisons and a discussion of genetic diversity and phylogenetic analysis of dengue viruses.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

As used herein, a "solid support" refers to a solid surface such as a magnetic bead, latex bead, microtiter plate well, glass plate, nylon, agarose, acrylamide, and the like.

As used herein, the term "target nucleic acid region" or "target nucleic acid" denotes a nucleic acid molecule with a "target sequence" to be amplified. The target nucleic acid may be either single-stranded or double-stranded and may include other sequences besides the target sequence, which may not be amplified. The term "target sequence" refers to the particular nucleotide sequence of the target nucleic acid which is to be amplified. The target sequence may include a probe-hybridizing region contained within the target molecule with which a probe will form a stable hybrid under desired conditions. The "target sequence" may also include the complexing sequences to which the oligonucleotide primers complex and extended using the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands (or sense and anti-sense strands).

The term "primer" or "oligonucleotide primer" as used herein, refers to an oligonucleotide that hybridizes to the template strand of a nucleic acid and initiates synthesis of a nucleic acid strand complementary to the template strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is preferably single-stranded for maximum efficiency in amplification, but may alternatively be double-stranded. If double-stranded, the primer can first be treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA or RNA synthesis. Typically, viral nucleic acids are amplified using at least one set of oligonucleotide primers comprising at least one forward primer and at least one reverse primer capable of hybridizing to regions of a viral nucleic acid flanking the portion of the viral nucleic acid to be amplified. A forward primer for amplifying chikungunya virus is complementary to the 3' end of the anti-genomic chikungunya virus template produced during replication or amplification of chikungunya virus nucleic acids. A reverse primer for amplifying chikungunya virus is complementary to the 3' end of the chikungunya virus positive sense genomic RNA strand. A forward primer for amplifying Zika virus is complementary to the 3' end of the anti-genomic Zika virus template produced during replication or amplification of Zika virus nucleic acids. A reverse primer for amplifying Zika virus is complementary to the 3' end of the Zika virus positive sense genomic RNA strand.

The term "amplicon" refers to the amplified nucleic acid product of a PCR reaction or other nucleic acid amplification process (e.g., ligase chain reaction (LGR), nucleic acid sequence based amplification (NASBA), transcription-mediated amplification (TMA), Q-beta amplification, strand displacement amplification, or target mediated amplification). Amplicons may comprise RNA or DNA depending on the technique used for amplification. For example, DNA amplicons may be generated by RT-PCR, whereas RNA amplicons may be generated by TMA/NASBA.

As used herein, the term "probe" or "oligonucleotide probe" refers to a polynucleotide, as defined above, that contains a nucleic acid sequence complementary to a nucleic acid sequence present in the target nucleic acid analyte. The polynucleotide regions of probes may be composed of DNA, and/or RNA, and/or synthetic nucleotide analogs. Probes may be labeled in order to detect the target sequence. Such a label may be present at the 5' end, at the 3' end, at both the 5' and 3' ends, and/or internally. The "oligonucleotide probe" may contain at least one fluorescer and at least one quencher. Quenching of fluorophore fluorescence may be eliminated by exonuclease cleavage of the fluorophore from the oligonucleotide (e.g., TaqMan assay) or by hybridization of the oligonucleotide probe to the nucleic acid target sequence (e.g., molecular beacons). Additionally, the oligonucleotide probe will typically be derived from a sequence that lies between the sense and the antisense primers when used in a nucleic acid amplification assay.

As used herein, the term "capture oligonucleotide" refers to an oligonucleotide that contains a nucleic acid sequence complementary to a nucleic acid sequence present in the target nucleic acid analyte such that the capture oligonucleotide can "capture" the target nucleic acid. One or more capture oligonucleotides can be used in order to capture the target analyte. The polynucleotide regions of a capture oligonucleotide may be composed of DNA, and/or RNA, and/or synthetic nucleotide analogs. By "capture" is meant that the analyte can be separated from other components of the sample by virtue of the binding of the capture molecule to the analyte. Typically, the capture molecule is associated with a solid support, either directly or indirectly.

It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

As used herein, the term "binding pair" refers to first and second molecules that specifically bind to each other, such as complementary polynucleotide pairs capable of forming nucleic acid duplexes. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent. Unless the context clearly indicates otherwise, the terms "affinity molecule" and "target analyte" are used herein to refer to first and second members of a binding pair, respectively.

The terms "specific-binding molecule" and "affinity molecule" are used interchangeably herein and refer to a molecule that will selectively bind, through chemical or physical means to a detectable substance present in a sample. By "selectively bind" is meant that the molecule binds preferentially to the target of interest or binds with greater affinity to the target than to other molecules. For example, a DNA molecule will bind to a substantially complementary sequence and not to unrelated sequences. An oligonucleotide that "specifically binds" to a particular type of chikungunya virus, such as a particular genotype of chikungunya virus (e.g., West African, East/Central/South African (ECSA), or Asian (Indian or south east clade) genotype), denotes an oligonucleotide, e.g., a primer, probe or a capture oligonucleotide, that binds to the particular chikungunya virus genotype, but does not bind to a sequence from other types of chikungunya viruses. An oligonucleotide that "specifically binds" to a particular type of Zika virus, such as a particular genotype of Zika virus, denotes an oligonucleotide, e.g., a primer, probe or a capture oligonucleotide, that binds to the particular Zika virus genotype, but does not bind to a sequence from other types of Zika viruses.

The terms "selectively detects" or "selectively detecting" refer to the detection of chikungunya virus, Zika virus, or dengue virus nucleic acids using oligonucleotides, e.g., primers, probes and/or capture oligonucleotides that are capable of detecting a particular viral nucleic acid, for example, by amplifying and/or binding to at least a portion of an RNA segment from a particular type of virus, such as a particular virus genotype, but do not amplify and/or bind to sequences from other types of viruses under appropriate hybridization conditions.

The "melting temperature" or "Tm" of double-stranded DNA is defined as the temperature at which half of the helical structure of DNA is lost due to heating or other dissociation of the hydrogen bonding between base pairs, for example, by acid or alkali treatment, or the like. The $T_m$ of a DNA molecule depends on its length and on its base composition. DNA molecules rich in GC base pairs have a higher $T_m$ than those having an abundance of AT base pairs. Separated complementary strands of DNA spontaneously reassociate or anneal to form duplex DNA when the temperature is lowered below the $T_m$. The highest rate of nucleic acid hybridization occurs approximately 25 degrees C. below the $T_m$. The $T_m$ may be estimated using the following relationship: $T_m=69.3+0.41(GC)\%$ (Marmur et al. (1962) *J. Mol. Biol.* 5:109-118).

As used herein, a "biological sample" refers to a sample of cells, tissue, or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, cells (e.g., epithelial and endothelial cells, fibroblasts, and macrophages), muscles, joints, organs (e.g., liver, lung, spleen, thymus, kidney, brain, or lymph node), biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, semiconductor nanoparticles, dyes, metal ions, metal sols, ligands (e.g., biotin, strepavidin or haptens) and the like. The term "fluorescer" refers to a substance or a portion thereof which is capable of exhibiting fluorescence in the detectable range. Particular examples of labels which may be used in the practice of the invention include, but are not limited to, SYBR green, SYBR gold, a CAL Fluor dye such as CAL Fluor Gold 540, CAL Fluor Orange 560, CAL Fluor Red 590, CAL Fluor Red 610, and CAL Fluor Red 635, a Quasar dye such as Quasar 570, Quasar 670, and Quasar 705, an Alexa Fluor such as Alexa Fluor 350, Alexa Fluor 488, Alexa Fluor 546, Alexa Fluor 555, Alexa Fluor 594, Alexa Fluor 647,and Alexa Fluor 784, a cyanine dye such as Cy 3, Cy3.5, Cy5, Cy5.5, and Cy7, fluorescein, 2', 4', 5', 7'-tetrachloro-4-7-di chlorofluorescein (TET), carboxyfluorescein (FAM), 6-carboxy-4',5'-dichloro-2',7'-dimethoxyfluorescein (JOE), hexachlorofluorescein (HEX), rhodamine, carboxy-X-rhodamine (ROX), tetramethyl rhodamine (TAMRA), FITC, dansyl, umbelliferone, dimethyl acridinium ester (DMAE), Texas red, luminol, NADPH, horseradish peroxidase (HRP), and α-β-galactosidase.

A "molecular beacon" probe is a single-stranded oligonucleotide, typically 25 to 40 bases-long, in which the bases on the 3' and 5' ends are complementary forming a "stem," typically for 5 to 8 base pairs. A molecular beacon probe forms a hairpin structure at temperatures at and below those used to anneal the primers to the template (typically below about 60° C.). The double-helical stem of the hairpin brings a fluorophore (or other label) attached to the 5' end of the probe in proximity to a quencher attached to the 3' end of the probe. The probe does not fluoresce (or otherwise provide a signal) in this conformation. If a probe is heated above the temperature needed to melt the double stranded stem apart, or the probe hybridizes to a target nucleic acid that is complementary to the sequence within the single-strand loop of the probe, the fluorophore and the quencher are separated, and the fluorophore fluoresces in the resulting conformation. Therefore, in a series of PCR cycles the strength of the fluorescent signal increases in proportion to the amount of the molecular beacon that is hybridized to the amplicon, when the signal is read at the annealing temperature. Molecular beacons of high specificity, having different loop sequences and conjugated to different fluorophores, can be selected in order to monitor increases in amplicons that differ by as little as one base (Tyagi, S. and Kramer, F. R. (1996), Nat. Biotech. 14:303 308; Tyagi, S. et al., (1998), Nat. Biotech. 16: 49 53; Kostrikis, L. G. et al., (1998), Science 279: 1228 1229; all of which are herein incorporated by reference).

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; birds; and laboratory animals, including rodents such as mice, rats and guinea pigs, and the like. The term does not denote a particular age. Thus, both adult and newborn individuals are intended to be covered.

2. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of reagents and methods for diagnosing infection caused by chikungunya and Zika viruses. In particular, the invention provides quantitative assays that can detect all lineages of chikungunya virus and Zika virus and distinguish chikungunya virus and Zika virus from each other as well as dengue virus and other arbovirus pathogens.

The methods are useful for detecting chikungunya and Zika viruses in biological samples such as blood samples, including without limitation, in whole blood, serum and plasma. Thus, the methods can be used to diagnose chikungunya virus or Zika virus infection in a subject, as well as to detect chikungunya virus or Zika virus contamination in donated blood samples. Aliquots from individual donated samples or pooled samples can be screened for the presence of chikungunya virus or Zika virus and those samples or pooled samples contaminated with chikungunya virus or Zika virus can be eliminated before they are combined. In this way, a blood supply substantially free of chikungunya virus or Zika virus contamination can be provided.

Chikungunya and Zika viruses can also be detected in other bodily fluids, cells, or tissue samples in which the virus proliferates, including, but not limited to, saliva, cerebrospinal fluid (CSF), urine, amniotic fluid, dendritic cells, fibroblasts, keratinocytes, epithelial cells, endothelial cells, macrophages, and tissue samples obtained from the skin, liver, muscles, joints, spleen, lymph nodes, thymus, lung, brain, nerves, kidneys, or bone marrow. The, chikungunya and Zika viruses can be specifically detected even in samples containing other viruses and pathogens, such as dengue virus, West Nile virus, Japanese encephalitis virus, tick-borne encephalitis virus, yellow fever virus, Saint Louis encephalitis virus, o'nyong-nyong virus, Semliki Forest virus, mayaro virus, Ross River virus, Getah virus, Barmah Forest virus, Una virus, hepatitis C virus (HCV), Leptospira, Plasmodium species, Rift Valley fever virus, and human immunodeficiency virus (HIV). Moreover, the methods described herein can be used to screen mosquitoes, primates, birds, cattle, rodents, and other hosts for chikungunya virus in order to determine if a particular insect or animal population is infected with the chikungunya virus, thereby preventing further transmission and spread of viral infection. Furthermore, the methods described herein can be used to screen mosquitoes, primates, rodents, and other hosts for Zika virus in order to determine if a particular insect or animal population is infected with the Zika virus, thereby preventing further transmission and spread of viral infection.

The methods use oligonucleotide reagents (e.g., oligonucleotide primers and probes) or a combination of reagents capable of detecting one or more pathogenic chikungunya and/or Zika viruses in a single assay. In one format, primer pairs and probes capable of detecting one or more pathogenic chikungunya or Zika viruses are used. For example, certain primers and probes are from "conserved" regions of chikungunya virus and therefore capable of detecting more than one pathogenic chikungunya, such as any combination of two or more chikungunya viruses that are pathogenic in humans, for example, two or more genotypes of chikungunya (e.g., both chikungunya West African and ECSA; West African and Asian; Asian and ECSA; or West African, Asian, and ECSA).

By way of example, the NSP2 gene of chikungunya virus includes conserved regions. Thus, primers and probes comprising sequences from these conserved regions, or the corresponding regions in other pathogenic chikungunya viruses, may be useful in detecting multiple pathogenic chikungunya viruses.

Other primers and probes are highly selective for a particular chikungunya virus, selectively amplifying, detecting and/or binding to a particular RNA segment from one of the virus genotypes. These highly selective primers and probes can be used alone or in combination to detect one or more viruses in a single assay.

Thus, there are a number of assay designs that can be used to detect human pathogenic viral genotypes alone or in combination with each other. In one embodiment, "conserved" primers (i.e., those primers that amplify more than one chikungunya virus) can be used to detect one or more of the chikungunya virus genotypes, as specified above. For example, conserved primers and probes can be used to amplify and detect multiple viral genotypes. Alternatively, genotype-specific primers and probe(s) can be used to achieve specificity. For example, a single pathogenic genotype (e.g., West African, Asian, or ECSA strain) can be amplified with genotype-specific primers and detected with the corresponding genotype-specific probes. One or more genotypes can be amplified and detected simultaneously by using a combination of genotype-specific primers and probes in a multiplex-type assay format.

Thus, the probes and primers may be designed from conserved nucleotide regions of the polynucleotides of interest or from non-conserved nucleotide regions of the polynucleotide of interest. Generally, nucleic acid probes are developed from non-conserved or unique regions when maximum specificity is desired, and nucleic acid probes are developed from conserved regions when assaying for nucleotide regions that are closely related to, for example, different chikungunya virus isolates.

Oligonucleotides for use in the assays described herein can be derived, for example, from the NSP2 gene sequences of chikungunya viruses. Representative sequences from chikungunya isolates are listed herein. Thus, primers and probes for use in detection of chikungunya virus include those derived from any one of the chikungunya West African, East/Central/South African (ECSA), and Asian (Indian and south east clades) virus genotypes, including any pathogenic chikungunya virus strain or isolate.

Representative sequences for a number of chikungunya virus isolates are known. A representative chikungunya virus sequence is presented in SEQ ID NO:26 of the Sequence Listing. Additional representative sequences, including RNA genomic sequences and sequences of the non-structural polyprotein, the non-structural proteins (nsP1, nsP2, nsP3 and nsP4) produced by proteolytic processing of the non-structural polyprotein, the structural polyprotein, and the structural proteins (Capsid, E1, E2, E3, and 6K) produced by proteolytic processing of the structural polyprotein for virus isolates of various genotypes, including West African, East/Central/South African (ECSA), and Asian (Indian and south east clades) strains are listed in the National Center for Biotechnology Information (NCBI) database. See, for example, NCBI entries: Accession No. AF369024, NC_004162, AF490259, EF210157, JX088705, KR559498, KR559497, KT449801, KM923920, KJ689453, KJ689452, KJ451624, KJ451623, KJ796852, KJ796851, KJ796847, KJ796846, KJ796844, KC488650, HM067743, GU189061, HM045823, HM045822, HM045821, HM045820, HM045819, HM045818, HM045817, HM045816, HM045815, HM045814, HM045813, HM045812, HM045811, HM045810, HM045809, HM045808, HM045807, HM045806, HM045805, HM045804, HM045803, HM045802, HM045801, HM045800, HM045799, HM045798, HM045797, HM045796, HM045795, HM045794, HM045793, HM045792, HM045791, HM045790, HM045789, HM045788, HM045787, HM045786, HM045785, HM045784, HQ456255, HQ456254, HQ456253, HQ456252, HQ456251, GQ905863, AY726732, FJ807899, FJ807898, FJ807897, FJ807896, GQ428215, EF452494, EF452493, FJ959103, EU244823, EF012359, DQ443544, KF151175, KF151174, KP003813, KP003812, KP003811, KP003810, KP003809, KP003808, KP003807, KF872195, HE806461, HM067744, HQ848081, HQ848080, JQ067624, GU199353, GU199352, GU199351, GU199350, FJ807895, FJ807894, FJ807893, FJ807892, FJ807891, FJ807890, FJ807887, EU703762, EU703761, EU703760, EU703759, L37661, AB455494, AB455493, EU564335, EU564334, EF027141, EF027140, EF027139, EF027138, EF027137, EF027136, EF027135, EF027134, AY424803, AF339485, EU192143, EU192142, NC_004162, EU037962, KJ941050, KF151178, KF151177, KF151176, and AB678695; all of which sequences (as entered by the date of filing of this application) are herein incorporated by reference. See also Lo Presti et al. (2014) Asian Pac. J. Trop. Med. 7(12):925-932, Weaver et al. (2015) Antiviral Res. 120:32-39 and Caglioti et al. (2013) New Microbiol. 36(3): 211-227 for sequence comparisons and a discussion of genetic diversity and phylogenetic analysis of chikungunya viruses.

The methods also use oligonucleotide reagents (e.g., oligonucleotide primers and probes) or a combination of reagents capable of detecting one or more pathogenic Zika viruses in a single assay. In one format, primer pairs and probes capable of detecting one or more pathogenic Zika viruses are used. For example, certain primers and probes are from "conserved" regions of Zika virus and therefore capable of detecting more than one pathogenic Zika virus, such as any combination of two or more Zika viruses that are pathogenic in humans, for example, two or more genotypes of Zika virus (e.g., both African and Asian, African and Caribbean, or African, Asian and Central/South American).

By way of example, the region of the Zika virus genome from nucleotide position 7332 to 7432, numbered relative to the reference sequence of SEQ ID NO:32 of Zika virus strain MR766-NIID (GenBank: LC002520.1), includes conserved regions. Thus, primers and probes comprising sequences from these conserved regions, or the corresponding regions in other pathogenic Zika viruses, may be useful in detecting multiple pathogenic Zika viruses.

Other primers and probes are highly selective for a particular Zika virus, selectively amplifying, detecting and/or binding to a particular RNA segment from one of the virus genotypes. These highly selective primers and probes can be used alone or in combination to detect one or more viruses in a single assay.

Thus, there are a number of assay designs that can be used to detect human pathogenic viral genotypes alone or in combination with each other. In one embodiment, "conserved" primers (i.e., those primers that amplify more than one Zika virus) can be used to detect one or more of the Zika virus genotypes, as specified above. For example, conserved primers and probes can be used to amplify and detect multiple viral genotypes. Alternatively, genotype-specific primers and probe(s) can be used to achieve specificity. For example, a single pathogenic genotype (e.g., African, Asian, Caribbean, Pacific island, or Central/South American strain) can be amplified with genotype-specific primers and detected with the corresponding genotype-specific probes. One or more genotypes can be amplified and detected simultaneously by using a combination of genotype-specific primers and probes in a multiplex-type assay format.

Thus, the probes and primers may be designed from conserved nucleotide regions of the polynucleotides of interest or from non-conserved nucleotide regions of the polynucleotide of interest. Generally, nucleic acid probes are developed from non-conserved or unique regions when maximum specificity is desired, and nucleic acid probes are developed from conserved regions when assaying for nucleotide regions that are closely related in different Zika virus isolates.

Oligonucleotides for use in the assays described herein can be derived, for example, from gene sequences of Zika viruses. Representative sequences from Zika virus isolates are listed herein. Thus, primers and probes for use in detection of Zika virus include those derived from any Zika virus genotype, including any pathogenic Zika virus strain or isolate, including strains from Africa, Asia, Central and South America, the Caribbean, and Pacific islands.

Representative sequences for a number of Zika virus isolates are known. Representative Zika virus sequences are presented in SEQ ID NO:31 and SEQ ID NO:32 of the Sequence Listing. Additional representative sequences, including RNA genomic sequences and sequences of the polyprotein and the non-structural proteins (NS1, NS2A, NS2B, NS3, NS4A, NS4B, and NS5) and the structural proteins (capsid protein (C), precursor membrane protein (prM), and envelope protein (E)) produced by proteolytic processing of the polyprotein for virus isolates of various strains are listed in the National Center for Biotechnology Information (NCBI) database. See, for example, NCBI entries: Accession No. NC_012532, KU647676, KU556802, KU509998, KU646828, KU646827, KU501217, KU501216, KU501215, KU365780, KU365779, KU365778, KU365777, KU312315, KU312314, KU312313, KU312312, KM078979, KM078978, KM078977, KM078976, KM078975, KM078974, KM078973, KM078972, KM078971, KM078970, KM078969, KM078968, KM078967, KM078966, KM078965, KM078964, KM078963, KM078962, KM078961, KM078960, KM078959, KM078958, KM078957, KM078956, KM078955, KM078954, KM078953, KM078952, KM078951, KM078950, KM078949, KM078948, KM078947, KM078946, KM078945, KM078944, KM078943, KM078942, KM078941, KM078940, KM078939, KM078938, KM078937, KM078936, KM078935, KM078934, KM078933, KM078932, KM078931, KM078930, KM078929, KR816336, KR816335, KR816334, KR816333, KM851039, KR815990, KR815989, KM851038, KM014700, KJ873161, KJ873160, KF993678, LC002520, KJ461621, KJ776791, KJ634273, KJ579442, KJ579441, KJ680135, KJ680134, KF383121, KF383120, KF383119, KF383118, KF383117, KF383116, KF383115, KF383114, KF383113, KF383112, KF383111, KF383110, KF383109, KF383108, KF383107, KF383106, KF383105, KF383104, KF383103, KF383102, KF383101, KF383100, KF383099, KF383098, KF383097, KF383096, KF383095, KF383094, KF383093, KF383092, KF383091, KF383090, KF383089, KF383088, KF383087, KF383086, KF383085, KF383084, KF383083, KF383082, KF383081, KF383080, KF383079, KF383078, KF383077, KF383076, KF383075, KF383074, KF383073, KF383072, KF383071, KF383070, KF383069, KF383068, KF383067, KF383066, KF383065, KF383064, KF383063, KF383062, KF383061, KF383060, KF383059, KF383058, KF383057, KF383056, KF383055, KF383054, KF383053, KF383053, KF383051, KF383050, KF383049, KF383048, KF383047, KF383046, KF383045, KF383044, KF383043, KF383042, KF383041, KF383040, KF383039, KF383038, KF383037, KF383036, KF383035, KF383034, KF383033, KF383032, KF383031, KF383030, KF383029, KF383028, KF383027, KF383026, KF383025, KF383024, KF383023, KF383022, KF383021, KF383020, KF383019, KF383018, KF383017, KF383016, KF383015, KF270887, KF270886, KF258813, JN860885, HQ234501, HQ234500, HQ234499, HQ234498, EU545988, KU681082, KU681081, KT200609, KU321639, KF268950, KF268949, KF268948, KP099610, KP099609, KM212967, KM212966, KM212965, KM212964, KM212963, KM212961, AB908162, AF013415, EU303241, AY632535, AF372422, EU074027, DQ859059, AY326412, and YP_002790881; all of which sequences (as entered by the date of filing of this application) are herein incorporated by reference. See also Berthet et al. (2014) Vector Borne Zoonotic Dis. 14(12):862-865, Faye et al. (2014) PLoS Negl. Trop. Dis. 8(1):e2636, Zanluca et al. (2015) Mem. Inst. Oswaldo Cruz. 110(4):569-572, Grard et al. (2014) PLoS Negl. Trop. Dis. 8(2):e2681, and Haddow et al. (2012) PLoS Negl. Trop. Dis. 6(2):e1477 for sequence comparisons and a discussion of genetic diversity and phylogenetic analysis of Zika viruses.

Primers and probes for use in the assays herein are derived from these sequences and are readily synthesized by standard techniques, e.g., solid phase synthesis via phosphoramidite chemistry, as disclosed in U.S. Pat. Nos. 4,458,066 and 4,415,732, incorporated herein by reference; Beaucage et al., *Tetrahedron* (1992) 48:2223-2311; and Applied Biosystems User Bulletin No. 13 (1 Apr. 1987). Other chemical synthesis methods include, for example, the phosphotriester method described by Narang et al., *Meth. Enzymol.* (1979) 68:90 and the phosphodiester method disclosed by Brown et al., *Meth. Enzymol.* (1979) 68:109. Poly(A) or poly(C), or other non-complementary nucleotide extensions may be incorporated into oligonucleotides using these same methods. Hexaethylene oxide extensions may be coupled to the oligonucleotides by methods known in the art. Cload et al., *J. Am. Chem. Soc.* (1991) 113:6324-6326; U.S. Pat. No. 4,914,210 to Levenson et al.; Durand et al., *Nucleic Acids Res.* (1990) 18:6353-6359; and Horn et al., *Tet. Lett.* (1986) 27:4705-4708.

Additionally, nucleic acids can be obtained directly from the chikungunya or Zika virus in question. For example, the chikungunya virus is available from the ATCC (ATCC Accession No. VR-64, chikungunya virus from serum of patient from Tanganyika, East Africa, 1953). The Zika virus is available from the ATCC (ATCC Accession No. VR-84, Zika virus strain MR 766 from the blood of an experimental forest sentinel rhesus monkey, Uganda, 1947).

Alternatively, chikungunya virus can be isolated from infected mosquitos or animals. Once obtained, the virus can be propagated using known techniques (see, e.g., Buckley et al. (1975) Acta Virol. 19(1):10-18). Generally, chikungunya viruses are grown in cell culture. For example, *A. albopictus* and *A. aegypti mosquito* cell lines can be used for isolation of chikungunya virus (see, e.g., Sudeep et al. (2009) In Vitro Cell Dev. Biol. Anim. 45(9):491-495, Lee et al. (2015) PLoS Negl. Trop. Dis. 9(3):e0003544). Alternatively, several mammalian cell lines, such as human embryonic lung (HEL) cells, African green monkey kidney (VERO) cells, or baby hamster kidney (BHK-21) cells, may also be used (see, e.g., Pyndiah et al. (2012) Med. Trop. 72 Spec No:63-65, Davis et al. (1971) Appl. Microbiol. 21(2):338-341). In addition, virus may be obtained from inoculated animals susceptible to infection (e.g., monkeys, birds, cattle, and rodents).

Zika virus can be isolated from infected mosquitos (e.g., *Ae. africanus, Ae. apicoargenteus, Ae. luteocephalus, Ae. aegypti, Ae vitattus,* and *Ae. furcifer*). Once obtained, the virus can be propagated using known techniques (see, e.g., Way et al. (1976) J. Gen. Virol. 30(1):123-130, Wong et al. (2013) PLoS Negl Trop Dis. 7(8):e2348, and Li et al. (2012) PLoS Negl Trop Dis. 6(8):e1792; herein incorporated by reference in their entireties). For example, *A. albopictus* and *A. aegypti* mosquito cell lines can be used for isolation of Zika virus. Alternatively, mammalian cell lines, such as the rhesus monkey kidney LLC-MK2 cell line can be used (Way et al., supra). In addition, virus may be obtained from inoculated animals susceptible to infection (e.g., primates and rodents).

An amplification method such as PCR or nucleic acid sequence based amplification (NASBA) can be used to amplify polynucleotides from either chikungunya virus or Zika virus genomic RNA or cDNA derived therefrom. Alternatively, polynucleotides can be synthesized in the laboratory, for example, using an automatic synthesizer.

Typically, the primer oligonucleotides are in the range of between 10-100 nucleotides in length, such as 15-60, 20-40 and so on, more typically in the range of between 20-40 nucleotides long, and any length between the stated ranges.

In certain embodiments, a chikungunya virus primer oligonucleotide comprises a sequence selected from the group consisting of SEQ ID NOS:1-3, 6, and 7; or a fragment thereof comprising at least about 6 contiguous nucleotides, preferably at least about 8 contiguous nucleotides, more preferably at least about 10-12 contiguous nucleotides, and even more preferably at least about 15-20 contiguous nucleotides; or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto. Changes to the nucleotide sequences of SEQ ID NOS: 1-3, 6, and 7 may be introduced corresponding to genetic variations in particular chikungunya virus strains. In certain embodiments, up to three nucleotide changes, including 1 nucleotide change, 2 nucleotide changes, or three nucleotide changes, may be made in a sequence selected from the group consisting of SEQ ID NOS: 1-3, 6, and 7, wherein the oligonucleotide primer is capable of hybridizing to and amplifying a particular chikungunya virus target nucleic acid.

In other embodiments, a Zika virus primer oligonucleotide comprises a sequence selected from the group consisting of SEQ ID NOS:27-29; or a fragment thereof comprising at least about 6 contiguous nucleotides, preferably at least about 8 contiguous nucleotides, more preferably at least about 10-12 contiguous nucleotides, and even more preferably at least about 15-22 contiguous nucleotides; or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto. Changes to the nucleotide sequences of SEQ ID NOS:27-29 may be introduced corresponding to genetic variations in particular Zika virus strains. In certain embodiments, up to three nucleotide changes, including 1 nucleotide change, 2 nucleotide changes, or three nucleotide changes, may be made in a sequence selected from the group consisting of SEQ ID NOS:27-29, wherein the oligonucleotide primer is capable of hybridizing to and amplifying a particular Zika virus target nucleic acid.

The typical probe oligonucleotide is in the range of between 10-100 nucleotides long, such as 10-60, 15-40, 18-30, and so on, and any length between the stated ranges. In certain embodiments, a chikungunya virus probe oligonucleotide comprises a sequence selected from the group consisting of SEQ ID NOS:4, 5, and 8; or a fragment thereof comprising at least about 6 contiguous nucleotides, preferably at least about 8 contiguous nucleotides, more preferably at least about 10-12 contiguous nucleotides, and even more preferably at least about 15-20 contiguous nucleotides; or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto. Changes to the nucleotide sequences of SEQ ID NOS: 4, 5, and 8 may be introduced corresponding to genetic variations in particular chikungunya virus strains. In certain embodiments, up to three nucleotide changes, including 1 nucleotide change, 2 nucleotide changes, or three nucleotide changes, may be made in a sequence selected from the group consisting of SEQ ID NOS: 4, 5, and 8, wherein the oligonucleotide probe is capable of hybridizing to and detecting a particular chikungunya virus target nucleic acid.

In other embodiments, a Zika virus probe oligonucleotide comprises a sequence selected from the group consisting of SEQ ID NO:30; or a fragment thereof comprising at least about 6 contiguous nucleotides, preferably at least about 8 contiguous nucleotides, more preferably at least about 10-12 contiguous nucleotides, and even more preferably at least about 15-21 contiguous nucleotides; or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto. Changes to the nucleotide sequences of SEQ ID NO:30 may be introduced corresponding to genetic variations in particular Zika virus strains. In certain embodiments, up to three nucleotide changes, including 1 nucleotide change, 2 nucleotide changes, or three nucleotide changes, may be made to the sequence of SEQ ID NO:30, wherein the oligonucleotide probe is capable of hybridizing to and detecting a particular Zika virus target nucleic acid.

Moreover, the oligonucleotides, particularly the probe oligonucleotides, may be coupled to labels for detection. There are several means known for derivatizing oligonucleotides with reactive functionalities which permit the addition of a label. For example, several approaches are available for biotinylating probes so that radioactive, fluorescent, chemiluminescent, enzymatic, or electron dense labels can be attached via avidin. See, e.g., Broken et al., *Nucl. Acids Res.* (1978) 5:363-384 which discloses the use of ferritin-avidin-biotin labels; and Chollet et al., *Nucl. Acids Res.* (1985) 13:1529-1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly, *Nucl. Acids Res.* (1987) 15:3131-3139, Gibson et al. *Nucl. Acids Res.* (1987) 15:6455-6467 and U.S. Pat. No. 4,605,735 to Miyoshi et al. Methods are also available for synthesizing sulfhydryl-derivatized oligonucleotides, which can be reacted with thiol-specific labels, see, e.g., U.S. Pat. No. 4,757,141 to Fung et al., Connolly et al., *Nucl. Acids Res.* (1985) 13:4485-4502 and Spoat et al. *Nucl. Acids Res.* (1987) 15:4837-4848. A comprehensive review of methodologies for labeling DNA fragments is provided in Matthews et al., *Anal. Biochem.* (1988) 169:1-25.

For example, oligonucleotides may be fluorescently labeled by linking a fluorescent molecule to the non-ligating terminus of the molecule. Guidance for selecting appropriate fluorescent labels can be found in Smith et al., *Meth. Enzymol.* (1987) 155:260-301; Karger et al., *Nucl. Acids Res.* (1991) 19:4955-4962; Guo et al. (2012) Anal. Bioanal. Chem. 402(10):3115-3125; and *Molecular Probes Handbook, A Guide to Fluorescent Probes and Labeling Technologies,* $11^{th}$ edition, Johnson and Spence eds., 2010 (Molecular Probes/Life Technologies). Fluorescent labels include fluorescein and derivatives thereof, such as disclosed in U.S. Pat. No. 4,318,846 and Lee et al., *Cytometry* (1989) 10:151-164. Dyes for use in the present invention include 3-phenyl-7-isocyanatocoumarin, acridines, such as 9-i sothiocyanatoacridine and acridine orange, pyrenes, benzoxadiazoles, and stilbenes, such as disclosed in U.S. Pat. No. 4,174,384. Additional dyes include SYBR green, SYBR gold, Yakima Yellow, Texas Red, 3-(ε-carboxypentyl)-3'-ethyl-5,5'-dimethyloxa-carbocyanine (CYA); 6-carboxy fluorescein (FAM); CAL Fluor Orange 560, CAL Fluor Red 610, Quasar Blue 670; 5,6-carboxyrhodamine-110 (R110); 6-carboxyrhodamine-6G (R6G); N',N',N',N'-tetramethyl-6-carboxyrhodamine (TAMRA); 6-carboxy-X-rhodamine (ROX); 2', 4', 5', 7', -tetrachloro-4-7-dichlorofluorescein (TET); 2', 7'-dimethoxy-4', 5'-6 carboxyrhodamine (JOE); 6-carboxy-2',4,4',5',7,7'-hexachlorofluorescein (HEX); Dragonfly orange; ATTO-Tec; Bodipy; ALEXA; VIC, Cy3, and Cy5. These dyes are commercially available from various suppliers such as Life Technologies (Carlsbad, Calif.), Biosearch Technologies (Novato, Calif.), and Integrated DNA Technolgies (Coralville, Iowa). Fluorescent labels include fluorescein and derivatives thereof, such as disclosed in U.S. Pat. No. 4,318,846 and Lee et al., *Cytometry* (1989) 10:151-164, and 6-FAM, JOE, TAMRA, ROX, HEX-1, HEX-2, ZOE, TET-1 or NAN-2, and the like.

Oligonucleotides can also be labeled with a minor groove binding (MGB) molecule, such as disclosed in U.S. Pat. Nos. 6,884,584, 5,801,155; Afonina et al. (2002) Biotechniques 32:940-944, 946-949; Lopez-Andreo et al. (2005) Anal. Biochem. 339:73-82; and Belousov et al. (2004) Hum Genomics 1:209-217. Oligonucleotides having a covalently attached MGB are more sequence specific for their complementary targets than unmodified oligonucleotides. In addition, an MGB group increases hybrid stability with complementary DNA target strands compared to unmodified oligonucleotides, allowing hybridization with shorter oligonucleotides.

Additionally, oligonucleotides can be labeled with an acridinium ester (AE) using the techniques described below. Current technologies allow the AE label to be placed at any location within the probe. See, e.g., Nelson et al., (1995) "Detection of Acridinium Esters by Chemiluminescence" in *Nonisotopic Probing, Blotting and Sequencing*, Kricka L. J. (ed) Academic Press, San Diego, Calif.; Nelson et al. (1994) "Application of the Hybridization Protection Assay (HPA) to PCR" in *The Polymerase Chain Reaction*, Mullis et al. (eds.) Birkhauser, Boston, Mass.; Weeks et al., *Clin. Chem.* (1983) 29:1474-1479; Berry et al., *Clin. Chem.* (1988) 34:2087-2090. An AE molecule can be directly attached to the probe using non-nucleotide-based linker arm chemistry that allows placement of the label at any location within the probe. See, e.g., U.S. Pat. Nos. 5,585,481 and 5,185,439.

In certain embodiments, molecular beacon probes may be used for detection of viral target nucleic acids. Molecular beacons are hairpin shaped oligonucleotides with an internally quenched fluorophore. Molecular beacons typically comprise four parts: a loop of about 18-30 nucleotides, which is complementary to the target nucleic acid sequence; a stem formed by two oligonucleotide regions that are complementary to each other, each about 5 to 7 nucleotide residues in length, on either side of the loop; a fluorophore covalently attached to the 5' end of the molecular beacon, and a quencher covalently attached to the 3' end of the molecular beacon. When the beacon is in its closed hairpin conformation, the quencher resides in proximity to the fluorophore, which results in quenching of the fluorescent emission from the fluorophore. In the presence of a target nucleic acid having a region that is complementary to the strand in the molecular beacon loop, hybridization occurs resulting in the formation of a duplex between the target nucleic acid and the molecular beacon. Hybridization disrupts intramolecular interactions in the stem of the molecular beacon and causes the fluorophore and the quencher of the molecular beacon to separate resulting in a fluorescent signal from the fluorophore that indicates the presence of the target nucleic acid sequence. See, e.g., Guo et al. (2012) Anal. Bioanal. Chem. 402(10):3115-3125; Wang et al. (2009) Angew. Chem. Int. Ed. Engl. 48(5):856-870; and Li et al. (2008) Biochem. Biophys. Res. Commun. 373(4):457-461; herein incorporated by reference in their entireties.

Representative chikungunya virus primers and probes derived from conserved regions of the NSP2 gene for use in the various assays are shown in Example 1 in Table 1. These oligonucleotide primers and probes are designed to detect all genotypes of chikungunya virus. Furthermore, these chikungunya virus primers and probes can be used in combination with primers and probes designed for detecting other pathogens in multiplex assays. For example, oligonucleotide primers and probes useful for detecting dengue virus, including serotypes 1-4, are shown in Example 1 in Tables 4 and 5 (see also Waggoner et al. (2013) J. Clin. Microbiol. 51:2172-2181 and International Application Publication No. WO 2014/055746A1; herein incorporated by reference in their entireties). These chikungunya virus primers and probes can be combined with the dengue virus and/or Zika virus primers and probes described herein to allow chikungunya virus to be detected simultaneously with dengue virus and/or Zika virus in a single multiplex assay.

Representative Zika virus primers and probes derived from conserved regions of the Zika viral genome for use in the various assays are shown in Example 2 in Table 6. These oligonucleotide primers and probes are designed to detect all genotypes of Zika virus. Furthermore, these Zika virus primers and probes can be used in combination with primers and probes designed for detecting other pathogens in multiplex assays. For example, chikungunya virus and/or dengue virus primers and probes can be combined with the Zika virus primers and probes described herein to allow Zika virus to be detected simultaneously with chikungunya virus and/or dengue virus in a single multiplex assay.

It is to be understood that the primers and probes described herein are merely representative, and other oligonucleotides derived from various pathogenic chikungunya virus, Zika virus, or dengue virus strains or other arbovirus pathogens will find use in the assays described herein.

When utilizing a hybridization-based detection system, a nucleic acid probe is chosen that is complementary to a target nucleic acid sequence. By selection of appropriate conditions, the probe and the target sequence "selectively hybridize," or bind, to each other to form a hybrid molecule. An oligonucleotide that "selectively hybridizes" to a particular virus sequence from a particular viral genotype under hybridization conditions described below, denotes an oligonucleotide, e.g., a primer or probe oligonucleotide, that binds to the viral sequence of that particular virus genotype, but does not bind to a sequence from a virus of a different genotype.

In one embodiment of the present invention, a nucleic acid molecule is capable of hybridizing selectively to a target sequence under moderately stringent hybridization conditions. In the context of the present invention, moderately stringent hybridization conditions allow detection of a target nucleic acid sequence of at least 14 nucleotides in length having at least approximately 70% sequence identity with the sequence of the selected nucleic acid probe. In another embodiment, such selective hybridization is performed under stringent hybridization conditions. Stringent hybridization conditions allow detection of target nucleic acid sequences of at least 14 nucleotides in length having a sequence identity of greater than 90% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press). Hybrid molecules can be formed, for example, on a solid support, in solution, and in tissue sections. The formation of hybrids can be monitored by inclusion of a reporter molecule, typically, in the probe. Such reporter molecules or detectable labels include, but are not limited to, radioactive elements, fluorescent markers, and molecules to which an enzyme-conjugated ligand can bind.

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is well known (see, for example, Sambrook, et al., *Molecular Cloning: A Laboratory Manual*, 3rd Edition, 2001).

As explained above, the primers and probes may be used in polymerase chain reaction (PCR)-based techniques, such as RT-PCR, to detect chikungunya virus infection in biological samples. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) *PCR Protocols* (Academic Press, NY 1990); Taylor (1991) *Polymerase chain reaction: basic principles and automation*, in *PCR: A Practical Approach*, McPherson et al. (eds.) IRL Press, Oxford; Saiki et al. (1986) *Nature* 324:163; as well as in U.S. Pat. Nos. 4,683,195, 4,683,202 and 4,889,818, all incorporated herein by reference in their entireties.

In particular, PCR uses relatively short oligonucleotide primers which flank the target nucleotide sequence to be amplified, oriented such that their 3' ends face each other, each primer extending toward the other. The polynucleotide sample is extracted and denatured, preferably by heat, and hybridized with first and second primers that are present in molar excess. Polymerization is catalyzed in the presence of the four deoxyribonucleotide triphosphates (dNTPs—dATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands. The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grows exponentially with each cycle. Preferably, PCR is carried out with a commercially available thermal cycler, e.g., Perkin Elmer.

RNAs may be amplified by reverse transcribing the RNA into cDNA, and then performing PCR (RT-PCR), as described above. Alternatively, a single enzyme may be used for both steps as described in U.S. Pat. No. 5,322,770, incorporated herein by reference in its entirety. RNA may also be reverse transcribed into cDNA, followed by asymmetric gap ligase chain reaction (RT-AGLCR) as described by Marshall et al. (1994) *PCR Meth. App.* 4:80-84.

Nucleic acid sequence based amplification (NASBA) is an isothermal RNA-specific amplification method that does not require thermal cycling instrumentation. RNA is initially reverse transcribed such that the single-stranded RNA target is copied into a double-stranded DNA molecule that serves as a template for RNA transcription. Detection of the amplified RNA is typically accomplished either by electrochemiluminescence or in real-time, for example, with fluorescently labeled molecular beacon probes. See, e.g., Lau et al. (2006) *Dev. Biol.* (Basel) 126:7-15; and Deiman et al. (2002) *Mol. Biotechnol.* 20(2):163-179.

The Ligase Chain Reaction (LCR) is an alternate method for nucleic acid amplification. In LCR, probe pairs are used which include two primary (first and second) and two secondary (third and fourth) probes, all of which are employed in molar excess to the target. The first probe hybridizes to a first segment of the target strand, and the second probe hybridizes to a second segment of the target strand, the first and second segments being contiguous so that the primary probes abut one another in 5' phosphate-3' hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. If the target is initially double stranded, the secondary probes also will hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved. This technique is described more completely in EPA 320,308 to K. Backman published Jun. 16, 1989 and EPA 439,182 to K. Backman et al., published Jul. 31, 1991, both of which are incorporated herein by reference.

Other known methods for amplification of nucleic acids include, but are not limited to self-sustained sequence replication (3SR) described by Guatelli et al., *Proc. Natl. Acad. Sci. USA* (1990) 87:1874-1878 and J. Compton, *Nature* (1991) 350:91-92 (1991); Q-beta amplification; strand displacement amplification (as described in Walker et al., *Clin. Chem.* (1996) 42:9-13 and EPA 684,315; target mediated amplification, as described in International Publication No. WO 93/22461, and the TaqMan™ assay.

The fluorogenic 5' nuclease assay, known as the TaqMan™ assay (Perkin-Elmer), is a powerful and versatile PCR-based detection system for nucleic acid targets. Primers and probes derived from conserved and/or non-conserved regions of the dengue virus genome in question can be used in TaqMan™ analyses to detect the presence of infection in a biological sample. Analysis is performed in conjunction with thermal cycling by monitoring the generation of fluorescence signals. The assay system dispenses with the need for gel electrophoretic analysis, and is capable of generating quantitative data allowing the determination of target copy numbers. For example, standard curves can be produced using serial dilutions of previously quantified dengue viral suspensions. A standard graph can be produced with copy numbers of each of the panel members against which sample unknowns can be compared.

The fluorogenic 5' nuclease assay is conveniently performed using, for example, AmpliTaq Gold™ DNA polymerase, which has endogenous 5' nuclease activity, to digest an internal oligonucleotide probe labeled with both a fluorescent reporter dye and a quencher (see, Holland et al., *Proc. Natl. Acad.Sci. USA* (1991) 88:7276-7280; and Lee et al., *Nucl. Acids Res*. (1993) 21:3761-3766). Assay results are detected by measuring changes in fluorescence that occur during the amplification cycle as the fluorescent probe is digested, uncoupling the dye and quencher labels and causing an increase in the fluorescent signal that is proportional to the amplification of target nucleic acid.

The amplification products can be detected in solution or using solid supports. In this method, the TaqMan™ probe is designed to hybridize to a target sequence within the desired PCR product. The 5' end of the TaqMan™ probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence that can be detected.

For a detailed description of the TaqMan™ assay, reagents and conditions for use therein, see, e.g., Holland et al., *Proc. Natl. Acad. Sci, U.S.A*. (1991) 88:7276-7280; U.S. Pat. Nos. 5,538,848, 5,723,591, and 5,876,930, all incorporated herein by reference in their entireties.

A class of quenchers, known as "Black Hole Quenchers" such as BHQ1 and BHQ2, can be used in the nucleic acid assays described above. These quenchers reduce background and improve signal to noise in PCR assays. These quenchers are described in, e.g., Johansson et al., *J. Chem. Soc*. (2002) 124:6950-6956 and are commercially available from Biosearch Technologies (Novato, Calif.).

While the length of the primers and probes can vary, the probe sequences are selected such that they have a higher melt temperature than the primer sequences. Preferably, the probe sequences have an estimated melt temperature that is about 10° C. higher than the melt temperature for the amplification primer sequences. Hence, the primer sequences are generally shorter than the probe sequences. Typically, the primer sequences are in the range of between 10-75 nucleotides long, more typically in the range of 20-45. The typical probe is in the range of between 10-50 nucleotides long, more typically 15-40 nucleotides in length. Representative primers and probes useful in nucleic acid amplification assays are described above.

The dengue virus sequences described herein may also be used as a basis for transcription-mediated amplification (TMA) assays. TMA is an isothermal, autocatalytic nucleic acid target amplification system that can provide more than a billion RNA copies of a target sequence, and thus provides a method of identifying target nucleic acid sequences present in very small amounts in a biological sample. For a detailed description of TMA assay methods, see, e.g., Hill (2001) Expert Rev. Mol. Diagn. 1:445-55; WO 89/1050; WO 88/10315; EPO Publication No. 408,295; EPO Application No. 8811394-8.9; W091/02818; U.S. Pat. Nos. 5,399,491, 6,686,156, and 5,556,771, all incorporated herein by reference in their entireties.

Suitable DNA polymerases include reverse transcriptases, such as avian myeloblastosis virus (AMV) reverse transcriptase (available from, e.g., Seikagaku America, Inc.) and Moloney murine leukemia virus (MMLV) reverse transcriptase (available from, e.g., Bethesda Research Laboratories).

Promoters or promoter sequences suitable for incorporation in the primers are nucleic acid sequences (either naturally occurring, produced synthetically or a product of a restriction digest) that are specifically recognized by an RNA polymerase that recognizes and binds to that sequence and initiates the process of transcription whereby RNA transcripts are produced. The sequence may optionally include nucleotide bases extending beyond the actual recognition site for the RNA polymerase which may impart added stability or susceptibility to degradation processes or increased transcription efficiency. Examples of useful promoters include those which are recognized by certain bacteriophage polymerases such as those from bacteriophage T3, T7 or SP6, or a promoter from *E. coli*. These RNA polymerases are readily available from commercial sources, such as New England Biolabs and Epicentre.

Some of the reverse transcriptases suitable for use in the methods herein have an RNAse H activity, such as AMV reverse transcriptase. It may, however, be preferable to add exogenous RNAse H, such as *E. coli* RNAse H, even when AMV reverse transcriptase is used. RNAse H is readily available from, e.g., Bethesda Research Laboratories.

The RNA transcripts produced by these methods may serve as templates to produce additional copies of the target sequence through the above-described mechanisms. The system is autocatalytic and amplification occurs autocatalytically without the need for repeatedly modifying or changing reaction conditions such as temperature, pH, ionic strength or the like.

Detection may be done using a wide variety of methods, including direct sequencing, hybridization with sequence-specific oligomers, gel electrophoresis and mass spectrometry. These methods can use heterogeneous or homogeneous formats, isotopic or nonisotopic labels, as well as no labels at all.

One method of detection is the use of target sequence-specific oligonucleotide probes described above. The probes may be used in hybridization protection assays (HPA). In this embodiment, the probes are conveniently labeled with acridinium ester (AE), a highly chemiluminescent molecule. See, e.g., Nelson et al. (1995) "Detection of Acridinium Esters by Chemiluminescence" in *Nonisotopic Probing, Blotting and Sequencing*, Kricka L. J. (ed) Academic Press, San Diego, Calif.; Nelson et al. (1994) "Application of the Hybridization Protection Assay (HPA) to PCR" in *The Polymerase Chain Reaction*, Mullis et al. (eds.) Birkhauser, Boston, Mass.; Weeks et al., *Clin. Chem.* (1983) 29:1474-1479; Berry et al., *Clin. Chem.* (1988) 34:2087-2090. One AE molecule is directly attached to the probe using a non-nucleotide-based linker arm chemistry that allows placement of the label at any location within the probe. See, e.g., U.S. Pat. Nos. 5,585,481 and 5,185,439. Chemiluminescence is triggered by reaction with alkaline hydrogen peroxide which yields an excited N-methyl acridone that subsequently collapses to ground state with the emission of a photon.

When the AE molecule is covalently attached to a nucleic acid probe, hydrolysis is rapid under mildly alkaline conditions. When the AE-labeled probe is exactly complementary to the target nucleic acid, the rate of AE hydrolysis is greatly reduced. Thus, hybridized and unhybridized AE-labeled probe can be detected directly in solution, without the need for physical separation.

HPA generally consists of the following steps: (a) the AE-labeled probe is hybridized with the target nucleic acid in solution for about 15 to about 30 minutes. A mild alkaline solution is then added and AE coupled to the unhybridized probe is hydrolyzed. This reaction takes approximately 5 to 10 minutes. The remaining hybrid-associated AE is detected as a measure of the amount of target present. This step takes approximately 2 to 5 seconds. Preferably, the differential hydrolysis step is conducted at the same temperature as the hybridization step, typically at 50 to 70° C. Alternatively, a second differential hydrolysis step may be conducted at room temperature. This allows elevated pHs to be used, for example in the range of 10-11, which yields larger differences in the rate of hydrolysis between hybridized and unhybridized AE-labeled probe. HPA is described in detail in, e.g., U.S. Pat. Nos. 6,004,745; 5,948,899; and 5,283,174, the disclosures of which are incorporated by reference herein in their entireties.

In one example of a typical TMA assay, an isolated nucleic acid sample, suspected of containing a chikungunya virus target sequence, is mixed with a buffer concentrate containing the buffer, salts, magnesium, nucleotide triphosphates, primers, dithiothreitol, and spermidine. The reaction is optionally incubated at about 100° C. for approximately two minutes to denature any secondary structure. After cooling to room temperature, reverse transcriptase, RNA polymerase, and RNAse H are added and the mixture is incubated for two to four hours at 37° C. The reaction can then be assayed by denaturing the product, adding a probe solution, incubating 20 minutes at 60° C., adding a solution to selectively hydrolyze the unhybridized probe, incubating the reaction six minutes at 60° C., and measuring the remaining chemiluminescence in a luminometer.

The methods of detection of the invention utilize a biological sample suspected of containing chikungunya or Zika virus nucleic acids. A biological sample may be pretreated in any number of ways prior to assay for chikungunya or Zika virus nucleic acids. For instance, in certain embodiments, the sample may be treated to disrupt (or lyse) any viral particles (virions), for example by treating the samples with one or more detergents and/or denaturing agents (e.g., guanidinium agents). Nucleic acids may also be extracted from samples, for example, after detergent treatment and/or denaturing as described above. Total nucleic acid extraction may be performed using known techniques, for example by non-specific binding to a solid phase (e.g., silica). See, e.g., U.S. Pat. Nos. 5,234,809, 6,849,431; 6,838, 243; 6,815,541; and 6,720,166.

In certain embodiments, the target nucleic acids are separated from non-homologous nucleic acids using capture oligonucleotides immobilized on a solid support. Such capture oligonucleotides contain nucleic acid sequences that are complementary to a nucleic acid sequence present in the target chikungunya or Zika virus nucleic acid analyte such that the capture oligonucleotide can "capture" the target nucleic acid. Capture oligonucleotides can be used alone or in combination to capture dengue virus nucleic acids. For example, multiple capture oligonucleotides can be used in combination, e.g., 2, 3, 4, 5, 6, etc. different capture oligonucleotides can be attached to a solid support to capture target chikungunya or Zika virus nucleic acids. In certain embodiments, one or more capture oligonucleotides can be used to bind chikungunya or Zika virus target nucleic acids either prior to or after amplification by primer oligonucleotides and/or detection by probe oligonucleotides.

In one embodiment of the present invention the biological sample potentially carrying target nucleic acids is contacted with a solid support in association with capture oligonucleotides. The capture oligonucleotides, which may be used separately or in combination, may be associated with the solid support, for example, by covalent binding of the capture moiety to the solid support, by affinity association, hydrogen binding, or nonspecific association.

The capture oligonucleotides can include from about 5 to about 500 nucleotides of a conserved region from a chikungunya or Zika virus, preferably about 10 to about 100 nucleotides, or more preferably about 10 to about 60 nucleotides of the conserved region, or any integer within these ranges, such as a sequence including 18, 19, 20, 21, 22, 23, 24, 25, 26 . . . 35 . . . 40, etc. nucleotides from the conserved region of interest. In certain embodiments, the capture oligonucleotide comprises a sequence selected from the group consisting of SEQ ID NOS:1-30, or a complement thereof. The capture oligonucleotide may also be phosphorylated at the 3' end in order to prevent extension of the capture oligonucleotide.

The capture oligonucleotide may be attached to the solid support in a variety of manners. For example, the oligonucleotide may be attached to the solid support by attachment of the 3' or 5' terminal nucleotide of the probe to the solid support. More preferably, the capture oligonucleotide is attached to the solid support by a linker which serves to distance the probe from the solid support. The linker is usually at least 10-50 atoms in length, more preferably at least 15-30 atoms in length. The required length of the linker will depend on the particular solid support used. For example, a six atom linker is generally sufficient when high cross-linked polystyrene is used as the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. The homopolymeric sequence can be either 5' or 3' to the virus-specific sequence. In one aspect of the invention, the capture oligonucleotides include a homopolymer chain, such as, for example poly A, poly T, poly G, poly C, poly U, poly dA, poly dT, poly dG, poly dC, or poly dU in order to facilitate attachment to a solid support. The homopolymer chain can be from about 10 to about 40 nucleotides in length, or preferably about 12 to about 25 nucleotides in length, or any integer within these ranges, such as for example, 10 . . . 12 . . . 16, 17, 18, 19, 20, 21, 22, 23, or 24 nucleotides. The homopolymer, if present, can be added to the 3' or 5' terminus of the capture oligonucleotides by enzymatic or chemical methods. This addition can be made by stepwise addition of nucleotides or by ligation of a preformed homopolymer. Capture oligonucleotides comprising such a homopolymer chain can be bound to a solid support comprising a complementary homopolymer. Alternatively, biotinylated capture oligonucleotides can be bound to avidin- or streptavidin-coated beads. See, e.g., Chollet et al., supra.

Alternatively, polymers such as functionalized polyethylene glycol can be used as the linker. Such polymers do not significantly interfere with the hybridization of probe to the target oligonucleotide. Examples of linkages include polyethylene glycol, carbamate and amide linkages. The linkages between the solid support, the linker and the probe are preferably not cleaved during removal of base protecting groups under basic conditions at high temperature.

The solid support may take many forms including, for example, nitrocellulose reduced to particulate form and retrievable upon passing the sample medium containing the support through a sieve; nitrocellulose or the materials impregnated with magnetic particles or the like, allowing the nitrocellulose to migrate within the sample medium upon the application of a magnetic field; beads or particles which may be filtered or exhibit electromagnetic properties; and polystyrene beads which partition to the surface of an aqueous medium. Examples of types of solid supports for immobilization of the oligonucleotide probe include controlled pore glass, glass plates, polystyrene, avidin-coated polystyrene beads, cellulose, nylon, acrylamide gel and activated dextran.

In one embodiment, the solid support comprises magnetic beads. The magnetic beads may contain primary amine functional groups, which facilitate covalent binding or association of the capture oligonucleotides to the magnetic support particles. Alternatively, the magnetic beads have immobilized thereon homopolymers, such as poly T or poly A sequences. The homopolymers on the solid support will generally be complementary to any homopolymer on the capture oligonucleotide to allow attachment of the capture oligonucleotide to the solid support by hybridization. The use of a solid support with magnetic beads allows for a one-pot method of isolation, amplification and detection as the solid support can be separated from the biological sample by magnetic means.

The magnetic beads or particles can be produced using standard techniques or obtained from commercial sources. In general, the particles or beads may be comprised of magnetic particles, although they can also include other magnetic metal or metal oxides, whether in impure, alloy, or composite form, as long as they have a reactive surface and exhibit an ability to react to a magnetic field. Other materials that may be used individually or in combination with iron include, but are not limited to, cobalt, nickel, and silicon. A magnetic bead suitable for use with the present invention includes magnetic beads containing poly dT groups marketed under the trade name Sera-Mag magnetic oligonucleotide beads by Seradyn, Indianapolis, Ind.

Next, the association of the capture oligonucleotides with the solid support is initiated by contacting the solid support with the medium containing the capture oligonucleotides. In the preferred embodiment, the magnetic beads containing poly dT groups are hybridized with the capture oligonucleotides that comprise poly dA contiguous with the capture sequence (i.e., the sequence substantially complementary to a chikungunya virus nucleic acid sequence) selected from the conserved single stranded region of the chikungunya virus genome. The poly dA on the capture oligonucleotide and the poly dT on the solid support hybridize thereby immobilizing or associating the capture oligonucleotides with the solid support.

In certain embodiments, the capture oligonucleotides are combined with a biological sample under conditions suitable for hybridization with target chikungunya virus nucleic acids prior to immobilization of the capture oligonucleotides on a solid support. The capture oligonucleotide-target nucleic acid complexes formed are then bound to the solid support. In other embodiments, a solid support with associated capture oligonucleotides is brought into contact with a biological sample under hybridizing conditions. The immobilized capture oligonucleotides hybridize to the target nucleic acids present in the biological sample. Typically, hybridization of capture oligonucleotides to the targets can be accomplished in approximately 15 minutes, but may take as long as 3 to 48 hours.

The solid support is then separated from the biological sample, for example, by filtering, centrifugation, passing through a column, or by magnetic means. The solid support maybe washed to remove unbound contaminants and transferred to a suitable container (e.g., a microtiter plate). As will be appreciated by one of skill in the art, the method of separation will depend on the type of solid support selected. Since the targets are hybridized to the capture oligonucleotides immobilized on the solid support, the target strands are thereby separated from the impurities in the sample. In some cases, extraneous nucleic acids, proteins, carbohydrates, lipids, cellular debris, and other impurities may still be bound to the support, although at much lower concentrations than initially found in the biological sample. Those skilled in the art will recognize that some undesirable materials can be removed by washing the support with a washing medium. The separation of the solid support from the biological sample preferably removes at least about 70%, more preferably about 90% and, most preferably, at least about 95% or more of the non-target nucleic acids present in the sample.

As is readily apparent, design of the assays described herein is subject to a great deal of variation, and many formats are known in the art. The above descriptions are merely provided as guidance and one of skill in the art can readily modify the described protocols, using techniques well known in the art.

The above-described assay reagents, including the primers and probes, and optionally capture oligonucleotides, a solid support with bound probes, and/or reagents for performing nucleic acid amplification, such as by RT-PCR or NASBA, can be provided in kits, with suitable instructions and other necessary reagents, in order to conduct the assays for detecting chikungunya virus, Zika virus, or dengue virus, or any combination thereof, as described above. The kit will normally contain in separate containers the primers and probes, control formulations (positive and/or negative), and other reagents that the assay format requires. Instructions (e.g., written, CD-ROM, DVD, etc.) for carrying out the assay usually will be included in the kit. The kit can also contain, depending on the particular assay used, other packaged reagents and materials (i.e., wash buffers, and the like). Standard assays, such as those described above, can be conducted using these kits.

In certain embodiments, the kit comprises written instructions for identifying the presence of chikungunya virus and at least one set of primers including a forward primer and a reverse primer capable of amplifying at least a portion of a chikungunya virus genome, including an NSP2 target sequence. The kit may further comprise written instructions for identifying the presence of the chikungunya, quantitating the virus, and/or serotyping chikungunya virus. The kit may also comprise reagents for performing reverse transcriptase polymerase chain reaction (RT-PCR), nucleic acid sequence based amplification (NASBA), transcription-mediated amplification (TMA), or a fluorogenic 5' nuclease assay. In one embodiment, the kit further comprises oligonucleotide primers and probes for detecting dengue virus as described herein.

In one embodiment, the kit comprises: written instructions for identifying the presence of chikungunya virus; and at least one set of primers comprising a forward primer and a reverse primer capable of amplifying at least a portion of a chikungunya virus genome comprising an NSP2 target sequence, wherein the primers are not more than about 40 nucleotides in length, wherein the set of primers is selected from the group consisting of: a) a forward primer comprising the nucleotide sequence of SEQ ID NO:6 and a reverse primer comprising the sequence of SEQ ID NO:7; b) a forward primer comprising at least 10 contiguous nucleotides of the nucleotide sequence of SEQ ID NO:6 and a reverse primer comprising at least 10 contiguous nucleotides of the nucleotide sequence of SEQ ID NO:7; c) a forward primer comprising a nucleotide sequence having at least 95% identity to the sequence of SEQ ID NO:6 and a reverse primer comprising a nucleotide sequence having at least 95% identity to the sequence of SEQ ID NO:7, wherein the primer is capable of hybridizing to and amplifying chikungunya virus nucleic acids in the nucleic acid amplification assay; d) a forward primer and a reverse primer comprising at least one nucleotide sequence that differs from the corresponding nucleotide sequence of the forward primer or reverse primer of the primer set of (a) in that the primer has up to three nucleotide changes compared to the corresponding sequence, wherein the primer is capable of hybridizing to and amplifying chikungunya virus nucleic acids in the nucleic acid amplification assay; and e) a forward primer and a reverse primer comprising nucleotide sequences that are complements of the corresponding nucleotide sequences of the forward primer and reverse primer of a primer set selected from the group consisting of (a)-(d).

Additionally, the kit may further comprises at least one probe for detecting chikungunya virus in a biological sample, wherein the probe is selected from the group consisting of: a) a probe comprising the sequence of SEQ ID NO:8; b) a probe comprising a nucleotide sequence having at least 95% identity to the sequence of SEQ ID NO:8, wherein the probe is capable of hybridizing to and detecting the chikungunya virus RNA or an amplicon thereof; and c) a probe that differs from the corresponding nucleotide sequence of SEQ ID NO:8 by up to three nucleotide changes, wherein the probe is capable of hybridizing to and detecting the chikungunya virus RNA or an amplicon thereof.

In another embodiment, the kit further comprises reagents for detecting dengue virus, wherein the kit comprises a primer comprising the sequence of SEQ ID NO:9, a primer comprising the sequence of SEQ ID NO:10, a primer comprising the sequence of SEQ ID NO:11, a primer comprising the sequence of SEQ ID NO:12, a primer comprising the sequence of SEQ ID NO:13, a primer comprising the sequence of SEQ ID NO:14, a primer comprising the sequence of SEQ ID NO:15, and a primer comprising the sequence of SEQ ID NO:16.

Additionally, the kit may further comprises at least one probe for detecting dengue virus in a biological sample, wherein the probe is selected from the group consisting of: a) a probe comprising the sequence of SEQ ID NO:17, b) a probe comprising the sequence of SEQ ID NO:18, c) a probe comprising the sequence of SEQ ID NO:19, d) a probe comprising the sequence of SEQ ID NO:20, e) a probe comprising the sequence of SEQ ID NO:21, f) a probe comprising the sequence of SEQ ID NO:22, g) a probe comprising the sequence of SEQ ID NO:23, h) a probe comprising the sequence of SEQ ID NO:24, i) a probe comprising the sequence of SEQ ID NO:25, and j) a probe that differs from the corresponding nucleotide sequence of a probe selected from the group consisting of (a)-(i) in that the probe has up to three nucleotide changes compared to the corresponding sequence, wherein the probe is capable of hybridizing to and detecting the dengue virus RNA or amplicon thereof. In one embodiment, a set of probes is used for detecting dengue virus in a biological sample, wherein the set of probes comprises a probe comprising the sequence of SEQ ID NO:17, a probe comprising the sequence of SEQ ID NO:18, a probe comprising the sequence of SEQ ID NO:19, and a probe comprising the sequence of SEQ ID NO:20. In another embodiment, a set of probes is used for detecting dengue virus in a biological sample, wherein the set of probes comprises a probe comprising the sequence of SEQ ID NO:22, a probe comprising the sequence of SEQ ID NO:23, a probe comprising the sequence of SEQ ID NO:24, and a probe comprising the sequence of SEQ ID NO:25. In another embodiment, a set of primers and probes are used for detecting dengue virus in a biological sample comprising: a primer comprising the sequence of SEQ ID NO:9, a primer comprising the sequence of SEQ ID NO:10, a primer comprising the sequence of SEQ ID NO:11, a primer comprising the sequence of SEQ ID NO:12, a primer comprising the sequence of SEQ ID NO:13, a primer comprising the sequence of SEQ ID NO:14, a primer comprising the sequence of SEQ ID NO:15, a primer comprising the sequence of SEQ ID NO:16, a probe comprising the sequence of SEQ ID NO:17, a probe comprising the sequence of SEQ ID NO:18, a probe comprising the sequence of SEQ ID NO:19, and a probe comprising the sequence of SEQ ID NO:20.

In certain embodiments, the kit comprises written instructions for identifying the presence of Zika virus and at least one set of primers including a forward primer and a reverse primer capable of amplifying at least a portion of a Zika virus genome, including a conserved target sequence (e.g., a sequence from the region of the Zika virus genome corresponding to nucleotide position 7332 to 7432, numbered relative to the reference sequence of SEQ ID NO:6, of Zika virus strain MR766-NIID). The kit may further comprise written instructions for identifying the presence of the Zika virus, quantitating the virus, and/or serotyping the Zika virus. The kit may also comprise reagents for performing reverse transcriptase polymerase chain reaction (RT-PCR), nucleic acid sequence based amplification (NASBA), transcription-mediated amplification (TMA), or a fluorogenic 5' nuclease assay. In one embodiment, the kit further comprises probes for detecting Zika virus as described herein.

In another embodiment, the kit comprises: written instructions for identifying the presence of Zika virus; and at least one set of primers comprising a forward primer and a reverse primer capable of amplifying at least a portion of a Zika virus genome, wherein the primers are not more than about 40 nucleotides in length, wherein the set of primers is selected from the group consisting of: a) a forward primer comprising the nucleotide sequence of SEQ ID NO:27 and at least one reverse primer comprising a nucleotide sequence selected from the group consisting of SEQ ID NO:28 and SEQ ID NO:29; b) a forward primer comprising at least 10 contiguous nucleotides of the nucleotide sequence of SEQ ID NO:27 and at least one reverse primer comprising at least 10 contiguous nucleotides of a nucleotide sequence selected from the group consisting of SEQ ID NO:28 and SEQ ID NO:29; c) a forward primer comprising a nucleotide sequence having at least 95% identity to the sequence of SEQ ID NO:27 and at least one reverse primer comprising a nucleotide sequence having at least 95% identity to a nucleotide sequence selected from the group consisting of SEQ ID NO:28 and SEQ ID NO:29, wherein the primer is capable of hybridizing to and amplifying Zika virus nucleic acids in the nucleic acid amplification assay; d) a forward primer and at least one reverse primer comprising at least one nucleotide sequence that differs from the corresponding nucleotide sequence of the forward primer or at least one reverse primer of the primer set of (a) in that the primer has up to three nucleotide changes compared to the corresponding sequence, wherein the primer is capable of hybridizing to and amplifying Zika virus nucleic acids in the nucleic acid amplification assay; and e) a forward primer and at least one reverse primer comprising nucleotide sequences that are complements of the corresponding nucleotide sequences of the forward primer and reverse primer of a primer set selected from the group consisting of (a)-(d). In one embodiment, the kit comprises a forward primer comprising the nucleotide sequence of SEQ ID NO:27, a first reverse primer comprising the nucleotide sequence of SEQ ID NO:28, and a second reverse primer comprising the nucleotide sequence of SEQ ID NO:29.

Additionally, the kit may further comprises at least one probe for detecting Zika virus in a biological sample, wherein the probe is selected from the group consisting of: a) a probe comprising the sequence of SEQ ID NO:30; b) a probe comprising a nucleotide sequence having at least 95% identity to the sequence of SEQ ID NO:30, wherein the probe is capable of hybridizing to and detecting the Zika virus RNA or an amplicon thereof; and c) a probe that differs from the corresponding nucleotide sequence of SEQ ID NO:30 by up to three nucleotide changes, wherein the probe is capable of hybridizing to and detecting the Zika virus RNA or an amplicon thereof. In one embodiment, the kit comprises a forward primer comprising the nucleotide sequence of SEQ ID NO:27, a first reverse primer comprising the nucleotide sequence of SEQ ID NO:28, a second reverse primer comprising the nucleotide sequence of SEQ ID NO:29, and a probe comprising the sequence of SEQ ID NO:30.

In certain embodiments, the kit further comprises reagents for detecting chikungunya virus in combination with Zika virus. In certain embodiments, the kit comprises at least one set of primers comprising a forward primer and a reverse primer capable of amplifying at least a portion of a chikungunya virus genome comprising an NSP2 target sequence, wherein the primers are not more than about 40 nucleotides in length, wherein the set of primers is selected from the group consisting of: a) a forward primer comprising the nucleotide sequence of SEQ ID NO:6 and a reverse primer comprising the sequence of SEQ ID NO:7; b) a forward primer comprising at least 10 contiguous nucleotides of the nucleotide sequence of SEQ ID NO:6 and a reverse primer comprising at least 10 contiguous nucleotides of the nucleotide sequence of SEQ ID NO:7; c) a forward primer comprising a nucleotide sequence having at least 95% identity to the sequence of SEQ ID NO:6 and a reverse primer comprising a nucleotide sequence having at least 95% identity to the sequence of SEQ ID NO:7, wherein the primer is capable of hybridizing to and amplifying chikungunya virus nucleic acids in the nucleic acid amplification assay; d) a forward primer and a reverse primer comprising at least one nucleotide sequence that differs from the corresponding nucleotide sequence of the forward primer or reverse primer of the primer set of (a) in that the primer has up to three nucleotide changes compared to the corresponding sequence, wherein the primer is capable of hybridizing to and amplifying chikungunya virus nucleic acids in the nucleic acid amplification assay; and e) a forward primer and a reverse primer comprising nucleotide sequences that are complements of the corresponding nucleotide sequences of the forward primer and reverse primer of a primer set selected from the group consisting of (a)-(d). Additionally, the kit may further comprises at least one probe for detecting chikungunya virus in a biological sample, wherein the probe is selected from the group consisting of: a) a probe comprising the sequence of SEQ ID NO:8; b) a probe comprising a nucleotide sequence having at least 95% identity to the sequence of SEQ ID NO:8, wherein the probe is capable of hybridizing to and detecting the chikungunya virus RNA or an amplicon thereof; and c) a probe that differs from the corresponding nucleotide sequence of SEQ ID NO:8 by up to three nucleotide changes, wherein the probe is capable of hybridizing to and detecting the chikungunya virus RNA or an amplicon thereof.

In another embodiment, the kit further comprises reagents for detecting dengue virus in combination with Zika virus and/or chikungunya virus, wherein the kit comprises a primer comprising the sequence of SEQ ID NO:9, a primer comprising the sequence of SEQ ID NO:10, a primer comprising the sequence of SEQ ID NO:11, a primer comprising the sequence of SEQ ID NO:12, a primer comprising the sequence of SEQ ID NO:13, a primer comprising the sequence of SEQ ID NO:14, a primer comprising the sequence of SEQ ID NO:15, and a primer comprising the sequence of SEQ ID NO:16. Additionally, the kit may further comprises at least one probe for detecting dengue virus in a biological sample, wherein the probe is selected from the group consisting of: a) a probe comprising the sequence of SEQ ID NO:17, b) a probe comprising the sequence of SEQ ID NO:18, c) a probe comprising the sequence of SEQ ID NO:19, d) a probe comprising the sequence of SEQ ID NO:20, e) a probe comprising the sequence of SEQ ID NO:21, f) a probe comprising the sequence of SEQ ID NO:22, g) a probe comprising the sequence of SEQ ID NO:23, h) a probe comprising the sequence of SEQ ID NO:24, i) a probe comprising the sequence of SEQ ID NO:25, and j) a probe that differs from the corresponding nucleotide sequence of a probe selected from the group consisting of (a)-(i) in that the probe has up to three nucleotide changes compared to the corresponding sequence, wherein the probe is capable of hybridizing to and detecting the dengue virus RNA or amplicon thereof. In one embodiment, a set of probes is used for detecting dengue virus in a biological sample, wherein the set of probes comprises a probe comprising the sequence of SEQ ID NO:17, a probe comprising the sequence of SEQ ID NO:18, a probe comprising the sequence of SEQ ID NO:19, and a probe comprising the sequence of SEQ ID NO:20. In another embodiment, a set of probes is used for detecting dengue virus in a biological sample, wherein the set of probes comprises a probe comprising the sequence of SEQ ID NO:22, a probe comprising the sequence of SEQ ID NO:23, a probe comprising the sequence of SEQ ID NO:24, and a probe comprising the sequence of SEQ ID NO:25. In another embodiment, a set of primers and probes are used for detecting dengue virus in a biological sample comprising: a primer comprising the sequence of SEQ ID NO:9, a primer comprising the sequence of SEQ ID NO:10, a primer comprising the sequence of SEQ ID NO:11, a primer comprising the sequence of SEQ ID NO:12, a primer comprising the sequence of SEQ ID NO:13, a primer comprising the sequence of SEQ ID NO:14, a primer comprising the sequence of SEQ ID NO:15, a primer comprising the sequence of SEQ ID NO:16, a probe comprising the sequence of SEQ ID NO:17, a probe comprising the sequence of SEQ ID NO:18, a probe comprising the sequence of SEQ ID NO:19, and a probe comprising the sequence of SEQ ID NO:20.

3. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Clinical Evaluation of a Single-Reaction Real-Time RT-PCR for Pan-Dengue and Chikungunya Virus Detection Here, we describe the design and analytical and clinical evaluation of a multiplex assay for detecting Chikungunya and Dengue viruses, including a clinical comparison with reference molecular testing performed in Nicaragua.

Materials and Methods

Ethics Statement. Protocols for the collection and testing of samples from Nicaraguan pediatric dengue and chikungunya cases were reviewed and approved by the Institutional Review Boards (IRB) of the University of California, Berkeley, the Nicaraguan Ministry of Health, and Stanford University.

rRT-PCR Design and Performance. Design of the pan-DENV assay has been described previously (Waggoner et al. (2013) J. Clin. Microbiol. 51:2172-2181 and International Application Publication No. WO 2014/055746A1; herein incorporated by reference in their entireties). To design the CHIKV rRT-PCR, all CHIKV complete genome sequences (n=130) available in GenBank (accessed in April, 2013) were aligned using MegAlign software (DNAStar). A consensus sequence was generated that identified bases conserved across ≥95% of available sequences. Primers and probes were designed from the consensus sequence using Primer3 software. CHIKV primers and probes were tested in silico using BLASTn to search the National Center for Biotechnology Information (NCBI) nucleotide database. Following an initial evaluation of three primer sets, primers and probes targeting a region of the nsp2 gene (Table 1) were selected for improved analytical sensitivity (data not shown). To confirm that the selected primers and probe matched viral strains circulating in the Western Hemisphere, a second CHIKV consensus sequence was generated using all complete genome sequences deposited as of June, 2015.

The pan-DENV-CHIKV rRT-PCR reactions were performed in a total volume of 25 μL using the SuperScript III Platinum One-Step qRT-PCR kit (Life Technologies) and 5 μL of eluate. CHIKV primer and probe concentrations in the final reaction mixture are listed in Table 1. DENV primers and probes are shown in Tables 4 and 5. Concentrations of DENV primers and probes in the final reaction mixture were the same as those previously reported (Waggoner, supra). Analytical evaluation was performed on a Rotor-Gene Q instrument at Stanford University (RGQ, Qiagen), and the clinical evaluation was performed on a CFX96 instrument (Bio-Rad) at the National Virology Laboratory in Managua, Nicaragua. Cycling conditions were the following: 52° C. for 15 minutes; 94° C. for 2 minutes; 45 cycles of 94° C. for 15 seconds, 55° C. for 40 seconds, and 68° C. for 20 seconds. Each run was performed with a negative control (no template) and positive controls for DENV and CHIKV. Signal was acquired at 55° C., and analysis was performed on the linear scale. Thresholds were set manually on each instrument and used for analysis of each run (0.025 and 0.1 on the RGQ, 500 and 100 on the CFX96 for DENV and CHIKV, respectively). For both targets, any exponential curve crossing this threshold was considered positive. All results after cycle 40 were evaluated individually by two authors (JJW and GB).

Control Nucleic Acids and Reference Material. Quantitated, positive-sense, single-stranded DNA (ssDNA) oligonucleotides containing the target sequence for each DENV serotype and CHIKV were synthesized (Eurofins MWG Operon) and used in the analytical characterization of the pan-DENV-CHIKV rRT-PCR. The specificity of the pan-DENV-CHIKV rRT-PCR was evaluated by testing genomic RNA from the following viruses: DENV-1 Hawaii 1944, DENV-2 New Guinea C strain, DENV-3 strain H87, and DENV-4 strain H241, CHIKV (strain R80422a provided by the CDC Division of Vector Borne Diseases and the S27 Petersfield strain from Vircell Microbiologists, Granada, Spain), West Nile (4 strains), Japanese encephalitis, tick-borne encephalitis, yellow fever (two strains), Saint Louis encephalitis, Zika, o'nyong-nyong (ONNV, strain MP30) (Seymour et al. (2013) Am. J. Trop. Med. Hyg. 88:1170-1179), Semliki Forest, mayaro, Ross River, Getah, Barmah Forest, and Una (Waggoner et al. (2013) J. Clin. Microbiol. 51:2172-2181; Waggoner et al. (2014) J. Clin. Microbiol. 52:2011-2018). An additional 50 domestic (USA) samples with detectable hepatitis C virus (HCV) RNA were extracted and tested.

Analytical Characterization. The analytical evaluation of the pan-DENV-CHIKV rRT-PCR was performed according to published recommendations (17) and as previously described (Waggoner et al. (2013) J. Clin. Microbiol. 51:2172-2181; Waggoner et al. (2014) J. Clin. Microbiol. 52:2011-2018). Briefly, for each DENV serotype and CHIKV, linearity studies were performed using serial 10-fold dilutions of quantified ssDNA. Four replicates of each dilution from 7.0 $\log_{10}$ copies/μL to 1 copy/μL were tested on a single run. The linear range was established by fitting a best-fit line to the data by regression analysis and included the range where the $R^2$ value was ≥0.99. To establish the lower limit of 95% detection (95% LLOD), ten replicates of five 2-fold dilutions from 50 to 3.12 copies/μL, were tested on a single run. The 95% LLOD was then calculated using probit analysis.

Clinical Samples and Nucleic Acid Extraction. Pre-collected and de-identified serum samples from 182 Nicaraguan children with suspected dengue or chikungunya were used for the clinical evaluation of pan-DENV-CHIKV rRT-PCR. Samples were collected during 2013 and 2014 as part of two ongoing studies: the Nicaraguan Pediatric Dengue Cohort Study and a hospital-based dengue study, both based in Managua. Study design and methods for both of these studies have been described (Hammond et al. (2005) Am. J. Trop. Med. Hyg. 73:1063; Harris et al. (2000) Am. J. Trop. Med. Hyg. 63:5-11; Kuan et al. (2009) Am. J. Epidemiol. 170:120-129). RNA extractions were performed using the QIAamp Viral RNA Mini Kit (Qiagen) with 140 µL of serum using and an elution volume of 60 µL.

Reference Testing

All serum samples were tested for DENV RNA using a hemi-nested RT-PCR (Lanciotti et al. (1992) J. Clin. Micobiol. 30:545-551). Acute and convalescent serum samples were also tested for anti-DENV antibodies by IgM MAC-ELISA and Inhibition ELISA, which were interpreted as previously described (Gordon et al. (2013) PLoS Negl. Trop. Dis. 7:e2462). Eighty-one serum samples, collected in 2014, were tested for CHIKV using an rRT-PCR, which maintained a protocol from a published assay (Lanciotti et al. (2007) Emerg. Infect. Dis. 13:764-767) but substituted primers and probes designed to detect Asian and East-Central-South African genotypes of CHIKV. This will be referred to as the comparator CHIKV rRT-PCR. Primer and probe sequences for the comparator CHIKV rRT-PCR are as follows:

```
forward primer:
CHIKV 3855,
                                    (SEQ ID NO: 1)
GAGCATACGGTTACGCAGATAG;

reverse primers:
CHIKV 3957c-a,
                                    (SEQ ID NO: 2)
TACTGGTGATACATGGTGGTTTC
and CHIKV 3957c-b,
                                    (SEQ ID NO: 3)
TGCTGGTGACACATGGTGGTTTC;

probes:
CHIKV 3886 FAM-a,
                                    (SEQ ID NO: 4)
FAM-ACGAGTAATCTGCGTACTGGGACGTA-BHQ1
and CHIKV 3886 FAM-b,
                                    (SEQ ID NO: 5)
FAM-ACGAGTCATCTGCGTATTGGGACGCA-BHQ1.
```

Statistics. Kappa statistics were calculated with GraphPad software (GraphPad) and used to compare RT-PCR results. Probit analysis was performed using SPSS (IBM) to determine the 95% LLOD for the pan-DENV-CHIKV rRT-PCR.

Results

Analytical Evaluation. Using serial 10-fold dilutions of ssDNA, the linear range of the pan-DENV-CHIKV rRT-PCR for each DENV serotype and CHIKV extended from 7.0 to 2.0 $\log_{10}$ copies/µL. The 95% LLOD was calculated to be 12.0 copies/4, for DENV-1, 7.9 for DENV-2, 12.9 for DENV-3, 37.4 for DENV-4, and 15.3 for CHIKV.

Specificity. Amplification of genomic RNA from ONNV was observed in the CHIKV channel of the pan-DENV-CHIKV rRT-PCR. This generated a signal with reduced fluorescence compared to CHIKV genomic RNA controls (data not shown). Amplification of the DENV and CHIKV controls was detected in the appropriate channels without any cross-reaction. No amplification was observed when the pan-DENV-CHIKV rRT-PCR was performed using genomic RNA from the aforementioned viruses (see Material and Methods) or extracted nucleic acids from 50 patients with HCV (mean HCV viral load, 6.10 $\log_{10}$ IU/mL; standard deviation 0.76).

Clinical Samples. Sera from 182 Nicaraguan children with suspected dengue or chikungunya were tested for DENV using the pan-DENV-CHIKV rRT-PCR and hemi-nested DENV RT-PCR. Results of this comparison are shown in Table 2. The two assays showed very good agreement (kappa statistic, 0.91). Seventy-five patients tested positive for DENV using the hemi-nested RT-PCR, including patients with DENV-1 (n=44), DENV-2 (n=19), and DENV-3 (n=12). Seventy-four (98.7%) patients had detectable DENV RNA using the pan-DENV-CHIKV rRT-PCR. A single patient tested positive for DENV-1 in the hemi-nested RT-PCR but was not detected in the pan-DENV-CHIKV rRT-PCR. For an additional seven patients, DENV RNA could only be detected using the pan-DENV-CHIKV rRT-PCR. Five of these seven patients also tested positive for DENV by IgM MAC-ELISA (n=4) or Inhibition ELISA (n=1).

Serum samples from 81 children, collected in 2014, were also tested for CHIKV using the comparator CHIKV rRT-PCR (Table 3). CHIKV test results demonstrated complete agreement between the pan-DENV-CHIKV and comparator CHIKV rRT-PCRs (kappa statistic, 1.0). CHIKV RNA was not detected in any of the remaining 101 serum samples (collected in 2013) using the pan-DENV-CHIKV rRT-PCR and no co-infections were identified.

Discussion

In the current study, we describe the development and analytical and clinical evaluation of the pan-DENV-CHIKV rRT-PCR. This assay demonstrated excellent agreement with separate molecular comparators for DENV and CHIKV. In addition, the pan-DENV-CHIKV rRT-PCR requires only one reaction per sample instead of the three reactions and gel electrophoresis that are needed for the comparator assays. In this study, the pan-DENV-CHIKV rRT-PCR did not significantly improve DENV detection compared to the hemi-nested RT-PCR, which has been shown for the pan-DENV assay previously (Waggoner et al. (2013) J. Clin. Microbiol. 51:2172-2181). However, the current study was not powered to demonstrate superiority. Of the 97 patients in this study who tested negative for DENV using the hemi-nested RT-PCR and had available serological results, only 12 patients (12.4%) had results consistent with a recent DENV infection. Five of these patients were detected using the pan-DENV CHIKV assay.

Multiplex RT-PCRs for the detection of DENV and CHIKV have been reported in the literature previously (Cecilia et al. (2015) Arch. Virol. 160:323-327; Dash et al. (2008) Diagn. Microbiol. Infect. Dis. 62:52-57; Mishra et al. (2011) Diagn. Microbiol. Infect. Dis. 71:118-125; Naze et al. (2009) J. Virol. Meth. 162:1; Pongsiri et al. (2012) Asian Pac. J. Trop. Med. 5:342-346; Saha et al. (2013) J. Virol. Methods 193:521-524). However, only three groups have described single-reaction real-time assays for DENV and CHIKV (Cecilia et al., supra; Naze et al., supra; Pongsiri et al., supra), whereas others reported modified conventional RT-PCRs that require gel electrophoresis for detection (Dash et al., supra; Mishra et al., supra; Saha et al., supra). All multiplex rRT-PCRs appear to perform well, as reported, though most primer and probe sequences contain mismatches when aligned to consensus DENV and CHIKV sequences that include contemporary viruses obtained globally (see Materials and Methods). Furthermore, in these studies less common comparator assays were used as reference or the exact molecular comparator was unclear. These factors complicated the evaluation of the different multiplex rRT-PCRs reported in the literature, and made them unsuitable for use as reference molecular assays for these viruses. The goal of our study was, therefore, to design an rRT-PCR for CHIKV that would be compatible with the pan-DENV assay, an assay that has excellent clinical and analytical performance characteristics and that has been extensively evaluated in single- and multiplex formats (Waggoner et al. (2013) J. Clin. Microbiol. 51:2172-2181, Waggoner et al. (2014) J. Clin. Microbiol. 52:2011-2018, Waggoner et al. (2013) J. Clin. Microbiol. 51:3418-3420). The resulting pan-DENV-CHIKV rRT-PCR was then compared to widely used, reference assays for DENV and CHIKV in Nicaragua, which is experiencing the transmission of both viruses.

Although the pan-DENV-CHIKV rRT-PCR demonstrated very good analytical performance against all DENV serotypes and CHIKV, our study was limited by the absence of DENV-4 in clinical samples. DENV-4 was not circulating during the 2013 and 2014 DENV seasons in Managua, and it has rarely been identified in clinical dengue cases in Managua over the past 10 years (OhAinle et al. (2011) Sci. Transl. Med. 3:114ra128). During the analytical evaluation, the CHIKV rRT-PCR amplified genomic RNA from a reference ONNV isolate. The in silico evaluation of our primers and probe predicted two to four mismatches with ONNV, though only four complete ONNV genomes were available for analysis. However, the significance of this cross-reaction remains unclear given the rarity of ONNV infections. Finally, the CHIKV rRT-PCR was designed from an alignment performed prior to the emergence of CHIKV in the Western Hemisphere. The alignment was re-run using all complete genomes available as of June, 2015, and no new strains were identified with mutations in the primer and probe sequences.

In conclusion, we report the development and evaluation of the pan-DENV-CHIKV rRT-PCR. This assay demonstrated very good agreement with individual molecular comparators for DENV and CHIKV. The single-reaction, multiplex format of the pan-DENV-CHIKV rRT-PCR, combined with sensitive detection of both viruses, has the potential to improve detection while decreasing test costs and streamlining molecular workflow.

TABLE 1

CHIKV primer and probe sequences included in the pan-DENV-CHIKV rRT-PCR.

| Name | Sequence (5'→3') | Concentration* | Location** |
|---|---|---|---|
| CHIKV Forward | CATCTGCACYCAAGTGTACCA (SEQ ID NO: 6) | 200 nM | 2578-2598 |
| CHIKV Reverse | GCGCATTTTGCCTTCGTAATG (SEQ ID NO: 7) | 200 nM | 2654-2674 |
| CHIKV Probe*** | GCGGTGTACACTGCCTGTGAC YGC (SEQ ID NO: 8) | 100 nM | 2614-2637 |

*The concentration of each oligonucleotide in the final reaction mixture is provided.
**Genomic locations are provided based on the reference sequence Chikungunya virus strain S27-African prototype (Genbank: AF369024.2).
***The 5' fluor and 3' quencher on the CHIKV probe were Cal Fluor 610 and BHQ-2, respectively.

TABLE 2

Comparison of DENV detection in the pan-DENV-CHIKV rRT-PCR with detection in the hemi-nested DENV RT-PCR.

| | | Hemi-nested DENV RT-PCR | | |
|---|---|---|---|---|
| | | Positive | Negative | Total |
| pan-DENV-CHIKV rRT-PCR | Positive | 74 | 7* | 81 |
| | Negative | 1 | 100 | 101 |
| | Total | 75 | 107 | 182 |

*Five of seven patients also tested positive for DENV by IgM MAC-ELISA or Inhibition ELISA.

TABLE 3

Comparison of CHIKV detection in the pan-DENV-CHIKV rRT-PCR with detection in the reference CHIKV rRT-PCR.

| | | Comparator CHIKV rRT-PCR | | |
|---|---|---|---|---|
| | | Positive | Negative | Total |
| pan-DENV-CHIKV rRT-PCR | Positive | 57 | 0 | 57 |
| | Negative | 0 | 24 | 24 |
| | Total | 57 | 24 | 81 |

TABLE 4

Primer sequences for the dengue multiplex rRT-PCR.

| Name | Primer Sequence (5'→3') |
|---|---|
| Dengue 1-2-3 Forward | CAGATCTCTGATGAACAACCAACG (SEQ ID NO: 9) |
| Dengue 2 Forward C→T | CAGATCTCTGATGAATAACCAACG (SEQ ID NO: 10) |
| Dengue 3 Forward C→T | CAGATTTCTGATGAACAACCAACG (SEQ ID NO: 11) |
| Dengue 4 Forward | GATCTCTGGAAAAATGAAC (SEQ ID NO: 12) |
| Dengue 1, 3 Reverse | TTTGAGAATCTCTTCGCCAAC (SEQ ID NO: 13) |
| Dengue 2 Reverse | AGTTGACACGCGGTTTCTCT (SEQ ID NO: 14) |
| Dengue 2 Reverse A→G | AGTCGACACGCGGTTTCTCT (SEQ ID NO: 15) |
| Dengue 4 Reverse | AGAATCTCTTCACCAACC (SEQ ID NO: 16) |

TABLE 5

Probe sequences for the dengue multiplex rRT-PCR.

| Channel | 5' Fluor | Probe Sequence (5'→3') | 3' Quencher |
|---|---|---|---|
| Green | FAM | CGCGATCGCGTTTCAGCATA TTGAAAGACGGATCGCG (SEQ ID NO: 17) | BHQ-1 |
| Yellow | CAL Fluor Orange 560 | CGCGATCGCGTTTCAGCATA TTGAAAGGCGGATCGCG (SEQ ID NO: 18) | BHQ-1 |

TABLE 5 -continued

Probe sequences for the dengue multiplex rRT-PCR.

| | | | |
|---|---|---|---|
| Orange | CAL Fluor Red 610 | CGCGATC<u>CACGCGTTTCAGC ATATTGATAGGATCGCG</u> (SEQ ID NO: 19) | BHQ-2 |
| Red | Quasar Blue 670 | CGCGATC<u>TTTCAGCATATTG AAAGGTGGTC</u>GATCGCG (SEQ ID NO: 20) | BHQ-2 |

| Beacon Name | 5' Fluor | Sequence | 3' Quencher |
|---|---|---|---|
| Den1 Alternate | FAM | CGCGATCTTCAGCATATTGA AAGACGGTCGGATCGCG (SEQ ID NO: 21) | BHQ-1 |

| Taqman Name | 5' Fluor | Sequence | 3' Quencher |
|---|---|---|---|
| DENV1 BHQ+ | FAM | CTCGCGCGTTTCAGCATAT (SEQ ID NO: 22) | BHQplus |
| DENV2 BHQ+ | FAM | CTCTCGCGTTTCAGCATAT (SEQ ID NO: 23) | BHQplus |
| DENV2 Alt BHQ+ | FAM | CTCTCACGTTTCAGCATATTG (SEQ ID NO: 24) | BHQplus |
| DENV3 BHQ+ | FAM | CTCACGCGTTTCAGCATAT (SEQ ID NO: 25) | BHQplus |

Probes are listed by the channel in which signal is detected on the Rotor-Gene Q instrument.
Underlined probe segments designate sequences complimentary to the dengue consensus; segments on the 5' and 3' ends of the probe comprise the beacon stem.

EXAMPLE 2

Real-time RT-PCR for the Detection and Quantitation of Zika Virus with the Capability for Multiplexed Detection of Dengue and Chikungunya Viruses Introduction Here, we describe the design and analytical and clinical evaluation of a new rRT-PCR assay for Zika virus (ZIKV). This assay can be used alone or combined in a multiplex assay for DENV and CHIKV (hereinafter referred to as the DCZ assay).

ZIKV is a mosquito-borne flavivirus that was first identified in Uganda in 1947. Prior to 2007, very few cases of human infection with ZIKV had been identified and all had occurred in Africa or Asia. In 2007, an outbreak of ZIKV occurred on Yap Island, and in May 2015, ZIKV was identified in Brazil. This was the first documented transmission of ZIKV in the Western Hemisphere, and the virus has now spread to other countries in South America as well as Mexico, Central America, and islands in the Caribbean. Clinically, ZIKV cannot be reliably distinguished from infections with two other common arboviruses in this region, dengue virus (DENV) and chikungunya virus (CHIKV). Two real-time reverse-transcriptase PCRs (rRT-PCRs) for the detection of ZIKV have been published, though both assays are used solely in monoplex reactions (i.e. only for ZIKV). The purpose of the current project was to develop a new rRT-PCR for the detection and quantitation of ZIKV from patient samples as well as to optimize a multiplex, single-reaction rRT-PCR for the detection and differentiation of DENV, CHIKV, and ZIKV.

From an alignment of available ZIKV complete or near-complete genome sequences in GenBank, a new ZIKV rRT-PCR was designed for use in multiplex with assays for pan-DENV detection and CHIKV detection. Analytical evaluation of the ZIKV assay was performed as part of the multiplex reaction for DENV, CHIKV and ZIKV (referred to as the DCZ assay) in accordance with published recommendations. The ZIKV rRT-PCR had a dynamic range extending from 8.0 to 1.0 $\log_{10}$ copies/µL and a lower limit of 95% detection of 7.8 copies/µL. The DCZ assay was used to test 227 serum samples from patients with an acute febrile illness in Nicaragua. 177 patients tested positive using the DCZ assay, including 30 patients with DENV, 110 with CHIKV, 36 with DENV-CHIKV co-infections, and one patient with a ZIKV-CHIKV co-infection.

We have developed a new rRT-PCR for ZIKV and demonstrated that this test has a wide linear range and provides sensitive detection of viral RNA. Furthermore, the performance of this assay was evaluated in the single-reaction, multiplex DCZ assay. This assay provides sensitive detection of three important human arboviruses and has the potential to improve virus detection while decreasing testing costs and streamlining molecular workflow.

Methods rRT-PCR Design and Performance. To design the ZIKV rRT-PCR, all complete or nearly-complete (≥10,000 kb) ZIKV genome sequences available in GenBank (n=21; accessed 28 Mar. 2014) were aligned using MegAlign software (DNAStar). A consensus sequence was generated that identified bases conserved across ≥95% of available sequences. Primers and probes were designed from the consensus sequence using Primer3 software. Four target regions were identified; primers and probes were designed and evaluated for each region. ZIKV primers and probes were tested in silico using BLASTn to search the National Center for Biotechnology Information (NCBI) nucleotide database. The final primer-probe set was selected for improved analytical sensitivity and maintained in silico specificity. To determine optimal concentrations in the final reaction, the ZIKV primers and probe were tested, in multiplex with the pan-DENV and CHIKV rRT-PCRs, at each combination of 100, 200, and 400 nM primer and 100, 200, and 400 nM probe. The concentration of DENV primers and probes in the final reaction were maintained from the pan-DENV-CHIKV rRT-PCR (Waggoner et al. (2016) J. Clin. Virol. 78:57-61). The CHIKV primers and probe (Table 2) were used at 300 nM and 100 nM, respectively, in the final DCZ reaction.

The DCZ assay and ZIKV rRT-PCR were performed in a total volume of 25 µL using the SuperScript III Platinum One-Step qRT-PCR kit (Life Technologies) and 5 µL of nucleic acid eluate. ZIKV primer and probe concentrations in the final reaction mixture are listed in Table 6. Evaluation was performed on a Rotor-Gene Q instrument at Stanford University (RGQ, Qiagen) and an ABI7500 instrument (Life Technologies) at the National Virology Laboratory in Managua, Nicaragua. Cycling conditions were the following: 52° C. for 15 minutes; 94° C. for 2 minutes; 45 cycles of 94° C. for 15 seconds, 55° C. for 40 seconds, and 68° C. for 20 seconds. Each run was performed with a negative control (no template) and a positive control for ZIKV. The DCZ assay was performed with controls for DENV, CHIKV and ZIKV. Signal was acquired at 55° C., and analysis was performed on the linear scale. Thresholds were set manually on each instrument and used for analysis of each run. For both targets, any exponential curve crossing this threshold was considered positive.

Control Nucleic Acids and Reference Material. Quantitated, positive-sense, single-stranded DNA (ssDNA) oligonucleotides containing the target sequence for ZIKV, each DENV serotype, and CHIKV were synthesized (Eurofins MWG Operon) and used in the analytical characterization of the ZIKV rRT-PCR and DCZ assays. The specificity of the ZIKV rRT-PCR, as a component of the DCZ assay, was evaluated by testing genomic RNA from the following viruses: DENV-1 Hawaii 1944, DENV-2 New Guinea C strain, DENV-3 strain H87, and DENV-4 strain H241, CHIKV (strain R80422a provided by the CDC Division of Vector Borne Diseases), West Nile (NY 1999 strain), and hepatitis C virus (genotype 1).

Analytical Characterization. The analytical evaluation of the ZIKV rRT-PCR was performed as part of the DCZ assay according to published recommendations (Burd (2010) Clin. Microbiol. Rev. 23:550-576) and as previously described (Waggoner et al. (2013) J. Clin. Microbiol. 51:2172-2181; Waggoner et al. (2014) J. Clin. Microbiol. 52:2011-18). Briefly, for ZIKV, each DENV serotype, and CHIKV, linearity studies were performed using serial 10-fold dilutions of quantified ssDNA. Four replicates of each dilution from 8.0 $\log_{10}$ copies/µL to 1 copy/µL were tested on a single run. The linear range was established by fitting a best-fit line to the data by regression analysis and included the range where the $R^2$ value was ≥0.99. To establish the lower limit of 95% detection (95% LLOD), ten replicates of five 2-fold dilutions from 50 to 3.12 copies/µL were tested on a single run. The 95% LLOD was then calculated using probit analysis.

Clinical Samples and Nucleic Acid Extraction. Pre-collected and de-identified serum samples from 227 Nicaraguan patients with suspected dengue, chikungunya, or Zika were used for the clinical evaluation of the DCZ assay. Samples were collected during 2015 as part of the Nicaraguan National Surveillance System and two ongoing studies: the Nicaraguan Pediatric Dengue Cohort Study and a hospital-based dengue study, both based in Managua. Study design and methods for both of these studies have been described (Hammond et al. (2005) Am. J. Trop. Med. Hyg. 73:1063; Harris et al. (2000) Am. J. Trop. Med. Hyg. 63:5-11; Kuan et al. (2009) Am. J. Epidemiol. 170:120-129). RNA extractions were performed using the QIAamp Viral RNA Mini Kit (Qiagen) with 140 µL of serum using and an elution volume of 60 µL.

Statistics. Kappa statistics were calculated with GraphPad software (GraphPad) and used to compare RT-PCR results. $C_T$ values from DENV- and CHIKV-positive clinical samples were compared by unpaired t test (GraphPad). Probit analysis was performed using SPSS (IBM) to determine the 95% LLOD for the ZIKV rRT-PCR.

Results

Analytical Evaluation. Using serial 10-fold dilutions of ssDNA, the linear range of the pan-DENV-CHIKV rRT-PCR for ZIKV extended from 8.0 to 1.0 $\log_{10}$ copies/µL. The 95% LLOD was calculated to be 7.8 copies/µL, (5.7-27.2, 95% CI). Amplification of ZIKV, DENV and CHIKV controls was detected in the appropriate channels without cross-reaction. No amplification was observed when the DCZ assay was performed using genomic RNA from the aforementioned viruses (see Material and Methods).

Clinical Samples. Sera from 227 Nicaraguan patients with suspected dengue, chikungunya, or Zika were tested using the DCZ assay. 177 patients (78.0%) tested positive for one or more viruses: 110 for CHIKV mono-infection, 30 for DENV mono-infection, 36 for DENV-CHIKV co-infection, and 1 patient for CHIKV-ZIKV co-infection. The remaining 50 patients (22.0%) were negative using the DCZ assay.

Discussion

We describe the development a new rRT-PCR for ZIKV and the analytical and clinical evaluation of this rRT-PCR as a component of the DCZ assay. The DCZ multiplex assay demonstrated excellent analytical sensitive, a wide dynamic range, and provided an etiologic diagnosis for a high-percentage of patients with an acute febrile illness and suspected arbovirus infection. The DCZ assay also provides all of this a single, real-time reaction. Multiplex rRT-PCRs for the detection of DENV, CHIKV, and ZIKV have not been reported to date. Recommended testing protocols for these viruses often involve the performance of separate molecular tests for each virus, which can amount to six separate reactions in total. The goal of our study was, therefore, to design an rRT-PCR for ZIKV that would be compatible with previously designed assays for pan-DENV and CHIKV detection (Waggoner et al. (2016) J. Clin. Virol. 78:57-61). The resulting DCZ assay was then evaluated using clinical samples collected in Nicaragua, which is experiencing the transmission of DENV and CHIKV currently.

In conclusion, we report the development and evaluation of a new ZIKV rRT-PCR and the DCZ assay. This assay demonstrated very good analytical and clinical performance. The single-reaction, multiplex format of the DCZ assay, combined with sensitive detection of both viruses, has the potential to improve detection while decreasing test costs and streamlining molecular workflow.

TABLE 6

ZIKV primer and probe sequences.

| Name | Sequence (5'→3') | Concentration[a] | Location[b] |
|---|---|---|---|
| ZIKV Forward | CAGCTGGCATCATGAAGAAYC (SEQ ID NO: 27) | 300 nM | 7332-7352 |
| ZIKV Reverse 1 | CACTTGTCCCATCTTCTTCTCC (SEQ ID NO: 28) | 300 nM | 7411-7432 |
| ZIKV 2 Reverse | CACCTGTCCCATCTTTTTCTCC (SEQ ID NO: 29) | 300 nM | 7411-7432 |
| ZIKV Probe | CYGTTGTGGATGGAATAGTGG (SEQ ID NO: 30) | 100 nM | 7355-7373 |

[a]The concentration of each oligonucleotide in the final reaction mixture is provided.
[b]Genomic locations are provided based on the reference sequence Zika virus strain: MR766-NIID (Genbank: LC002520.1).

TABLE 7

CHIKV primer and probe sequences for the pan-ZIKV-CHIKV rRT-PCR.

| Name | Sequence (5'→3') | Concentration* | Location** |
|---|---|---|---|
| CHIKV Forward | CATCTGCACYCAAGTGTACCA (SEQ ID NO: 6) | 300 nM | 2578-2598 |
| CHIKV Reverse | GCGCATTTTGCCTTCGTAATG (SEQ ID NO: 7) | 300 nM | 2654-2674 |
| CHIKV Probe*** | GCGGTGTACACTGCCTGTGACYGC (SEQ ID NO: 8) | 100 nM | 2614-2637 |

*The concentration of each oligonucleotide in the final reaction mixture is provided.
**Genomic locations are provided based on the reference sequence Chikungunya virus strain S27-African prototype (Genbank: AF369024.2).
***The 5' fluor and 3' quencher on the CHIKV probe were Cal Fluor 610 and BHQ-2, respectively.

Thus, oligonucleotide reagents, including primers and probes, as well as methods of using the reagents for detection of chikungunya, Zika, and dengue viruses are described. Although preferred embodiments of the subject invention have been described in some detail, it is understood that obvious variations can be made without departing from the spirit and the scope of the invention as defined herein.

---

What is claimed is:

1. A method for detecting chikungunya virus, the method comprising:
   a) contacting nucleic acids of a biological sample derived from a subject suspected of containing chikungunya virus, wherein the biological sample is a human blood sample or a serum sample derived from human blood, with a composition comprising a forward primer and a reverse primer capable of amplifying at least a portion of a chikungunya virus genome, wherein each of the forward primer and the reverse primer is not more than 40 nucleotides in length and wherein the forward primer comprises a sequence that ends at the 3' end with the nucleotide sequence of SEQ ID NO: 6 and the reverse primer comprises a sequence that ends at the 3' end with the sequence of SEQ ID NO: 7;
   b) amplifying at least a portion of a chikungunya virus RNA, if present, wherein the chikungunya virus RNA comprises an NSP2 target sequence; and
   c) detecting the presence of the amplified nucleic acids using at least one detectably labeled oligonucleotide probe sufficiently complementary to and capable of hybridizing with the chikungunya virus RNA or amplicon thereof, if present, as an indication of the presence or absence of chikungunya virus in the sample, wherein the probe comprises a sequence that ends at the 5' end with the sequence of SEQ ID NO:8.

2. The method of claim 1, wherein the detectably labeled probe comprises a fluorophore.

3. The method of claim 2, wherein the detectably labeled probe comprises a 5'-fluorophore and a 3'-quencher.

4. The method of claim 1, further comprising detecting dengue virus in the biological sample.

5. The method of claim 4, wherein the primers used for detecting dengue virus in the biological sample comprise a primer comprising the sequence of SEQ ID NO:9, a primer comprising the sequence of SEQ ID NO:10, a primer comprising the sequence of SEQ ID NO:11, a primer comprising the sequence of SEQ ID NO:12, a primer comprising the sequence of SEQ ID NO:13, a primer comprising the sequence of SEQ ID NO:14, a primer comprising the sequence of SEQ ID NO:15, and a primer comprising the sequence of SEQ ID NO:16.

6. The method of claim 5, further comprising using at least one probe to detect dengue virus, wherein said at least one probe is selected from the group consisting of:
   a) a probe comprising the sequence of SEQ ID NO:17,
   b) a probe comprising the sequence of SEQ ID NO:18,
   c) a probe comprising the sequence of SEQ ID NO:19,
   d) a probe comprising the sequence of SEQ ID NO:20,
   e) a probe comprising the sequence of SEQ ID NO:21,
   f) a probe comprising the sequence of SEQ ID NO:22,
   g) a probe comprising the sequence of SEQ ID NO:23,
   h) a probe comprising the sequence of SEQ ID NO:24,
   i) a probe comprising the sequence of SEQ ID NO:25, and
   j) a probe that differs from the corresponding nucleotide sequence of a probe selected from the group consisting of (a)-(i) in that the probe has up to three nucleotide changes compared to the corresponding sequence, wherein the probe is capable of hybridizing to and detecting the dengue virus RNA or amplicon thereof.

7. The method of claim 6, wherein a set of primers and probes are used for detecting dengue virus in a biological sample comprising: a primer comprising the sequence of SEQ ID NO:9, a primer comprising the sequence of SEQ ID NO:10, a primer comprising the sequence of SEQ ID NO:11, a primer comprising the sequence of SEQ ID NO:12, a primer comprising the sequence of SEQ ID NO:13, a primer comprising the sequence of SEQ ID NO:14, a primer comprising the sequence of SEQ ID NO:15, a primer comprising the sequence of SEQ ID NO:16, a probe comprising the sequence of SEQ ID NO:17, a probe comprising the sequence of SEQ ID NO:18, a probe comprising the sequence of SEQ ID NO:19, and a probe comprising the sequence of SEQ ID NO:20.

8. The method of claim 7, wherein the probe comprising the sequence of SEQ ID NO:17 further comprises a 5' fluorophore and a 3' quencher, the probe comprising the sequence of SEQ ID NO:18 further comprises a 5' fluorophore and a 3' quencher, the probe comprising the sequence of SEQ ID NO:19 further comprises a 5' fluorophore and a 3' quencher, and the probe comprising the sequence of SEQ ID NO:20 further comprises a 5' fluorophore and a 3' quencher.

9. The method of claim 6, wherein a set of primers and probes are used for detecting dengue virus in a biological sample comprising: a primer comprising the sequence of SEQ ID NO:9, a primer comprising the sequence of SEQ ID NO:10, a primer comprising the sequence of SEQ ID NO:11, a primer comprising the sequence of SEQ ID NO:12, a primer comprising the sequence of SEQ ID NO:13, a primer comprising the sequence of SEQ ID NO:14, a primer comprising the sequence of SEQ ID NO:15, a primer comprising the sequence of SEQ ID NO:16, a probe comprising the sequence of SEQ ID NO:22, a probe comprising the sequence of SEQ ID NO:23, a probe comprising the sequence of SEQ ID NO:24, and a probe comprising the sequence of SEQ ID NO:25.

10. The method of claim 9, wherein the probe comprising the sequence of SEQ ID NO:22 further comprises a 5' fluorophore and a 3' quencher, the probe comprising the sequence of SEQ ID NO:23 further comprises a 5' fluorophore and a 3' BHQplus quencher, the probe comprising the sequence of SEQ ID NO:24 further comprises a 5' fluorophore and a 3' quencher, and the probe comprising the sequence of SEQ ID NO:25 further comprises a fluorophore and a 3' quencher.

11. The method of claim 1, wherein amplifying comprises reverse transcriptase polymerase chain reaction (RT-PCR), nucleic acid sequence based amplification (NASBA), transcription-mediated amplification (TMA), or a fluorogenic 5' nuclease assay, or a combination thereof.

* * * * *

SEQUENCE LISTING

<160> NUMBER OF SEQ ID NOS: 32

<210> SEQ ID NO 1
<211> LENGTH: 22
<212> TYPE: DNA
<213> ORGANISM: Artificial Sequence
<220> FEATURE:
<223> OTHER INFORMATION: CHIKV 3855 Forward Primer

<400> SEQUENCE: 1
gagcatacgg ttacgcagat ag                                            22

<210> SEQ ID NO 2
<211> LENGTH: 23
<212> TYPE: DNA
<213> ORGANISM: Artificial Sequence
<220> FEATURE:
<223> OTHER INFORMATION: CHIKV 3957c-a Reverse Primer

<400> SEQUENCE: 2
tactggtgat acatggtggt ttc                                           23

<210> SEQ ID NO 3
<211> LENGTH: 23
<212> TYPE: DNA
<213> ORGANISM: Artificial Sequence
<220> FEATURE:
<223> OTHER INFORMATION: CHIKV 3957c-b Reverse Primer

<400> SEQUENCE: 3
tgctggtgac acatggtggt ttc                                           23

<210> SEQ ID NO 4
<211> LENGTH: 26
<212> TYPE: DNA
<213> ORGANISM: Artificial Sequence
<220> FEATURE:
<223> OTHER INFORMATION: CHIKV 3886 FAM-a Probe

<400> SEQUENCE: 4
acgagtaatc tgcgtactgg gacgta                                        26

<210> SEQ ID NO 5
<211> LENGTH: 26
<212> TYPE: DNA
<213> ORGANISM: Artificial Sequence
<220> FEATURE:
<223> OTHER INFORMATION: CHIKV 3886 FAM-b Probe

<400> SEQUENCE: 5
acgagtcatc tgcgtattgg gacgca                                        26

<210> SEQ ID NO 6
<211> LENGTH: 21
<212> TYPE: DNA
<213> ORGANISM: Artificial Sequence
<220> FEATURE:
<223> OTHER INFORMATION: CHIKV Forward Primer

<400> SEQUENCE: 6
catctgcacy caagtgtacc a                                              21

<210> SEQ ID NO 7
<211> LENGTH: 21
<212> TYPE: DNA
<213> ORGANISM: Artificial Sequence
<220> FEATURE:
<223> OTHER INFORMATION: CHIKV Reverse Primer

<400> SEQUENCE: 7
gcgcattttg ccttcgtaat g                                              21

<210> SEQ ID NO 8
<211> LENGTH: 24
<212> TYPE: DNA
<213> ORGANISM: Artificial Sequence
<220> FEATURE:
<223> OTHER INFORMATION: CHIKV Probe

<400> SEQUENCE: 8
gcggtgtaca ctgcctgtga cygc                                           24

<210> SEQ ID NO 9
<211> LENGTH: 24
<212> TYPE: DNA
<213> ORGANISM: Artificial Sequence
<220> FEATURE:
<223> OTHER INFORMATION: Dengue 1-2-3 forward PCR primer

<400> SEQUENCE: 9
cagatctctg atgaacaacc aacg                                           24

<210> SEQ ID NO 10
<211> LENGTH: 24
<212> TYPE: DNA
<213> ORGANISM: Artificial Sequence
<220> FEATURE:
<223> OTHER INFORMATION: Dengue 2 forward (C to T) PCR primer

<400> SEQUENCE: 10
cagatctctg atgaataacc aacg                                           24

<210> SEQ ID NO 11
<211> LENGTH: 24
<212> TYPE: DNA
<213> ORGANISM: Artificial Sequence
<220> FEATURE:
<223> OTHER INFORMATION: Dengue 3 forward (C to T) PCR primer

<400> SEQUENCE: 11
cagatttctg atgaacaacc aacg                                           24

<210> SEQ ID NO 12
<211> LENGTH: 19
<212> TYPE: DNA
<213> ORGANISM: Artificial Sequence
<220> FEATURE:
<223> OTHER INFORMATION: Dengue 4 forward PCR primer

<400> SEQUENCE: 12
gatctctgga aaaatgaac                                                 19

<210> SEQ ID NO 13
<211> LENGTH: 21

```
<212> TYPE: DNA
<213> ORGANISM: Artificial Sequence
<220> FEATURE:
<223> OTHER INFORMATION: Dengue 1, 3 reverse PCR primer

<400> SEQUENCE: 13
tttgagaatc tcttcgccaa c                                               21

<210> SEQ ID NO 14
<211> LENGTH: 20
<212> TYPE: DNA
<213> ORGANISM: Artificial Sequence
<220> FEATURE:
<223> OTHER INFORMATION: Dengue 2 reverse PCR primer

<400> SEQUENCE: 14
agttgacacg cggtttctct                                                 20

<210> SEQ ID NO 15
<211> LENGTH: 20
<212> TYPE: DNA
<213> ORGANISM: Artificial Sequence
<220> FEATURE:
<223> OTHER INFORMATION: Dengue 2 reverse (A to G) PCR primer

<400> SEQUENCE: 15
agtcgacacg cggtttctct                                                 20

<210> SEQ ID NO 16
<211> LENGTH: 18
<212> TYPE: DNA
<213> ORGANISM: Artificial Sequence
<220> FEATURE:
<223> OTHER INFORMATION: Dengue 4 reverse PCR primer

<400> SEQUENCE: 16
agaatctctt caccaacc                                                   18

<210> SEQ ID NO 17
<211> LENGTH: 37
<212> TYPE: DNA
<213> ORGANISM: Artificial Sequence
<220> FEATURE:
<223> OTHER INFORMATION: Dengue probe

<400> SEQUENCE: 17
cgcgatcgcg tttcagcata ttgaaagacg gatcgcg                              37

<210> SEQ ID NO 18
<211> LENGTH: 37
<212> TYPE: DNA
<213> ORGANISM: Artificial Sequence
<220> FEATURE:
<223> OTHER INFORMATION: Dengue probe

<400> SEQUENCE: 18
cgcgatcgcg tttcagcata ttgaaaggcg gatcgcg                              37

<210> SEQ ID NO 19
<211> LENGTH: 37
<212> TYPE: DNA
<213> ORGANISM: Artificial Sequence
<220> FEATURE:
<223> OTHER INFORMATION: Dengue probe

<400> SEQUENCE: 19
```
cgcgatccac gcgtttcagc atattgatag gatcgcg                                  37

<210> SEQ ID NO 20
<211> LENGTH: 37
<212> TYPE: DNA
<213> ORGANISM: Artificial Sequence
<220> FEATURE:
<223> OTHER INFORMATION: Dengue probe

<400> SEQUENCE: 20
cgcgatcttt cagcatattg aaaggtggtc gatcgcg                                  37

<210> SEQ ID NO 21
<211> LENGTH: 37
<212> TYPE: DNA
<213> ORGANISM: Artificial Sequence
<220> FEATURE:
<223> OTHER INFORMATION: Dengue probe

<400> SEQUENCE: 21
cgcgatcttc agcatattga aagacggtcg gatcgcg                                  37

<210> SEQ ID NO 22
<211> LENGTH: 19
<212> TYPE: DNA
<213> ORGANISM: Artificial Sequence
<220> FEATURE:
<223> OTHER INFORMATION: Dengue probe

<400> SEQUENCE: 22
ctcgcgcgtt tcagcatat                                                      19

<210> SEQ ID NO 23
<211> LENGTH: 19
<212> TYPE: DNA
<213> ORGANISM: Artificial Sequence
<220> FEATURE:
<223> OTHER INFORMATION: Dengue probe

<400> SEQUENCE: 23
ctctcgcgtt tcagcatat                                                      19

<210> SEQ ID NO 24
<211> LENGTH: 21
<212> TYPE: DNA
<213> ORGANISM: Artificial Sequence
<220> FEATURE:
<223> OTHER INFORMATION: Dengue probe

<400> SEQUENCE: 24
ctctcacgtt tcagcatatt g                                                   21

<210> SEQ ID NO 25
<211> LENGTH: 19
<212> TYPE: DNA
<213> ORGANISM: Artificial Sequence
<220> FEATURE:
<223> OTHER INFORMATION: Dengue probe

<400> SEQUENCE: 25
ctcacgcgtt tcagcatat                                                      19

<210> SEQ ID NO 26
<211> LENGTH: 11826
<212> TYPE: DNA
<213> ORGANISM: Chikungunya virus

```
<300> PUBLICATION INFORMATION:
<308> DATABASE ACCESSION NUMBER: NCBI/NC_004162
<309> DATABASE ENTRY DATE: 2012-06-27
<313> RELEVANT RESIDUES IN SEQ ID NO: (1)..(11826)

<400> SEQUENCE: 26
atggctgcgt gagacacacg tagcctacca gtttcttact gctctactct gcaaagcaag      60
agattaagaa cccatcatgg atcctgtgta cgtggacata gacgctgaca gcgccttttt     120
gaaggccctg caacgtgcgt accccatgtt tgaggtggaa cctaggcagg tcacaccgaa     180
tgaccatgct aatgctagag cgttctcgca tctagctata aaactaatag agcaggaaat     240
tgatcccgac tcaaccatcc tggatattgg tagtgcgcca gcaaggagga tgatgtcgga     300
caggaagtac cactgcgttt gcccgatgcg cagtgcagaa gatcccgaga gactcgccaa     360
ttatgcgaga aagctagcat ctgccgcagg aaaagtcctg gacagaaaca tctctggaaa     420
gatcggggac ttacaagcag taatggccgt gccagacacg gagacgccaa cattctgctt     480
acacacagat gtatcatgta gacagagagc agacgtcgcg atataccaag acgtctatgc     540
tgtacacgca cccacgtcgc tataccacca ggcgattaaa ggggtccgat ggcgtactg      600
ggtagggttt gacacaaccc cgttcatgta caatgccatg gcgggtgcct acccctcata     660
ctcgacaaat tgggcagatg agcaggtact gaaggctaag aacataggat tatgttcaac     720
agacctgacg gaaggtagac gaggcaaatt gtctattatg agaggaaaaa gctagaacc     780
gtgcgaccgt gtgctgttct cagtagggtc aacgctctac ccggaaagcc gtaagctact     840
taagagctgg cacctaccat cggtgttcca tttaaagggc aagctcagct tcacatgccg     900
ctgtgataca gtggtttcgt gcgaaggcta cgtcgttaag agaataacga tgagcccagg     960
cctttacgga aaaccacag ggtatgcggt aacccaccac gcagacgat tcctgatgtg     1020
caagaccacc gacacggttg acggcgaaag agtgtcattc tcggtgtgca cgtacgtgcc     1080
ggcgaccatt tgtgatcaaa tgaccggcat ccttgctaca gaagtcacgc cggaggatgc     1140
acagaagctg ttggtggggc tgaaccagag aatagtggtt aacggcagaa cgcaacggaa     1200
tacgaacacc atgaaaaact atatgattcc cgtggtcgcc caagccttca gtaagtgggc     1260
aaaggagtgc cggaaagaca tggaagatga aaaactcctg ggggtcagag aaagaacact     1320
gacctgctgc tgtctatggg catttaagaa gcagaaaaca cacacggtct acaagaggcc     1380
tgatacccag tcaattcaga aggttcaggc cgagtttgac agctttgtgg taccgagcct     1440
gtggtcgtcc gggttgtcaa tcccgttgag gactagaatc aaatggttgt taagcaaggt     1500
gccaaaaacc gacctgaccc catacagcgg ggacgcccaa gaagcccggg acgcagaaaa     1560
agaagcagag gaagaacgag aagcagaact gactcttgaa gccctaccac cccttcaggc     1620
agcacaggaa gatgttcagg tcgaaatcga cgtggaacag cttgaggaca gagcgggtgc     1680
aggaataata gagactccga gaggagctat caaagttact gcccaaccaa cagaccacgt     1740
cgtgggagag tacttggttt tttccccgca gaccgtacta cgtagccaaa agcttagcct     1800
gattcacgct ttggcggagc aagtgaagac gtgcacgcac agcggacgag cagggaggta     1860
tgcggtcgaa gcgtacgacg gcagagtcct agtgccctca ggctacgcaa tctcgcctga     1920
agacttccag agcctaagcg aaagcgcaac gatggtgtac aacgaaagag agttcgtaaa     1980
cagaaagcta caccatattg cgatgcatgg accagcectg aacaccgacg aagagtcgta     2040
tgagctggtg agggcagaga ggacagaaca cgagtacgtc tacgacgtgg accagagaag     2100
atgctgtaag aaggaagaag ctgcaggact ggtactggtg ggcgacttga ctaatccgcc     2160
```

```
ctaccacgaa ttcgcatatg aagggctaaa aatccgccct gcctgcccat acaaaattgc    2220
agtcatagga gtcttcggag taccaggatc tggcaagtca gctattatca agaacctagt    2280
taccaggcaa gacctggtga ctagcggaaa gaaagaaaac tgccaagaaa tcaccaccga    2340
cgtgatgaga cagagaggtc tagagatatc tgcacgtacg gttgactcgc tgctcttgaa    2400
tggatgtaac agaccagtcg acgtgttgta cgtagacgag gcgtttgcgt gccactctgg    2460
aacgttactt gcattgatcg ccttggtgag accaagacag aaagttgtac tttgtggtga    2520
cccgaagcag tgcggcttct tcaatatgat gcagatgaaa gtcaactata atcacaacat    2580
ctgcacccaa gtgtaccaca aaagtatctc caggcggtgt acactgcctg tgactgccat    2640
tgtgtcatcg ttgcattacg aaggcaaaat gcgcactacg aatgagtaca acaagccgat    2700
tgtagtggac actacaggct caacaaaacc tgaccctgga gatctcgtgt taacgtgctt    2760
cagaggatgg gttaaacaac tgcaaattga ctatcgtgga cacgaggtca tgacagcagc    2820
cgcatcccaa gggttaacca gaaaggagt ttacgcagtt aggcaaaaag ttaacgaaaa    2880
cccgctttat gcatcaacgt cagagcacgt caacgtactc ctaacgcgta cggaaggtaa    2940
actggtatgg aagacactct ccggtgaccc gtggataaag acgctgcaga acccaccgaa    3000
aggaaacttc aaagcaacta ttaaggagtg ggaggtggag catgcatcaa taatggcggg    3060
catctgcagt caccaaatga cctttgatac attccaaaac aaagccaacg tttgttgggc    3120
taagagtttg gtccctatcc tcgaaacagc ggggataaaa ctaaacgaca ggcagtggtc    3180
ccagataatt caagccttca aagaagacaa agcatattca cccgaagtag ccctgaatga    3240
aatatgcacg cgcatgtatg gggtggatct agacagcggg ctattttcta aaccgttggt    3300
gtctgtgtat tacgcggata accactggga taataggcct ggagggaaga tgttcggatt    3360
caaccccgag gcagcatcca ttctagaaag aaagtatcca tttacaaaag ggaagtggaa    3420
catcaacaag cagatctgcg tgactaccag gaggatagaa gacttcaacc ctaccaccaa    3480
cattataccg gccaacagga gactaccaca ctcattagtg gccgaacacc gcccagtaaa    3540
aggggaaaga atggaatggc tggttaacaa gataaacggc caccacgtgc tcctggtcag    3600
tggctgtagc cttgcactgc ctactaagag agtcacttgg gtagcgccac taggtgtccg    3660
cggagcggac tatacataca acctagagtt gggtctgcca gcaacgcttg gtaggtatga    3720
cctagtggtc ataaacatcc acacaccttt tcgcatacac cattatcaac agtgcgtaga    3780
ccacgcaatg aaactgcaaa tgctcggggg tgactcattg agactgctca aaccgggtgg    3840
ctctctattg atcagagcat atggttacgc agatagaacc agtgaacgag tcatctgcgt    3900
attgggacgc aagtttagat catctagagc gttgaaacca ccatgtgtca ccagcaacac    3960
tgagatgttt tttctattca gcaactttga caatggcaga aggaatttca caactcatgt    4020
catgaacaat caactgaatg cagcctttgt aggacaggcc acccgagcag atgtgcacc    4080 gtcgtaccgg gtaaaacgca tggatatcgc gaagaacgat gaagagtgcg tagtcaacgc    4140
cgccaaccct cgcgggttac caggtgacgg tgtttgcaag gcagtataca aaaatggcc    4200 ggagtccttt aagaacagtg caacaccagt gggaaccgca aaaacagtca tgtgcggtac    4260
gtatccagta atccacgccg ttggaccaaa cttctctaat tattcggagt ctgaagggga    4320
ccgagaattg gcggctgcct atcgagaagt cgcaaaggag gtaactagac tgggagtaaa    4380
tagtgtagct atacctctcc tctccacagg tgtatactca ggagggaaag acaggctgac    4440
ccagtcactg aaccacctct ttacagccat ggactcgacg gatgcagacg tggtcatcta    4500
ctgccgcgac aaagaatggg agaagaaaat atctgaggcc atacagatgc ggacccaagt    4560
```

```
ggagctgctg gatgagcaca tctccataga ctgcgatgtt gttcgcgtgc accctgacag    4620
cagcttggca ggcagaaaag gatacagcac cacggaaggc gcactgtact catatctaga    4680
agggacccgt tttcaccaaa cggcagtgga tatggcagag atatatacta tgtggccaaa    4740
gcaaacagag gccaacgagc aagtttgcct atatgccctg ggggaaagta ttgaatcgat    4800
caggcagaaa tgcccggtgg atgatgcaga tgcatcatct cccccgaaaa ctgtcccgtg    4860
cctctgccgt tacgccatga caccagaacg cgttacccga cttcgcatga accatgtcac    4920
aagcataatt gtgtgttctt cgtttcccct tccaaagtac aaaatagaag gagtgcaaaa    4980
agtcaaatgc tccaaggtaa tgctatttga ccacaacgtg ccatcgcgcg taagtccaag    5040
ggaatacaga ccttcccagg agtctgtaca ggaagcgagt acgaccacgt cactgacgca    5100
tagccaattc gatctaagcg ttgacggcaa gatactgccc gtcccgtcag acctggatgc    5160
tgacgcccca gccctagaac cagcccttga cgacggggcg atacacacgt tgccatctgc    5220
aaccggaaac cttgcggccg tgtctgactg ggtaatgagc accgtacctg tcgcgccgcc    5280
cagaagaagg cgagggagaa acctgactgt gacatgcgac gagagagaag ggaatataac    5340
acccatggct agcgtccgat tctttagggc agagctgtgt ccagtcgtac aagaaacagc    5400
ggagacgcgt gacacagcta tgtctcttca ggcaccgccg agtaccgcca cggaactgag    5460
tcacccgccg atctccttcg gtgcaccaag cgagacgttc cccatcacat tggggactt    5520 caacgaagga gaaatcgaaa gcttgtcttc tgagctacta actttcggag acttcctacc    5580
cggagaagtg gatgatttga cagatagcga ctggtccacg tgctcagaca cggacgacga    5640
gttacgacta gacagggcag gtgggtatat attctcgtcg gacactggtc caggtcattt    5700
acaacagaag tcagtacgcc agtcagtgct gccggtgaac accctggagg aagtccacga    5760
ggagaagtgt tacccaccta agctggatga agcaaaggag caactactac ttaagaaact    5820
ccaggagagt gcatccatgg ccaacagaag caggtatcag tcgcgcaaag tagaaaacat    5880
gaaagcaaca atcatccaga gactaaagag aggctgtaga ttatacttaa tgtcagagac    5940
cccaaaagtc cctacctacc ggaccacata tccggcgcct gtgtactcgc ctccgattaa    6000
cgtccgactg tccaaccccg agtccgcagt ggcagcatgc aatgagttct ggctagaaaa    6060
ctatccaact gtttcatcat accaaatcac cgacgagtat gatgcatatc tagacatggt    6120
ggacgggtcg gagagttgtc tggaccgagc gacattcaat ccgtcaaaac ttaggagcta    6180
cccaaaacag cacgcttacc acgcgccctc catcagaagc gctgtaccgt ccccattcca    6240
gaacacacta cagaatgtac tggcagcagc cacgaaaaga aactgcaacg tcacacagat    6300
gagggaatta cccactttgg actcagcagt attcaacgtg gagtgtttca aaaaattcgc    6360
atgcaaccaa gaatactggg aagaatttgc tgccagccct atcaggataa caactgagaa    6420
tttaacaacc tatgttacta aactaaaggg gccaaaagca gcagcgctat ttgcaaaaac    6480
ccataatctg ctgccactgc aggaagtgcc aatggatagg ttcacagtag acatgaaaag    6540
ggatgtgaag gtgactcctg gtacaaagca cacagaggaa agacctaagg tacaggttat    6600
acaggcggct gaaccttgg caacagcata cctatgtggg attcacagag agctggttag    6660
gaggctgaac gccgtcctcc tacccaatgt acatacacta tttgacatgt ctgccgagga    6720
tttcgatgcc atcatagccg cacactttaa gccaggagac actgttttag aaacggacat    6780
agcctccttt gataagagcc aagatgattc acttgcgctt actgctttaa tgctgttaga    6840
ggatttaggg gtggatcact ccctgttgga cttgatagag gctgctttcg gagagatttc    6900
```

```
cagctgtcat ctaccgacag gtacgcgctt caagttcggc gccatgatga aatctggtat    6960
gttcctaact ctgttcgtca acacactgct aaatatcacc atcgccagcc gagtgctgga    7020
agatcgtctg acaaaatccg cgtgcgcagc cttcatcggc gacgacaaca taatacatgg    7080
agtcgtctcc gatgaattga tggcagccag atgcgccact tggatgaaca tggaagtgaa    7140
gatcatagat gcagttgtat cccagaaagc cccttacttt tgtggagggt ttatactgca    7200
cgatatcgtg acaggaacag cttgcagagt ggcagacccg ctaaaaaggc tatttaaact    7260
gggcaaaccg ctagcggcag gtgacgaaca agatgaggat agaagacgag cgctggctga    7320
cgaagtggtc agatggcaac gaacagggct aattgatgag ttggagaaag cggtatactc    7380
taggtatgaa gtgcagggta tatcagttgt ggtaatgtcc atggccacct ttgcaagctc    7440
cagatccaac ttcgagaagc tcagaggacc cgtcgtaact ttgtacggcg gtcctaaata    7500
ggtacgcact acagctacct attttgcaga agccgacagt aagtacctaa acactaatca    7560
gctacaatgg agttcatccc aacccaaact ttttacaaca ggaggtacca gcctcgaccc    7620
tggactccgc gccctactat ccaagtcatc aggcccagac cgcgcccgca gaggcaagct    7680
gggcaacttg cccagctgat ctcagcagtt aataaactga caatgcgcgc ggtaccccaa    7740
cagaagccac gcaagaatcg gaagaataag agcaaaagc aaaagcagca ggcgccacaa    7800
aacaacacaa accaaaagaa gcagccacct aaaaagaaac cagctcaaaa gaaaaagaag    7860
ccgggccgca gagagaggat gtgcatgaaa atcgaaaatg actgtatttt cgaagtcaag    7920
cacgaaggta aggtaacagg ttacgcgtgc ttggtggggg acaaagtaat gaaaccagca    7980
cacgtaaagg ggaccatcga taacgcggac ctggccaaat tggcctttaa gcggtcatct    8040
aagtacgacc ttgaatgcgc gcagatacccc gtgcacatga agtccgacgc ttcgaagttc    8100
acccatgaga aaccggaggg gtactacaac tggcaccacg gagcagtaca gtactcagga    8160
ggccggttca ccatccctac aggtgcgggc aaaccagggg acagcggtag accgatcttc    8220
gacaacaagg gacgcgtggt ggccatagtc ttaggaggag ctaatgaagg agcccgtaca    8280
gccctctcag tggtgacctg gaataaagac attgtcacta aaatcacccc tgagggagcc    8340
gaagagtgga gtcttgccat cccagttatg tgcctgttgg caaataccac gttcccctgc    8400
tcccagcccc cttgcatacc ctgctgctac gaaaaggaac cggaggaaac cctacgcatg    8460
cttgaggaca cgtcatgag acctgggtac tatcagctgc tacaagcatc attaacatgt    8520 tctcccccacc gccagcgacg cagcaccaag gacaacttca atgtctataa agccacaaga    8580 ccataacctag ctcactgtcc cgactgtgga aagggcact cgtgccatag tcccgtagca    8640
ctagaacgca tcagaaatga agcgacagac gggacgctga aaatccaggt ctccttgcaa    8700
attggaatag ggacggatga tagccatgat tggaccaagc tgcgttacat ggacaatcac    8760
ataccagcag acgcagggag ggccgggcta tttgtaagaa catcagcacc atgcacgatt    8820 actgaacaa tgggacactt catcctggcc cgatgtccga aggagaaac tctgacggtg    8880 ggattcactg acagtaggaa gattagtcac tcatgtacgc acccatttca ccacgaccct    8940
cctgtgatag gccgggaaaa attccattcc cgaccgcagc acggtaaaga gctaccttgc    9000
agcacgtacg tgcagagcaa cgccgcaact gccgaggaga tagaggtaca catgcccccca    9060 gacacccctg atcgcacatt gctgtcacaa cagtccggca acgtaaagat cacagtcaat    9120
agtcagacgg tgcggtataa gtgtaattgc ggtggctcaa atgaaggact aataactaca    9180
gataaagtga ttaataactg caaggttgat caatgtcatg ccgcggtcac caatcacaaa    9240
aagtggcagt ataactcccc tctggtcccg cgtaacgctg aactcgggga ccgaaaagga    9300
```

```
aaaattcaca tcccgtttcc gctggcaaat gtaacatgca tggtgcctaa agcaaggaac    9360
cccaccgtga cgtacgggaa aaaccaagtc atcatgctac tgtatcctga ccacccaaca    9420
ctcctgtcct accggagtat gggagaagaa ccaaactatc aagaagagtg ggtgacgcac    9480
aagaaggagg tcgtgctaac cgtgccgact gaagggctcg aggttacgtg gggcaacaac    9540
gagccgtata agtattggcc gcagttatct gcaaacggta cagcccacgg ccacccgcat    9600
gagataatct tgtactatta tgagctgtac cctactatga ctgtagtagt tgtgtcagtg    9660
gcctcgttca tactcctgtc gatggtgggt atggcagtgg ggatgtgcat gtgtgcacga    9720
cgcagatgca tcacaccata cgaactgaca ccaggagcta ccgtcccttt cctgcttagc    9780
ctaatatgct gcatcagaac agctaaagcg gccacatacc aagaggctgc ggtatacctg    9840
tggaacgagc agcaaccttt gttttggcta caagccctta ttccgctggc agccctgatt    9900
gtcctatgca actgtctgag actcttacca tgctgttgta aaacgttggc tttttttagcc   9960 gtaatgagca tcggtgccca cactgtgagc gcgtacgaac acgtaacagt gatcccgaac   10020
acggtgggag taccgtataa gactctagtc aacagaccgg gctacagccc catggtactg   10080
gagatggagc tactgtcagt cactttggag ccaacgctat cgcttgatta catcacgtgc   10140
gaatacaaaa ccgtcatccc gtctccgtac gtgaaatgct gcggtacagc agagtgcaag   10200
gacaaaaacc tacctgacta cagctgtaag gtcttcaccg gcgtctaccc atttatgtgg   10260
ggcggcgcct actgcttctg cgacgctgaa aacacgcaat tgagcgaagc acatgtggag   10320
aagtccgaat catgcaaaac agaatttgca tcagcataca gggctcatac cgcatccgca   10380
tcagctaagc tccgcgtcct ttaccaagga aataacatca ctgtaactgc ctatgcaaac   10440
ggcgaccatg ccgtcacagt taaggacgcc aaattcattg tggggccaat gtcttcagcc   10500
tggacacctt ttgacaacaa aatcgtggtg tacaaaggtg acgtttacaa catggactac   10560 ccgcccttg gcgcaggaag accaggacaa tttggcgata tccaaagtcg cacgcctgag   10620
agcaaagacg tctatgctaa cacacaactg gtactgcaga gaccggctgc gggtacggta   10680
cacgtgccat actctcaggc accatctggc tttaagtatt ggttaaaaga acgaggggcg   10740
tcgctacagc acacagcacc atttggctgc caaatagcaa caaacccggt aagagcgatg   10800
aactgcgccg tagggaacat gcccatctcc atcgacatac cggatgcggc cttcactagg   10860
gtcgtcgacg cgccctcttt aacggacatg tcatgcgagg taccagcctg cacccattcc   10920
tcagactttg ggggcgtcgc cattattaaa tatgcagtca gcaagaaagg caagtgtgcg   10980
gtgcattcga tgaccaacgc cgtcactatc cgggaagctg agatagaagt tgaagggaat   11040
tctcagctgc aaatctcttt ctcgacggcc ttggccagcg ccgaattccg cgtacaagtc   11100
tgttctacac aagtacactg tgcagccgag tgccacccct cgaaggacca catagtcaac   11160
tacccggcgt cacataccac cctcgggtc caggacattt ccgctacggc gatgtcatgg   11220
gtgcagaaga tcacgggagg tgtgggactg gttgtcgctg ttgcagcact gattctaatc   11280
gtggtgctat gcgtgtcgtt cagcaggcac taacttgacg actaagcatg aaggtatatg   11340
tgtcccctaa gagacacacc gtatatagct aataatctgt agatcaaagg gctatataac   11400
ccctgaatag taacaaaata caaatcact aaaaattata aaaaaaaaa aaaaaaaca     11460 gaaaaatata taaataggta tacgtgtccc ctaagagaca cattgtatgt aggtgataag   11520
tatagatcaa agggccgaac aacccctgaa tagtaacaaa atataaaaat taataaaaat   11580
cataaaatag aaaaaccata aacagaagta gttcaagggg ctataaaaac ccctgaatag   11640
```

```
taacaaaaca taaaactaat aaaaatcaaa tgaataccat aattggcaaa cggaagagat    11700
gtaggtactt aagcttccta aaagcagccg aactcacttt gagatgtagg catagcatac    11760
cgaactcttc cacgattctc cgaacccaca gggacgtagg agatgttatt ttgttttaa     11820 tatttc                                                              11826

<210> SEQ ID NO 27
<211> LENGTH: 21
<212> TYPE: DNA
<213> ORGANISM: Artificial Sequence
<220> FEATURE:
<223> OTHER INFORMATION: ZIKV Forward Primer
<220> FEATURE:
<221> NAME/KEY: source
<222> LOCATION: (1)..(21)
<223> OTHER INFORMATION: sequence is synthesized

<400> SEQUENCE: 27
cagctggcat catgaagaay c                                             21

<210> SEQ ID NO 28
<211> LENGTH: 22
<212> TYPE: DNA
<213> ORGANISM: Artificial Sequence
<220> FEATURE:
<223> OTHER INFORMATION: ZIKV Reverse Primer 1
<220> FEATURE:
<221> NAME/KEY: source
<222> LOCATION: (1)..(22)
<223> OTHER INFORMATION: sequence is synthesized

<400> SEQUENCE: 28
cacttgtccc atcttcttct cc                                            22

<210> SEQ ID NO 29
<211> LENGTH: 22
<212> TYPE: DNA
<213> ORGANISM: Artificial Sequence
<220> FEATURE:
<223> OTHER INFORMATION: ZIKV Reverse Primer 2
<220> FEATURE:
<221> NAME/KEY: source
<222> LOCATION: (1)..(22)
<223> OTHER INFORMATION: sequence is synthesized

<400> SEQUENCE: 29
cacctgtccc atctttttct cc                                            22

<210> SEQ ID NO 30
<211> LENGTH: 21
<212> TYPE: DNA
<213> ORGANISM: Artificial Sequence
<220> FEATURE:
<223> OTHER INFORMATION: ZIKV Probe
<220> FEATURE:
<221> NAME/KEY: source
<222> LOCATION: (1)..(21)
<223> OTHER INFORMATION: sequence is synthesized

<400> SEQUENCE: 30
cygttgtgga tggaatagtg g                                             21

<210> SEQ ID NO 31
<211> LENGTH: 10794
<212> TYPE: DNA
<213> ORGANISM: Zika virus
<300> PUBLICATION INFORMATION:
<308> DATABASE ACCESSION NUMBER: NCBI/NC_012532
```

<309> DATABASE ENTRY DATE: 2016-02-08
<313> RELEVANT RESIDUES IN SEQ ID NO: (1)..(10794)

<400> SEQUENCE: 31

```
agttgttgat ctgtgtgagt cagactgcga cagttcgagt ctgaagcgag agctaacaac      60
agtatcaaca ggtttaattt ggatttggaa acgagagttt ctggtcatga aaaaccccaa     120
agaagaaatc cggaggatcc ggattgtcaa tatgctaaaa cgcggagtag cccgtgtaaa     180
cccccttggga ggtttgaaga ggttgccagc cggacttctg ctgggtcatg acccatcag    240
aatggttttg gcgatactag ccttttttgag atttacagca atcaagccat cactgggcct    300
tatcaacaga tgggggttccg tggggaaaaa agaggctatg gaaataataa agaagttcaa    360
gaaagatctt gctgccatgt tgagaataat caatgctagg aaagagagga agagacgtgg    420
cgcagacacc agcatcggaa tcattggcct cctgctgact acagccatgg cagcagagat    480
cactagacgc gggagtgcat actacatgta cttggatagg agcgatgccg ggaaggccat    540
ttcgtttgct accacattgg gagtgaacaa gtgccacgta cagatcatgg acctcgggca    600
catgtgtgac gccaccatga gttatgagtg ccctatgctg gatgagggag tggaaccaga    660
tgatgtcgat tgctggtgca acacgacatc aacttgggtt gtgtacggaa cctgtcatca    720
caaaaaggt gaggcacggc gatctagaag agccgtgacg ctcccttctc actctacaag    780
gaagttgcaa acgcggtcgc agacctggtt agaatcaaga gaatacacga agcacttgat    840
caaggttgaa aactggatat tcaggaaccc cgggtttgcg ctagtggccg ttgccattgc    900
ctggcttttg ggaagctcga cgagccaaaa agtcatatac ttggtcatga tactgctgat    960
tgccccggca tacagtatca ggtgcattgg agtcagcaat agagacttcg tggagggcat   1020
gtcaggtggg acctgggttg atgttgtctt ggaacatgga ggctgcgtta ccgtgatggc   1080
acaggacaag ccaacagtcg acatagagtt ggtcacgacg acggttagta acatggccga   1140
ggtaagatcc tattgctacg aggcatcgat atcggacatg gcttcggaca gtcgttgccc   1200
aacacaaggt gaagcctacc ttgacaagca atcagacact caatatgtct gcaaaagaac   1260
attagtggac agaggttggg gaaacggttg tggacttttt ggcaaaggga gcttggtgac   1320
atgtgccaag tttacgtgtt ctaagaagat gaccgggaag agcattcaac cggaaaatct   1380
ggagtatcgg ataatgctat cagtgcatgg ctcccagcat agcgggatga ttggatatga   1440
aactgacgaa gatagagcga aagtcgaggt tacgcctaat tcaccaagag cggaagcaac   1500
cttgggaggc tttggaagct taggacttga ctgtgaacca aggacaggcc ttgacttttc   1560
agatctgtat tacctgacca tgaacaataa gcattggttg gtgcacaaag agtggtttca   1620
tgacatccca ttgccttggc atgctggggc agacaccgga actccacact ggaacaacaa   1680
agaggcattg gtagaattca aggatgccca cgccaagagg caaaccgtcg tcgttctggg   1740
gagccaggaa ggagccgttc acacggctct cgctggagct ctagaggctg agatggatgg   1800
tgcaaaggga aggctgttct ctggccattt gaaatgccgc ctaaaaatgg acaagcttag   1860
attgaagggc gtgtcatatt ccttgtgcac tgcggcattc acattcacca aggtcccagc   1920
tgaaacactg catggaacag tcacagtgga ggtgcagtat gcagggacag atggaccctg   1980
caagatccca gtccagatgg cggtggacat gcagaccctg acccccagttg gaaggctgat   2040
aaccgccaac cccgtgatta ctgaaagcac tgagaactca aagatgatgt tggagcttga   2100
cccaccattt ggggattctt acattgtcat aggagttggg gacaagaaaa tcacccacca   2160
ctggcatagg agtggtagca ccatcggaaa ggcatttgag gccactgtga gaggcgccaa   2220
```

```
gagaatggca gtcctggggg atacagcctg ggacttcgga tcagtcgggg gtgtgttcaa    2280
ctcactgggt aagggcattc accagatttt tggagcagcc ttcaaatcac tgtttggagg    2340
aatgtcctgg ttctcacaga tcctcatagg cacgctgcta gtgtggttag gtttgaacac    2400
aaagaatgga tctatctccc tcacatgctt ggccctgggg ggagtgatga tcttcctctc    2460
cacggctgtt tctgctgacg tggggtgctc agtggacttc tcaaaaaagg aaacgagatg    2520
tggcacgggg gtattcatct ataatgatgt tgaagcctgg agggaccggt acaagtacca    2580
tcctgactcc ccccgcagat tggcagcagc agtcaagcag gcctgggaag aggggatctg    2640
tgggatctca tccgtttcaa gaatggaaaa catcatgtgg aaatcagtag aaggggagct    2700
caatgctatc ctagaggaga atggagttca actgacagtt gttgtgggat ctgtaaaaaa    2760
ccccatgtgg agaggtccac aaagattgcc agtgcctgtg aatgagctgc cccatggctg    2820
gaaagcctgg gggaaatcgt attttgttag ggcggcaaag accaacaaca gttttgttgt    2880
cgacggtgac acactgaagg aatgtccgct tgagcacaga gcatgaata gttttcttgt    2940 ggaggatcac gggtttggag tcttccacac cagtgtctgg cttaaggtca gagaagatta    3000
ctcattagaa tgtgacccag ccgtcatagg aacagctgtt aagggaaggg aggccgcgca    3060
cagtgatctg ggctattgga ttgaaagtga aagaatgac acatggaggc tgaagagggc    3120
ccacctgatt gagatgaaaa catgtgaatg gccaaagtct cacacattgt ggacagatgg    3180
agtagaagaa agtgatctta tcatacccaa gtctttagct ggtccactca gccaccacaa    3240
caccagagag ggttacagaa cccaagtgaa agggccatgg cacagtgaag agcttgaaat    3300
ccggtttgag aatgtccag gcaccaaggt ttacgtggag gagacatgcg gaactagagg    3360
accatctctg agatcaacta ctgcaagtgg aagggtcatt gaggaatggt gctgtaggga    3420
atgcacaatg cccccactat cgtttcgagc aaaagacggc tgctggtatg aatggagat    3480 aaggcccagg aaagaaccag agagcaactt agtgaggtca atggtgacag cggggtcaac    3540
cgatcatatg gaccacttct ctcttggagt gcttgtgatt ctactcatgg tgcaggaggg    3600
gttgaagaag agaatgacca caaagatcat catgagcaca tcaatggcag tgctggtagt    3660
catgatcttg ggaggatttt caatgagtga cctggccaag cttgtgatcc tgatgggtgc    3720
tactttcgca gaaatgaaca ctggaggaga tgtagctcac ttggcattgg tagcggcatt    3780
taaagtcaga ccagccttgc tggtctcctt catttcaga gccaattgga cccccgtga    3840 gagcatgctg ctagccctgg cttcgtgtct tctgcaaact gcgatctctg ctcttgaagg    3900
tgacttgatg gtcctcatta atggatttgc tttggcctgg ttggcaattc gagcaatggc    3960
cgtgccacgc actgacaaca tcgctctacc aatcttggct gctctaacac cactagctcg    4020
aggcacactg ctcgtggcat ggagagcggg cctggctact tgtggaggga tcatgctcct    4080
ctccctgaaa gggaaaggta gtgtgaagaa gaacctgcca tttgtcatgg ccctgggatt    4140
gacagctgtg agggtagtag accctattaa tgtggtagga ctactgttac tcacaaggag    4200
tgggaagcgg agctggcccc ctagtgaagt tctcacagcc gttggcctga tatgtgcact    4260
ggccggaggg tttgccaagg cagacattga tggctggga cccatggctg cagtaggctt    4320
gctaattgtc agctatgtgg tctcgggaaa gagtgtggac atgtacattg aaagagcagg    4380
tgacatcaca tgggaaaagg acgcggaagt cactggaaac agtcctcggc ttgacgtggc    4440
actggatgag agtggtgact tctccttggt agaggaagat ggtccaccca tgagagagat    4500
catactcaag gtggtcctga tggccatctg tggcatgaac ccaatagcta tacctttgc    4560 tgcaggagcg tggtatgtgt atgtgaagac tgggaaaagg agtggcgccc tctgggacgt    4620
```

```
gcctgctccc aaagaagtga agaaaggaga gaccacagat ggagtgtaca gagtgatgac    4680
tcgcagactg ctaggttcaa cacaggttgg agtgggagtc atgcaagagg gagtcttcca    4740
caccatgtgg cacgttacaa aaggagccgc actgaggagc ggtgagggaa gacttgatcc    4800
atactggggg gatgtcaagc aggacttggt gtcatactgt gggccttgga agttggatgc    4860
agcttgggat ggactcagcg aggtacagct tttggccgta cctcccggag agagggccag    4920
aaacattcag accctgcctg gaatattcaa gacaaaggac ggggacatcg gagcagttgc    4980
tctggactac cctgcaggga cctcaggatc tccgatccta gacaaatgtg aagagtgat     5040 aggactctat ggcaatgggg ttgtgatcaa gaatggaagc tatgttagtg ctataaccca    5100
gggaaagagg gaggaggaga ctccggttga atgtttcgaa ccctcgatgc tgaagaagaa    5160
gcagctaact gtcttggatc tgcatccagg agccggaaaa accaggagag ttcttcctga    5220
aatagtccgt gaagccataa aaagagact ccggacagtg atcttggcac caactagggt     5280
tgtcgctgct gagatggagg aggccttgag aggacttccg gtgcgttaca tgacaacagc    5340
agtcaacgtc acccattctg ggacagaaat cgttgatttg atgtgccatg ccactttcac    5400
ttcacgctta ctacaaccca tcagagtccc taattacaat ctcaacatca tggatgaagc    5460
ccacttcaca gacccctcaa gtatagctgc aagaggatac atatcaacaa gggttgaaat    5520
gggcgaggcg gctgccattt ttatgactgc cacaccacca ggaacccgtg atgcgtttcc    5580
tgactctaac tcaccaatca tggacacaga agtggaagtc ccagagagag cctggagctc    5640
aggctttgat tgggtgacag accattctgg gaaaacagtt tggttcgttc caagcgtgag    5700
aaacggaaat gaaatcgcag cctgtctgac aaaggctgga aagcgggtca tacagctcag    5760
caggaagact tttgagacag aatttcagaa aacaaaaaat caagagtggg acttttgtcat   5820 aacaactgac atctcagaga tgggcgccaa cttcaaggct gaccgggtca tagactctag    5880
gagatgccta aaaccagtca tacttgatgg tgagagagtc atcttggctg ggcccatgcc    5940
tgtcacgcat gctagtgctg ctcagaggag aggacgtata ggcaggaacc ctaacaaacc    6000
tggagatgag tacatgtatg gaggtgggtg tgcagagact gatgaaggcc atgcacactg    6060
gcttgaagca agaatgcttc ttgacaacat ctacctccag gatggcctca tagcctcgct    6120
ctatcggcct gaggccgata aggtagccgc cattgaggga gagtttaagc tgaggacaga    6180
gcaaaggaag accttcgtgg aactcatgaa gagaggagac cttcccgtct ggctagccta    6240
tcaggttgca tctgccggaa taacttacac agacagaaga tggtgctttg atggcacaac    6300
caacaacacc ataatggaag acagtgtacc agcagaggtt tggacaaagt atggagaaa     6360 gagagtgctc aaaccgagat ggatggatgc tagggtctgt tcagaccatg cggccctgaa    6420
gtcgttcaaa gaattcgccg ctggaaaaag aggagcggct ttgggagtaa tggaggccct    6480
gggaacactg ccaggacaca tgacagagag gtttcaggaa gccattgaca acctcgccgt    6540
gctcatgcga gcagagactg gaagcaggcc ttataaggca gcggcagccc aactgccgga    6600
gaccctagag accattatgc tcttaggttt gctgggaaca gtttcactgg ggatcttctt    6660
cgtcttgatg cggaataagg gcatcggaaa gatgggcttt ggaatggtaa cccttggggc    6720
cagtgcatgg ctcatgtggc tttcggaaat tgaaccagcc agaattgcat gtgtcctcat    6780
tgttgtgttt ttattactgg tggtgctcat acccgagcca gagaagcaaa gatctcccca    6840
agataaccag atggcaatta tcatcatggt ggcagtgggc cttctaggtt tgataactgc    6900
aaacgaactt ggatggctgg aaagaacaaa aaatgacata gctcatctaa tgggaaggag    6960
```

```
agaagaagga gcaaccatgg gattctcaat ggacattgat ctgcggccag cctccgcctg    7020
ggctatctat gccgcattga caactctcat cacccccagct gtccaacatg cggtaaccac    7080
ttcatacaac aactactcct taatggcgat ggccacacaa gctggagtgc tgtttggcat    7140
gggcaaaggg atgccatttta tgcatgggga ccttggagtc ccgctgctaa tgatgggttg    7200
ctattcacaa ttaacacccc tgactctgat agtagctatc attctgcttg tggcgcacta    7260
catgtacttg atcccaggcc tacaagcggc agcagcgcgt gctgcccaga aaaggacagc    7320
agctggcatc atgaagaatc ccgttgtgga tggaatagtg gtaactgaca ttgacacaat    7380
gacaatagac ccccaggtgg agaagaagat gggacaagtg ttactcatag cagtagccat    7440
ctccagtgct gtgctgctgc ggaccgcctg gggatggggg gaggctggag ctctgatcac    7500
agcagcgacc tccaccttgt gggaaggctc tccaaacaaa tactggaact cctctacagc    7560
cacctcactg tgcaacatct tcagaggaag ctatctggca ggagcttccc ttatctatac    7620
agtgacgaga aacgctggcc tggttaagag acgtggaggt gggacgggag agactctggg    7680
agagaagtgg aaagctcgtc tgaatcagat gtcggccctg gagttctact cttataaaaa    7740
gtcaggtatc actgaagtgt gtagagagga ggctcgccgt gccctcaagg atggagtggc    7800
cacaggagga catgccgtat cccggggaag tgcaaagatc agatggttgg aggagagagg    7860
atatctgcag ccctatggga aggttgttga cctcggatgt ggcagagggg gctggagcta    7920
ttatgccgcc accatccgca aagtgcagga ggtgagagga tacacaaagg gaggtcccgg    7980
tcatgaagaa cccatgctgg tgcaaagcta tgggtggaac atagttcgtc tcaagagtgg    8040
agtggacgtc ttccacatgg cggctgagcc gtgtgacact ctgctgtgtg ataggtga     8100 gtcatcatct agtcctgaag tggaagagac acgaacactc agagtgctct ctatggtggg    8160
ggactggctt gaaaaaagac cagggccctt ctgtataaag gtgctgtgcc catacaccag    8220
cactatgatg gaaaccatgg agcgactgca acgtaggcat ggggaggat tagtcagagt    8280 gccattgtgt cgcaactcca cacatgagat gtactgggtc tctggggcaa agagcaacat    8340
cataaaaagt gtgtccacca caagtcagct cctcctggga cgcatggatg ccccaggag    8400 gccagtgaaa tatgaggagg atgtgaacct cggctcgggt acacgagctg tgcaagctg    8460 tgctgaggct cctaacatga aaatcatcgg caggcgcatt gagagaatcc gcaatgaaca    8520
tgcagaaaca tggtttctg atgaaaaacca cccatacagg acatgggcct accatgggag    8580
ctacgaagcc cccacgcaag gatcagcgtc ttccctcgtg aacgggttg ttagactcct    8640 gtcaaagcct tgggacgtgg tgactggagt tacaggaata gccatgactg acaccacacc    8700
atacggccaa caaagagtct tcaaagaaaa agtggacacc agggtgccag atccccaaga    8760
aggcactcgc caggtaatga acatagtctc ttcctggctg tggaaggagc tggggaaacg    8820
caagcggcca cgcgtctgca ccaaagaaga gtttatcaac aaggtgcgca gcaatgcagc    8880
actgggagca atatttgaag aggaaaaaga atggaagacg gctgtggaag ctgtgaatga    8940
tccaaggttt tgggccctag tggataggga gagagaacac cacctgagag gagagtgtca    9000
cagctgtgtg tacaacatga tgggaaaaag agaaaagaag caaggagagt tcgggaaagc    9060
aaaaggtagc cgcgccatct ggtacatgtg gttgggagcc agattcttgg agtttgaagc    9120
ccttggattc ttgaacgagg accattggat gggaagagaa aactcaggag gtggagtcga    9180
agggttagga ttgcaaagac ttggatacat tctagaagaa atgaatcggg caccaggagg    9240
aaagatgtac gcagatgaca ctgctggctg ggacaccgc attagtaagt ttgatctgga    9300
gaatgaagct ctgattacca accaaatgga ggaagggcac agaactctgg cgttggccgt    9360
```

```
gattaaatac acataccaaa acaaagtggt gaaggttctc agaccagctg aaggaggaaa   9420
aacagttatg gacatcattt caagacaaga ccagagaggg agtggacaag ttgtcactta   9480
tgctctcaac acattcacca acttggtggt gcagcttatc cggaacatgg aagctgagga   9540
agtgttagag atgcaagact tatggttgtt gaggaagcca gagaaagtga ccagatggtt   9600
gcagagcaat ggatgggata gactcaaacg aatggcggtc agtggagatg actgcgttgt   9660
gaagccaatc gatgataggt ttgcacatgc cctcaggttc ttgaatgaca tgggaaaagt   9720
taggaaagac acacaggagt ggaaaccctc gactggatgg agcaattggg aagaagtccc   9780
gttctgctcc caccacttca acaagctgta cctcaaggat gggagatcca ttgtggtccc   9840
ttgccgccac caagatgaac tgattggccg agctcgcgtc tcaccagggg caggatggag   9900
catccgggag actgcctgtc ttgcaaaatc atatgcgcag atgtggcagc tcctttattt   9960
ccacagaaga gaccttcgac tgatggctaa tgccatttgc tcggctgtgc cagttgactg  10020
ggtaccaact gggagaacca cctggtcaat ccatggaaag ggagaatgga tgaccactga  10080
ggacatgctc atggtgtgga atagagtgtg gattgaggag aacgaccata tggaggacaa  10140
gactcctgta acaaaatgga cagacattcc ctatctagga aaaagggagg acttatggtg  10200
tggatccctt atagggcaca gaccccgcac cacttgggct gaaaacatca aagacacagt  10260
caacatggtg cgcaggatca taggtgatga agaaaagtac atggactatc tatccaccca  10320
agtccgctac ttgggtgagg aagggtccac acccggagtg ttgtaagcac caattttagt  10380
gttgtcaggc ctgctagtca gccacagttt ggggaaagct gtgcagcctg taacccccc  10440 aggagaagct gggaaaccaa gctcatagtc aggccgagaa cgccatggca cggaagaagc  10500
catgctgcct gtgagcccct cagaggacac tgagtcaaaa aaccccacgc gcttggaagc  10560
gcaggatggg aaaagaaggt ggcgaccttc cccacccttc aatctggggc ctgaactgga  10620
gactagctgt gaatctccag cagagggact agtggttaga ggagaccccc cggaaaacgc  10680
aaaacagcat attgacgtgg gaaagaccag agactccatg agtttccacc acgctggccg  10740
ccaggcacag atcgccgaac ttcggcggcc ggtgtgggga aatccatggt ttct        10794
```

```
<210> SEQ ID NO 32
<211> LENGTH: 10807
<212> TYPE: DNA
<213> ORGANISM: Zika virus
<300> PUBLICATION INFORMATION:
<308> DATABASE ACCESSION NUMBER: GenBank/LC002520
<309> DATABASE ENTRY DATE: 2014-09-12
<313> RELEVANT RESIDUES IN SEQ ID NO: (1)..(10807)

<400> SEQUENCE: 32
agttgttgat ctgtgtgagt cagactgcga cagttcgagt ctgaagcgag agctaacaac     60
agtatcaaca ggtttaattt ggatttggaa acgagagttt ctggtcatga aaaacccaaa    120
gaagaaatcc ggaggattcc ggattgtcaa tatgctaaaa cgcggagtag cccgtgtaaa    180
ccccttggga ggtttgaaga ggttgccagc cggacttctg ctgggtcatg gacccatcag    240
aatggttttg gcgatactag cctttttgag atttacagca atcaagccat cactgggcct    300
tatcaacaga tggggttccg tggggaaaaa agaggctatg gaaataataa agaagttcaa    360
gaaagatctt gctgccatgt tgagaataat caatgctagg aaagagagga agagacgtgg    420
cgcagacacc agcatcggaa tcattggcct cctgctgact acagccatgg cagcagagat    480
cactagacgc gggagtgcat actacatgta cttggatagg agcgatgccg ggaaggccat    540
```

```
ttcgtttgct accacattgg gagtgaacaa gtgccacgta cagatcatgg acctcgggca    600
catgtgtgac gccaccatga gttatgagtg ccctatgctg gatgagggag tggaaccaga    660
tgatgtcgat tgctggtgca acacgacatc aacttgggtt gtgtacggaa cctgtcatca    720
caaaaaaggt gaggcacggc gatctagaag agccgtgacg ctcccttctc actctacaag    780
gaagttgcaa acgcggtcgc agacctggtt agaatcaaga gaatacacga agcacttgat    840
caaggttgaa aactggatat tcaggaaccc cgggtttgcg ctagtggccg ttgccattgc    900
ctggcttttg ggaagctcga cgagccaaaa agtcatatac ttggtcatga tactgctgat    960
tgccccggca tacagtatca ggtgcattgg agtcagcaat agagacttcg tggagggcat    1020
gtcaggtggg acctgggttg atgttgtctt ggaacatgga ggctgcgtta ccgtgatggc    1080
acaggacaag ccaacagttg acatagagtt ggtcacgacg acggttagta acatggccga    1140
ggtaagatcc tattgctacg aggcatcgat atcggacatg gcttcggaca gtcgttgccc    1200
aacacaaggt gaagcctacc ttgacaagca atcagacact caatatgtct gcaaaagaac    1260
attagtggac agaggttggg gaaacggttg tggacttttt ggcaaaggga gcttggtgac    1320
atgtgccaag tttacgtgtt ctaagaagat gaccgggaag agcattcaac cggaaaatct    1380
ggagtatcgg ataatgctat cagtgcatgg ctcccagcat agcgggatga ctgtcaatga    1440
tataggatat gaaactgacg aaaatagagc gaaagtcgag gttacgccta attccaaag    1500 agcggaagca accttgggag gctttggaag cttaggactt gactgtgaac aaggacagg    1560 ccttgacttt tcagatctgt attacctgac catgaacaat aagcattggt tggtgcacaa    1620
agagtggttt catgacatcc cattgccttg gcatgctggg gcagacactg gaactccaca    1680
ctggaacaac aaagaggcat ggtagaatt caaggatgcc cacgccaaga ggcaaaccgt    1740
cgtcgttctg gggagccagg aaggagccgt tcacacggct ctcgctggag ctctagaggc    1800
tgagatggat ggtgcaaagg gaaagctgtt ctctggccat ttgaaatgcc gcctaaaaat    1860
ggacaagctt agattgaagg gcgtgtcata ttccttgtgc actgcggcat tcacattcac    1920
caaggtccca gctgaaacac tgcatggaac agtcacagtg gaggtgcagt atgcagggac    1980
agatggaccc tgcaagatcc cagtccagat ggcggtggac atgcagaccc tgaccccagt    2040
tggaaggctg ataaccgcca accccgtgat tactgaaagc actgagaact caaagatgat    2100
gttggagctt gacccaccat tgggggattc ttacattgtc ataggagttg gggacaagaa    2160
aatcacccac cactggcata ggagtggtag caccatcgga aaggcatttg aggccactgt    2220
gagaggcgcc aagagaatgg cagtcctggg ggatacagcc tgggacttcg gatcagtcgg    2280
gggtgtgttc aactcactgg gtaagggcat tcaccagatt ttttggagcag ccttcaaatc    2340 actgtttgga ggaatgtcct ggttctcaca gatcctcata ggcacgctgc tagtgtggtt    2400
aggtttgaac acaaagaatg gatctatctc cctcacatgc ttggccctgg ggggagtgat    2460
gatcttcctc tccacggctg tttctgctga cgtggggtgc tcagtggact ctcaaaaaa    2520 ggaaacgaga tgtggcacgg gggtattcat ctataatgat gttgaagcct ggagggaccg    2580
gtacaagtac catcctgact cccccgcag attggcagca gcagtcaagc aggcctggga    2640
agaggggatc tgtgggatct catccgtttc aagaatggaa acatcatgt ggaaatcagt    2700 agaaggggag ctcaatgcta tcctagagga gaatggagtt caactgacag ttgttgtggg    2760
atctgtaaaa aaccccatgt ggagaggtcc acaaagattg ccagtgcctg tgaatgagct    2820
gccccatggc tggaaagcct gggggaaatc gtatttgtt agggcggcaa agaccaacaa    2880
cagttttgtt gtcgacggtg acacactgaa ggaatgtccg cttgagcaca gagcatggaa    2940
```

```
tagttttctt gtggaggatc acgggtttgg agtcttccac accagtgtct ggcttaaggt    3000
cagagaagat tactcattag aatgtgaccc agccgtcata ggaacagctg ttaagggaag    3060
ggaggccgcg cacagtgatc tgggctattg gattgaaagt gaaaagaatg acacatggag    3120
gctgaagagg gcccacctga ttgagatgaa aacatgtgaa tggccaaagt ctcacacatt    3180
gtggacagat ggagtagaag aaagtgatct tatcataccc aagtctttag ctggtccact    3240
cagccaccac aacaccagag agggttacag aacccaagtg aaagggccat ggcacagtga    3300
agagcttgaa atccggtttg aggaatgtcc aggcaccaag gtttacgtgg aggagacatg    3360
cggaactaga ggaccatctc tgagatcaac tactgcaagt ggaagggtca ttgaggaatg    3420
gtgctgtagg gaatgcacaa tgcccccact atcgtttcga gcaaaagacg gctgctggta    3480
tggaatggag ataaggccca ggaaagaacc agagagcaac ttagtgaggt caatggtgac    3540
agcggggtca accgatcata tggaccactt ctctcttgga gtgcttgtga ttctactcat    3600
ggtgcaggag gggttgaaga agagaatgac cacaaagatc atcatgagca catcaatggc    3660
agtgctggta gtcatgatct tgggaggatt ttcaatgagt gacctggcca agcttgtgat    3720
cctgatgggt gctactttcg cagaaatgaa cactggagga gatgtagctc acttggcatt    3780
ggtagcggca tttaaagtca gaccagcctt gctggtctcc ttcattttca gagccaattg    3840
gacaccccgt gagagcatgc tgctagccct ggcttcgtgt cttctgcaaa ctgcgatctc    3900
tgctcttgaa ggtgacttga tggtcctcat taatggattt gctttggcct ggttggcaat    3960
tcgagcaatg gccgtgccac gcactgacaa catcgctcta ccaatcttgg ctgctctaac    4020
accactagct cgaggcacac tgctcgtggc atggagagcg ggcctggcta cttgtggagg    4080
gatcatgctc ctctcccctg aagggaaagg tagtgtgaag aagaacctgc catttgtcat    4140
ggcctgggga ttgacagctg tgagggtagt agaccctatt aatgtggtag gactactgtt    4200
actcacaagg agtgggaagc ggagctggcc ccctagtgaa gttctcacag ccgttggcct    4260
gatatgtgca ctggccggag ggtttgccaa ggcagacatt gagatggctg gacccatggc    4320
tgcagtaggc ttgctaattg tcagctatgt ggtctcggga aagagtgtgg acatgtacat    4380
tgaaagagca ggtgacatca catgggaaaa ggacgcggaa gtcactggaa acagtcctcg    4440
gcttgacgtg gcactggatg agagtggtga tttctccttg gtagaggaag atggtccacc    4500
catgagagag atcatactta aggtggtcct gatggccatc tgtggcatga cccaatagc    4560 tataccttt gctgcaggag cgtggtatgt gtatgtgaag actgggaaaa ggagtggcgc    4620
cctctgggac gtgcctgctc ccaaagaagt gaagaaagga gagaccacag atggagtgta    4680
cagagtgatg actcgcagac tgctaggttc aacacaggtt ggagtgggag tcatgcaaga    4740
gggagtcttc cacaccatgt ggcacgttac aaaaggagcc gcactgagga cggtgagggg    4800
aagacttgat ccatactggg gggatgtcaa gcaggacttg gtgtcatact gtgggccttg    4860
gaagttggat gcagcttggg atggactcag cgaggtacag cttttggccg tacctccgg    4920 agagagggcc agaaacattc agaccctgcc tggaatattc aagacaaagg acgggacat    4980 cggagcagtt gctctggact accctgcagg gacctcagga tctccgatcc tagacaaatg    5040
tggaagagta ataggactct atggcaatgg ggttgtgatc aagaatgaa gctatgttag    5100 tgctataacc cagggaaaga gggaggagga gactccggtt gaatgtttcg aaccctcgat    5160
gctgaagaag aagcagctaa ctgtcttgga tctgcatcca ggagccggaa aaaccagag    5220 agttcttcct gaaatagtcc gtgaagccat aaaaaagaga ctccggacag tgatcttggc    5280
```

```
accaactagg gttgtcgctg ctgagatgga ggaggccttg agaggacttc cggtgcgtta    5340
catgacaaca gcagtcaacg tcacccattc tgggacagaa atcgttgatt tgatgtgcca    5400
tgccactttc acttcacgct tactacaacc catcagagtc cctaattaca atctctacat    5460
catggatgaa gcccacttca cagacccctc aagtatagct gcaagaggat atatatcaac    5520
aagggttgaa atgggcgagg cggctgccat ttttatgact gccacaccac caggaacccg    5580
tgatgcgttt cctgactcta actcaccaat catggacaca gaagtggaag tcccagagag    5640
agcctggagc tcaggctttg attgggtgac agaccattct gggaaaacag tttggttcgt    5700
tccaagcgtg agaaacggaa atgaaatcgc agcctgtctg acaaaggctg aaagcgggt    5760
catacagctc agcaggaaga cttttgagac agaatttcag aaaacaaaaa atcaagagtg    5820
ggactttgtc ataacaactg acatctcaga gatgggcgcc aacttcaagg ctgaccgggt    5880
catagactct aggagatgcc taaaaccagt catacttgat ggtgagagag tcatcttggc    5940
tgggcccatg cctgtcacgc atgctagtgc tgctcagagg agaggacgta taggcaggaa    6000
ccctaacaaa cctggagatg agtacatgta tggaggtggg tgtgcagaga ctgatgaagg    6060
ccatgcacac tggcttgaag caagaatgct tcttgacaac atctacctcc aggatggcct    6120
cataggcctcg ctctatcggc ctgaggccga taaggtagcc gccattgagg gagagtttaa    6180
gctgaggaca gagcaaagga agaccttcgt ggaactcatg aagagaggag accttcccgt    6240
ctggctagcc tatcaggttg catctgccgg aataacttac acagacagaa gatggtgctt    6300
tgatggcaca accaacaaca ccataatgga agacagcgta ccagcagagg tgtggacaaa    6360
gtatggagag aagagagtgc tcaaaccgag atggatggat gctagggtct gttcagacca    6420
tgcggccctg aagtcgttca aagaattcgc cgctggaaaa agaggagcgg ctttgggagt    6480
aatggaggcc ctgggaacac tgccaggaca catgacagag aggtttcagg aagccattga    6540
caacctcgcc gtgctcatgc gagcagagac tggaagcagg ccttataagg cagcggcagc    6600
ccaactgccg gagaccctag agaccattat gctcttaggt ttgctgggaa cagtttcact    6660
ggggatcttc ttcgtcttga tgcggaataa gggcatcggg aagatgggct ttggaatggt    6720
aacccttggg gccagtgcat ggctcatgtg gctttcggaa attgaaccag ccagaattgc    6780
atgtgtcctc attgttgtgt ttttattact ggtggtgctc ataccgagc cagagaagca    6840
aagatctccc caagataacc agatggcaat tatcatcatg gtggcagtgg gccttctagg    6900
tttgataact gcaaacgaac ttggatggct ggaaagaaca aaaaatgaca tagctcatct    6960
aatgggaagg agaagaagag gagcaaccat gggattctca atggacattg atctgcggcc    7020
agcctccgcc tgggctatct atgccgcatt gacaactctc atcaccccag ctgtccaaca    7080
tgcggtaacc acttcataca acaactactc cttaatggcg atggccacac aagctggagt    7140
gctgtttggc atgggcaaag ggatgccatt ttatgcatgg gaccttggag tcccgctgct    7200
aatgatgggt tgctattcac aattaacacc cctgactctg ataqtagcta tcattctgct    7260
tgtggcgcac tacatgtact tgatcccagg cctacaagcg gcagcagcgc gtgctgccca    7320
gaaaaggaca gcagctggca tcatgaagaa tcccgttgtg gatggaatag tggtaactga    7380
cattgacaca atgacaatag accccaggt ggagaagaag atgggacaag tgttactcat    7440
agcagtagcc atctccagtg ctgtgctgct gcggaccgcc tggggatggg gggaggctgg    7500
agctctgatc acagcagcga cctccacctt gtgggaaggc tctccaaaca aatactggaa    7560
ctcctctaca gccacctcac tgtgcaacat cttcagagga agctatctgg caggagcttc    7620
ccttatctat acagtgacga gaaacgctgg cctggttaag agacgtggag gtgggacggg    7680
```

```
agagactctg ggagagaagt ggaaagctcg tctgaatcag atgtcggccc tggagttcta   7740
ctcttataaa aagtcaggta tcactgaagt gtgtagagag gaggctcgcc gtgccctcaa   7800
ggatggagtg gccacaggag gacatgccgt atcccgggga agtgcaaagc tcagatggtt   7860
ggtggagaga ggatatctgc agccctatgg gaaggttgtt gacctcggat gtggcagagg   7920
gggctggagc tattatgccg ccaccatccg caaagtgcag gaggtgagag gatacacaaa   7980
gggaggtccc ggtcatgaag aacccatgct ggtgcaaagc tatgggtgga acatagttcg   8040
tctcaagagt ggagtggacg tcttccacat ggcggctgag ccgtgtgaca ctctgctgtg   8100
tgacataggt gagtcatcat ctagtcctga agtggaagag acacgaacac tcagagtgct   8160
ctctatggtg ggggactggc ttgaaaaaag accaggggcc ttctgtataa aggtgctgtg   8220
cccatacacc agcactatga tggaaaccat ggagcgactg caacgtaggc atggggagg    8280 attagtcaga gtgccattgt ctcgcaactc cacacatgag atgtactggg tctctggggc   8340
aaagagcaac atcataaaaa gtgtgtccac cacaagtcag ctcctcctgg acgcatgga    8400 tggccccagg aggccagtga aatatgagga ggatgtgaac ctcggctcgg gtacacgagc   8460
tgtggcaagc tgtgctgagg ctcctaacat gaaaatcatc ggcaggcgca ttgagagaat   8520
ccgcaatgaa catgcagaaa catggtttct tgatgaaaac cacccataca ggacatgggc   8580
ctaccatggg agctacgaag ccccacgca aggatcagcg tcttccctcg tgaacggggt    8640
tgttagactc ctgtcaaagc cttgggacgt ggtgactgga gttacaggaa tagccatgac   8700
tgacaccaca ccatacggcc aacaaagagt cttcaaagaa aaagtggaca ccagggtgcc   8760
agatccccaa gaaggcactc gccaggtaat gaacatagtc tcttcctggc tgtggaagga   8820
gctggggaaa cgcaagcggc cacgcgtctg caccaaagaa gagtttatca acaaggtgcg   8880
cagcaatgca gcactgggag caatatttga agaggaaaaa gaatggaaga cggctgtgga   8940
agctgtgaat gatccaaggt tttgggccct agtggatagg gagagagaac accacctgag   9000
aggagagtgt cacagctgtg tgtacaacat gatgggaaaa agagaaaaga gcaaggaga   9060 gttcgggaaa gcaaaaggta ccgcgccat ctggtacatg tggttgggag ccagattctt    9120
ggagtttgaa gcccttggat tcttgaacga ggaccattgg atgggaagag aaaactcagg   9180
aggtggagtc gaagggttag gattgcaaag acttggatac attctagaag aaatgaatcg   9240
ggcaccagga ggaaagatgt acgcagatga cactgctggc tgggacaccc gcattagtaa   9300
gtttgatctg gagaatgaag ctctgattac caaccaaatg gaggaagggc acagaactct   9360
ggcgttggcc gtgattaaat acacatacca aaacaaagtg gtgaaggttc tcagaccagc   9420
tgaaggagga aaaacagtta tggacatcat ttcaagacaa gaccagagag ggagtggaca   9480
agttgtcact tatgctctca acacattcac caacttggtg gtgcagctta ccgaacat    9540 ggaagctgag gaagtgttag agatgcaaga cttatggttg ttgaggaagc cagagaaagt   9600
gaccagatgt tgcagagca atggatggga tagactcaaa cgaatggcgg tcagtggaga   9660
tgactgcgtt gtgaagccaa tcgatgatag gtttgcacat gccctcaggt tcttgaatga   9720
catgggaaaa gttaggaaag acacacagga gtggaaaccc tcgactggat ggagcaattg   9780
ggaagaagtc ccgttctgct cccaccactt caacaagctg tacctcaagg atgggagatc   9840
cattgtggtc ccttgccgcc accaagatga actgattggc cgagctcgcg tctcaccagg   9900 ggcaggatg agcatccggg agactgcctg tcttgcaaaa tcatatgcgc agatgtggca   9960 gctccttat ttccacagaa gagaccttcg actgatggct aatgccattt gctcggctgt   10020
```

```
                                                                          -continued
gccagttgac tgggtaccaa ctgggagaac cacctggtca atccatggaa agggagaatg  10080
gatgaccact gaggacatgc tcatggtgtg gaatagagtg tggattgagg agaacgacca  10140
tatggaggac aagactcctg taacaaaatg gacagacatt ccctatctag gaaaaaggga  10200
ggacttatgg tgtggatccc ttatagggca cagacccgc accacttggg ctgaaaacat  10260
caaagacaca gtcaacatgg tgcgcaggat cataggtgat gaagaaaagt acatggacta  10320
tctatccacc caagtccgct acttgggtga ggaagggtcc acacccggag tgttgtaagc  10380
accaatttta gtgttgtcag gcctgctagt cagccacagt ttggggaaag ctgtgcagcc  10440
tgtaaccccc ccaggagaag ctgggaaacc aagctcatag tcaggccgag aacgccatgg  10500
cacggaagaa gccatgctgc ctgtgagccc ctcagaggac actgagtcaa aaaaccccac  10560
gcgcttggaa gcgcaggatg ggaaaagaag gtggcgacct tccccaccct tcaatctggg  10620
gcctgaactg gagactagct gtgaatctcc agcagaggga ctagtggtta gaggagaccc  10680
cccggaaaac gcaaaacagc atattgacgc tgggaaagac cagagactcc atgagtttcc  10740
accacgctgg ccgccaggca cagatcgccg aacagcggcg gccggtgtgg ggaaatccat  10800
ggtttct                                                           10807
```